(12) United States Patent
Jones et al.

(10) Patent No.: US 7,582,741 B2
(45) Date of Patent: Sep. 1, 2009

(54) CONDITIONAL DISRUPTION OF DICER1 IN CELL LINES AND NON-HUMAN MAMMALS

(75) Inventors: Stephen Jones, Shrewsbury, MA (US); Zhinqing Zhu, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/191,157

(22) Filed: Jul. 26, 2005

(65) Prior Publication Data

US 2006/0064769 A1 Mar. 23, 2006

Related U.S. Application Data

(60) Provisional application No. 60/591,268, filed on Jul. 26, 2004.

(51) Int. Cl.
*C12N 15/11* (2006.01)
*C12N 15/74* (2006.01)

(52) U.S. Cl. ............... 536/23.1; 536/23.5; 536/24.5; 435/320.1; 435/325; 435/455

(58) Field of Classification Search ............... None
See application file for complete search history.

(56) References Cited

U.S. PATENT DOCUMENTS

| | | | | |
|---|---|---|---|---|
| 4,959,317 | A | 9/1990 | Sauer | |
| 5,777,194 | A * | 7/1998 | Scott et al. | ............... 800/12 |
| 6,194,633 | B1 | 2/2001 | Koretzky et al. | |
| 2004/0045043 | A1 | 3/2004 | Finney et al. | |
| 2004/0086884 | A1 * | 5/2004 | Beach et al. | ............... 435/6 |

FOREIGN PATENT DOCUMENTS

WO   WO-93/22443 A1   11/1993

OTHER PUBLICATIONS

Bernstein et al (Dicer is essential for mouse development.Nature Genetics, 2003. 35(3):215-217).*
PAZ. Pfam database. (www.sanger.ac.uk//cgi-bin/Pfam/getacc?PF02170, downloaded on Feb. 27, 2007).*
Babinet (Genome engineering via homologous recombination in mouse embryonic stem (ES) cells: an amazingly versatile tool for the study of mammalian biology. An. Acad. Bras. Cienc., 2001. 73(3):365-383).*
McPherson et al. Gene bank sequence, Oct. 2002.*
Dicer 1 genomic sequence, NCBI Genome bank, 2008.*
Bernstein, Emily et al., "Dicer is essential for mouse development," *Nature Genetics*, vol. 35(3):215-217 (2003).
Hoess, Ronald H. et al., "P1 site-specific recombination: Nucleotide sequence of the recombining sies," *Proc. Natl. Acad. Sci. USA*, vol. 79:3398-3402 (1982).
Lagos-Quintana, Mariana et al., "Identificaion of Novel Genes Coding for Small Expressed RNAs," *Science*, vol. 294:853-858 (2001).
Lau, Nelson C. et al., "An Abundant Class of Tiny RNAs with Probable Regulatory Roles in *Caenorhabditis elegans*, " *Science*, vol. 294:858-862 (2001).
Lee, Rosalind C. et al., "An Extensive Class of Small RNAs in *Caenorhabditis elegans*," *Science*, vol. 294:862-864 (2001).
Matsuda, Satoru et al., "Molecular cloning and characterization of a novel human gene (HERNA) which encodes a putative RNA-helicase," *Biochimica et Biophysica Acta*, vol. 1490:163-169 (2000).
Nicholson, Rhonda H. et al., "Molecular characterization of a mouse cDNA encoding Dicer, a ribonuclease III ortholog involved in RNA interference," *Mammalian Genome*, vol. 13:67-73 (2002).

* cited by examiner

*Primary Examiner*—Q. Janice Li
(74) *Attorney, Agent, or Firm*—Lahive & Cockfield, LLP; Debra J. Milasincic, Esq.; Cynthia L. Kanik

(57) ABSTRACT

The present invention is based, at least in part, on the generation of cells, cell lines and non-human mammals that contain a synthetic conditional allele of the Dicer1 gene. Many of the constructs, methods, animals and cells of the invention feature recombinase recognition sites (in certain embodiments, loxP sites) positioned on either flank of a sequence that comprises exons 14, 15 and 16 of the Dicer1 gene (in certain embodiments, the mouse Dicer1 gene). Through readily manipulable introduction, administration, or expression of a recombinase (in certain aspects of the invention, the Cre recombinase of bacteriophage P1), exons 14 through 16 of Dicer1 may be directedly excised, producing a functional knockout of Dicer1 in cells containing these recombinase-induced alleles of the invention.

9 Claims, 12 Drawing Sheets

Figure 3
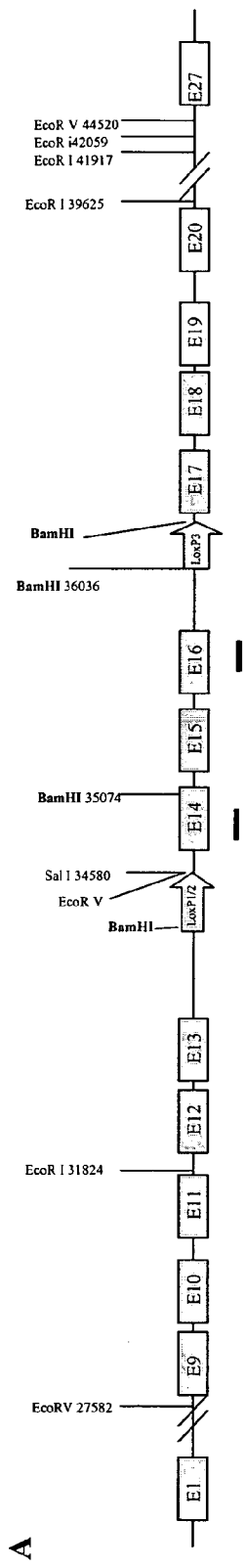
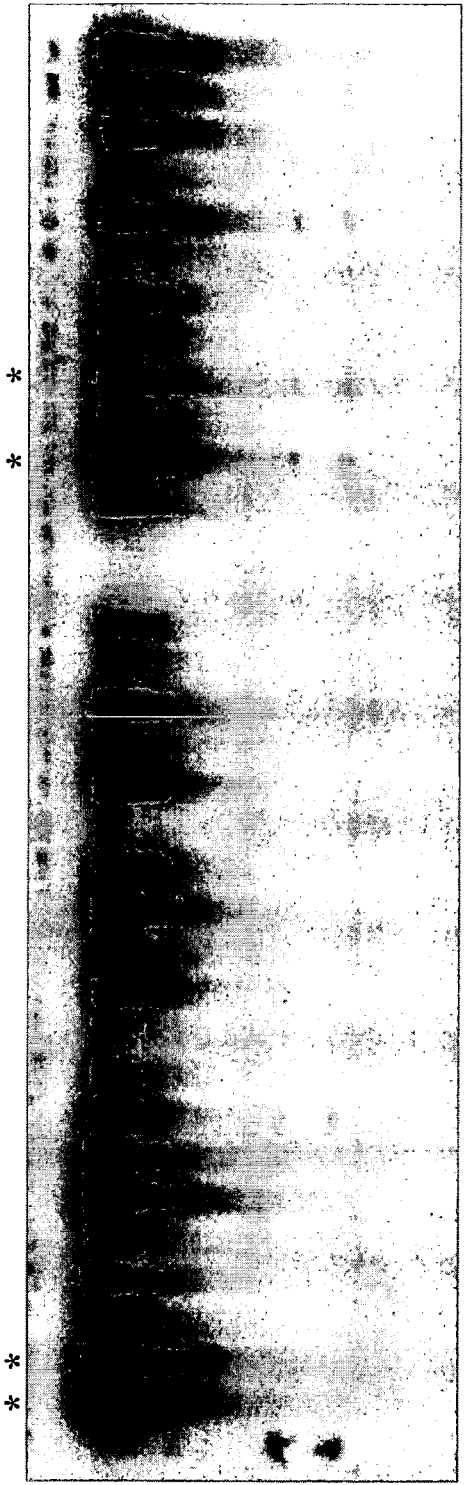
Probes: exon 16 (1Kb band) and exon 14 (0.5kb band) confirm conditional allele
*other surviving clones are knockout-allele arrangements*

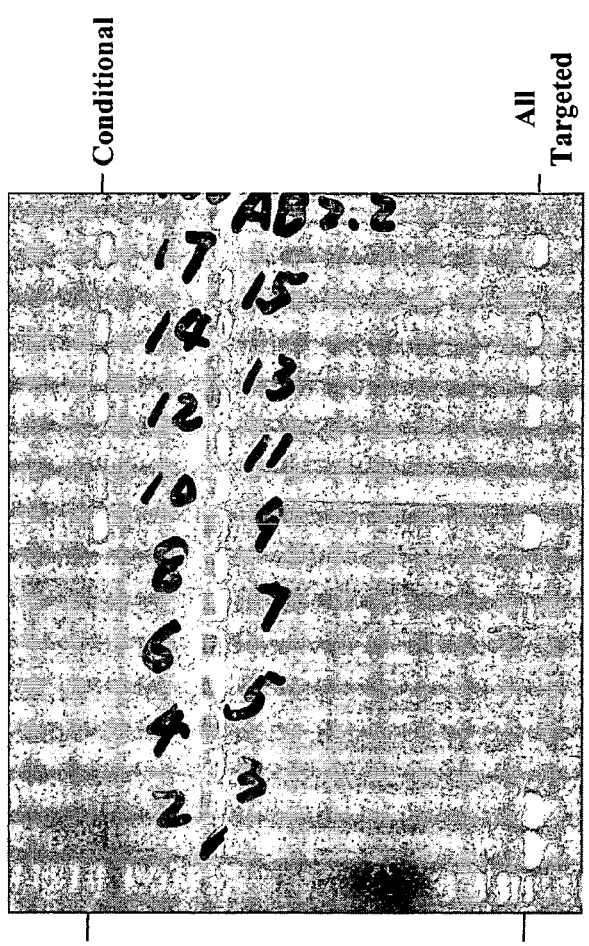
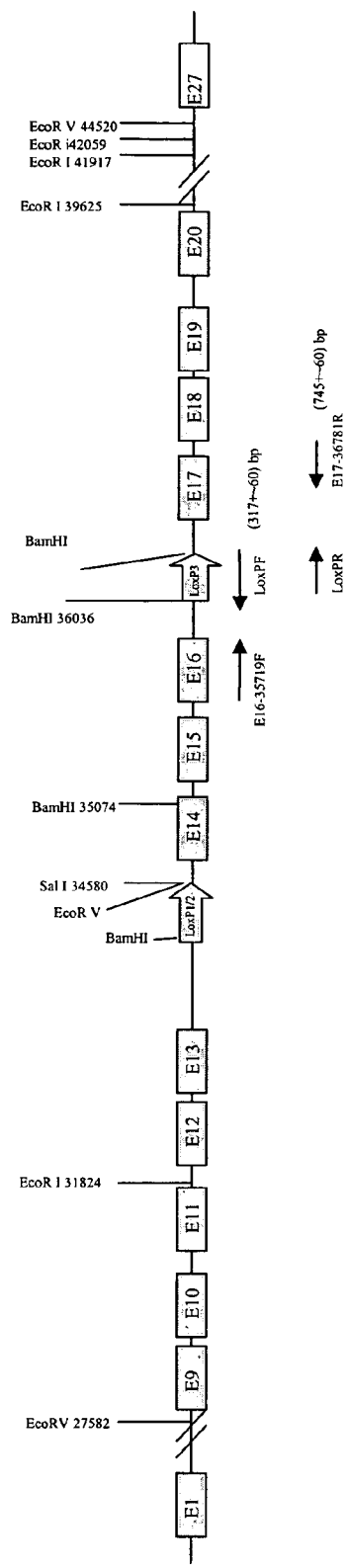
Figure 4

Figure 5A (SEQ ID NO: 1)
AATTCATTTTGATTAGATGTCGTTTAAAAGATGGGATGTAGCTGTGTTAGAACCCTGCCTCATAACGTGTGAGACCCTGATTCTATCCCAGCACTACCAAAGTTTAAAACAAA
TCGGAACAACTAGAAGGCTTGAAAGCTTGTTGGTATTTCAAACTAAAGTACTTGGTTGTGGCAGCTTGTTGGCAGAGGTTCTGAGTCTGCCCCGTGGCTG
GTAAACGTAATTGGGAAATGCTCTGTTCTGTCTTGTTTCAGGTCCACCGATGACAGTGTACGGTTGGCTGAAAGAGTGTAGCTCTCATTTGCTGTGAAAACTGCACAAAATTGGT
ATGTAAACATGCTTGGTCGGCTCACATTATCAGTGAAAACATTATCAGTGAGAAAAGGTGCCGTCAGGAGCACATGGAGCCTCGCGGGTTTCTGGGTTTGTCAGGGCCTAGACATGCTGCTT
TGACTATACCTCGGTCGGCTCACTATGCCTTTCTGTACCTCAGAGCCTTTCTGACTTTCACAGCTTCACTGTAAACAGCTGCCACTTTTTGCTTCT
GTTGTTGGCCCCTTTTACACACATAAGGATGCTCTAACTATTGGATTCTAAGGCCAGCCATATGTATGTTTAAATGTATGTTTAATGTATTAGACATGTATT
AATGTATTAGACTATGTCAGGTTAGGTTTGTTCATGCTGAATGCATGAGTGTCACGTGGAGGCAGATGAGGGCAGATGGGAACCTGGTTTGATATTTTAATTTT
GGATTTTAGAGTTAGGTTTGTTCATGCTGAATGCATGAGTGTCACGTGGAGGCAGATGAGTGTCAGTACTTTACAGTGTTTGTGAGGTTTATCATCCTATGTATGTGC
GCGGTTACTTGCACTGTGTGCCTGCCTGCCAGCAGCCAGTGTCTCCTCACTGCTGAGCCAGCTCTTTTCAGTGTCTCTAACGGCAGGGCCTTTGTGTCTCTCAGCATGTGGGTGCTCCCTCAGCATGTGCT
CTGGCTCCTCCGGAGCAGCCAGTGTCTCCTCACTGCTGAGCCAGCTCTTTTCAGTGTCTCTAACGGCAGGGCCTTTGTGTCTCTCAGCATGTGGGTGCTCCCTCAGCATGTGCT
CTTTAGATCATTTACTTCTTCAGGTTGCTGACATAAGCGCTTTAAACTCGTAGGTGAACTGGATGAACACTGGATGAACACTTGGGAAAGAGACTGTTAAATATGAAGAAGACGAAGCT
GGACTTACATGACGAGGAGAGACCAGTGTTCCCGGAGACCAGGTCTACCCCAAAGCAGTTAGTATTGCTTAGAACTGCTTCAGCGCGGACGCGCCTC
TCAGTTTATCCTCCGCCACATCACATGCACTCTCTGTCCAGACATCTTCTGCTCAGATGTTTCCCCAGTGCCCTCCTTGGCGTCTCAGAGCCGCTTTGTATT
TGAGCATAAACTGTGCTGGGCTCTGTTCGGTTTTGCTCATAAGCCCTTCTAGTGGCCCTTGCTAGCCTAGCCATGACCTCCACAGTTAGCGGGTGAATGAAAAGGTTGCTTTGCCGGGGGC
GGCACATTCTTTTATTTATTTAGTGGTGTGACTCTAGCCTTGCTGTGACCATGACCTCCACAGTTAGCGGGTGAATGAAAAGGTTGCTTTGCCGGGGGC
CGGGTCTGTCAGGAGATGGAGGAGGCTGTGCTGGAGGAGCTGTGCTGGAGAGTTCTTAGTGTTTTGTCTTCACCTTTGTTTTTGCAGTTTTACTTACGTATCGTACCCCAGCTAAGCAT
GACAGAGGCTGATCTTAAAACATGGATATTTTCCCTCCCAACCATTGTGTAAACCTTTGTGTAAAGCTTTCACCCTCAAGCTTACTTGGGTAACAGTGTAACTACCAGTGTAACTGTGAACCCCAACCTGTGAGTC
TTTTCAAGATTTAAAAGTCCTGCTTTCGCTGCCCCGTGACCCCATCCTGTCTTTCCCAACCCATCTTGTCTTAGTAGTCTTTGGGTAACAGTGTAACTGTGAACCCCAACCTGTGAGTC
CGTTCTGTCTTGCTCGCTGCCCCGTGACAAAATCTGAGAACCACATGTAGAGTAAGAATTACATTAGAGCCAGAGAGCTGGTTCAGCAGGCCTGAT
TGAGAAAGTTGAAAACTCCCCGAGAACCACATGTGAAGGTGATAGATAACACATGTGAAGGTGATAGATAACACATCTGTGTAGTAACTGGTGGTTAAGAATTACATTAGAGCCAGAGAGCTGGTTCAGCAGGCCTGAT
TGCTGGAGTTTTTAGTCCCCAGAGTATTAAAACTGACACTGATTTGCGAAAGGTTGTCCTGTAGTAACTGAGGCACAACAAACTGCTGTCTCCCTTTCTGTCCTTATGATTGGCCAAGACAATGTGATTTGTACCGTGAAA
GAGGTCATGAGTATTAAAACTGACACTGATTTGCGAAAGGTTGTCCTGTAGTAACTGAGGCACAAACAAATAAATTTTTCCCCCATTGGTGCCAAGACAATGTGATTTGTACCGTGAAA
CCCTCCTTTCCCTTGCACATTTACCTTAGCTAAGCTAGCATTGAATGAATTACCTAGAGTAGAGACATATTGAATTGAATTGAAGTTTAATACTAGAGTGATGGGTTATATACAATATTAAAACAAACAAAACAGATCGGTCGACGGTATCGATAAGCTTGA
AAGATTTTTTAATGAAATAGTTTTACAAATAGTAGAGCATATTGAATTGAATTGAAGTTTAATACTTCGTATAATGTATGCTATACGAAGTTATTAGGTCCCTCGACCTGCAGCCCAAGCTTGATATCGAATTCTA
TATCGAATTCGAGCTCGCCCGGGGATCCGGAACCCTTAATTAAGCCCCCTCTGAGAGCAGTCTGGGCCACTTGGCGCTGAAAGCATAATGTATGCTATACGAAGTTATTAGGTCCCTCGACCTGCAGCCCAAGCTTGATATCGAATTCTA
CCGGGTAGGGGAGGCGCTTTTCCCAAGGGGATCCCGGGAACCCTTAATTAACCCCCTCTGAGAGCAGTCTGGGCCACTTGGCGCTACACAAGTGGCCTCTGCGCACAAGTTCCACATCCACCG
GTAGGCGCAACCGGCTGCTCTTGTGCCGCCACCTTCGCGCCACCTTCGCGCCACCCTGAGCAATGAACCACCCCCCGCCAGCTCGTGCAGGACGTGACAAATG
GAAGTAGCACGTCTCACTAGTCTCGTGCAGATGGACAGCACCCGCTGAGCAATGGAAGCGGGTAGGCCTTTGGGGCAGCGGCCAATAGCAGCTTCGCTCCTCCTTCGCTTTCTGGGCTCA

Figure 5A (SEQ ID NO: 1, cont.)
GAGGCTGGGAAGGGTGGGTCCGGGGCGGGGCGGGGCTCAGGGGCGGGGGCTGACCTGCAGCCCAATATGGATCGGCCAGTTGACGACCAGCAGTTCTCCGGCCTTGGGTGGAGAGGCT
CCGGCGTGTTCTCCTCCTTCATCTCCGGCCTTTCAGCCCTGACCTGCAGCCCAATATGGATCGGCCAGTTGACACAGATGATTGCACGCAGTTCTCCGGCCTTGGGTGGAGAGGCT
ATCGGCTATGACTGGCACAACAGACAATCGGCTGTCTCTGGCCACGGCAGCCCGTGTTCCGGTTCTTTTGTCAAGACCGACCTGTCCGGTGCCTGA
ATGAACTGCAGGACGAGGCAGGCGCGCTATCGTGGCTGGCCACGACGGCGTTCCTTGCCGACGTTGTCGCAGCTGTGTCGACGTTGTCACTGAAGCGGGAAGGGACTGGCTGCTATTGGGCGAA
GTGCCGGGCAGGATCCTGTCATCGAGCGCATCGAGCGGCGATGATCGGACTGTACCTTGCTCTCTGCCGAGAAGTATCATCATGGCTGATCAGGATGATCTGGACGAAGAGCATCAGGGGCTCGCCAGCCGAACTGTTCGACCA
CAAGCGAAACATCGCATCGAGCGGCATCGGACGGGCATGCCGACGGCTATCAGGACGTTGGCTACCCGGTGATATTGCTGAAGAGCTTGGCGGCGATCAATTCTCTAGAAATGCGGAATGGCCGCTTCCTCGTGCTTACGGTATCGCCGCTCCGATTC
TCAAGGCGCATGCCGACGGCTATCAGGACGTTGGCTACCCGGTGATATTGCTGAAGAGCTTGGCGGCGATCAATTCTCTAGAAATGCGGAATGGCCGCTTCCTCGTGCTTACGGTATCGCCGCTCCGATTC
GGTGTGGCGGACCGCCTTTCTATCGCCTTCCTTGACCGTTGGCACGAGTTCTTTGACGAAGTGCCACTCGCATTGCATCGCATTGTCAGAAGCTGTCTAGGGAAGAACCAGCAGGCGGCTCCTCGAGTAGGCTCGAGAGCTCGAGATCGCGC
GCAGCGCATCGCCTTTCTATCGCCTTCCTTGACCGTTGGCACGAGTTCTTTGACGAAGTGCCACTCGCATTGCATCGCATTGTCAGAAGCTGTCTAGGGAAGAACCAGCAGGCGGCTCCTCGAGTAGGCTCGAGAGCTCGAGATCGCGC
CCTCCCCGTGCCTTCCTTGACCCTGGAAGGTGCCACTCGCATTGCATCGCATTGTCAGAAGCTGTCTAGGGAAGAACCAGCAGGCGGCTCCTCGAGTAGGCTCGAGAGCTCGAGATCGCGC
GTGGGCAGGACAGCAGGGAGGATTGGAAGACATAGCAGGCATGCCGGAAATCGGCCAACATAGCTTGATCTGGCCGGCCAACAGATAAGCTTGATTCGTCCGGCGCCAATATACAAAAGCCTCTCGTGTACCAGCAGAA
TTCTAGCCTCGAGGCTAGAGCGGTCCAGTTTGATCTGGGTCAGTTTGATCTGCCGGCCAACATAGCTTGATCTGGCCGGCCAACAGATAAGCTTGATTCGTCCGGCGCCAATATACAAAAGCCTCTCGTGTACCAGCAGAA
GGGCAGAGATGCGGTAGTCAGGTCCCCAGGCCATCCAAAAACCATGGGTCTGTCTGCGGCCCATGGGTGCGTTGACCTCGTGACAGTCGTTGGCTGCCGCCCGACGTTGCCTGGCTGGCTGGATGCGGCTCCCGAACTTGGGGGTCGTGCGC
CAGTACATGCGGTCCATGCGGTCCAGGCCATCCAAAAACCATGGGTCTGTCTGCGGCCCATGGGTGCGTTGACCTCGTGACAGTCGTTGGCTGCCGCCCGACGTTGCCTGGCTGGCTGGATGCGGCTCCCGAACTTGGGGGTCGTGCGC
TTCCCCATGGGAACGCGGGCGTCCCTAACCCACGGGCCCAATGGCGGTATTGCCGTCATAGCGGGTCTCGGTGGGTATCGTCCTTCCTGGGTATGTGTCTCCGCCACGAGTGCCAGCCTGACACGAGAGTGCCAGCAACGAACCCGGTGTGAATCATCTCCGCGGCAACTGGGGGCTGTAATCAGGTAAGCGACCCTGCAGATAGCGGATCACACCCAAACCAACCACGGGCCCAATTCCAAACCAACCCTCATCCCCGATCTCCGCGGTATCAGCTTCAGGATATAAAGACGTCA
GAAAGGAAGAAAACGCGGGCGTCCCTAACCCACGGGCCCAATGGCGGTATTGCCGTCATAGCGGGTCTCGGTGGGTATCGTCCTTCCTGGGTATGTGTCTCCGCCACGAGTGCCAGCAACGAACCCGGTGTGAATCATCTCCGCGGCAACTGGGGGCTGTAATCAGGTAAGCGACCCTGCAGATAGCGGATCACACCCAAACCAACCACGGGCCCAATTCCAAACCAACCCTCATCCCCGATCTCCGCGGTATCAGCTTCAGGATATAAAGACGTCA
TTTATTCTGTCTTTTTATTGCCGTCATAGCGGGTCTGGGTGTTCCTTCCGGATCATCTCCCGGGCAAACACGTTGTACAGGTGCGCGTTGGGGCGTCCCCAGAGGTAAAGCTGTCCCGCCCTCGACGACCCGTCGATGTGTCCCTGCGTTTGGCCAGGCGGTCATGCGGCGGGTAGCACAGGAGGCGTTGGCCATTGCCGGGACGTTGCTCGATTGTCTGGGACCGTCTATATAAACC
CGTCGGATATGGAGCGTTGGGCCGTCCGTTTGCCAAGACGTCAAGGCCTCGATCATCCCAGGCCAACACGTTGTACAGGTGCGCGTTGGGGCGTCCCCAGAGGTAAAGCTGTCCCGCCCTCGACGACCCGTCGATGTGTCCCTGCGTTTGGCCAGGCGGTCATGCGGCGGGTAGCACAGGAGGCGTTGGCCATTGCCGGGACGTTGCTCGATTGTCTGGGACCGTCTATATAAACC
TGGGACGGAGCGTTTGCCAAGACGTCAAGGCCTCGATCATCCCAGGCCAACACGTTGTACAGGTGCGCGTTGGGGCGTCCCCAGAGGTAAAGCTGTCCCGCCCTCGACGACCCGTCGATGTGTCCCTGCGTTTGGCCAGGCGGTCATGCGGCGGGTAGCACAGGAGGCGTTGGCCATTGCCGGGACGTTGCTCGATTGTCTGGGACCGTCTATATAAACC
TGGGGCTCGTGGGCCCGCGTTTGCTCGGGCTAAACGCGGGCAAGATCGGCGGGATGAGGGCCGGGATGGCCCAGCTCCCGCGTCCCCAGCTCCCACCCTGGTCAAGGCGGTTGCGCGAACCAGTGCCAACGCCGTCAACGCGCAGCCGTTGTCGAA
ATTGGCAAGCGATGTTTGTCCGGGCAAGATGAGGGTCGAAGATGAGGGTCGGGATGAGGGCCGGGATGGCCCAGCTCCCGCGTCCCCAGCTCCCACCCTGGTCAAGGCGGTTGCGCGAACCAGTGCCAACGCCGTCAACGCGCAGCCGTTGTCGAA
CCAACACGATGTTTGTCCGGGCAAGATGAGGGTCGAAGATGAGGGTCGGGATGAGGGCCGGGATGGCCCAGCTCCCGCGTCCCCAGCTCCCACCCTGGTCAAGGCGGTTGCGCGAACCAGTGCCAACGCCGTCAACGCGCAGCCGTTGTCGAA
GCGATGGGATGCGGTCGAAGATGAGGGTCGGGATGAGGGCCGGGATGGCCCAGCTCCCGCGTCCCCAGCTCCCACCCTGGTCAAGGCGGTTGCGCGAACCAGTGCCAACGCCGTCAACGCGCAGCCGTTGTCGAA
CATTGTTATCTGGGCGCTTGTCATTACAACCGCCCGGCGTCCCCGGCCGATATCTCACCCTGGTCAAGGCGGTTGCGCGAACCAGTGCCAACGCCGTCAACGCGCAGCCGTTGTCGAA
CCCGCCAGTAAGTCATCGGCGTCGGGATACGTAGACGATATCGTCGCGGAACCAGGCCACCAGGCCAGTTGCGCAACGCCAGTTGCGCAACGCCGTCAACGCGCAGCCGTTGTCGAA
CGCAGTAGCGCCGTGGGCATTTTCGCCCGGGCATCGAGAAGCCATACGCGCTTCTTACAAGCGCCTCACCTTGGCAGCTGCTGTTGAATTCGCCAATG
CGCAGAGCGCGTGCTGATGGCCGGGGTCGCTCGGGTGTTCGACATTGGTGAGCACGGGCTCCAAGCCCTTGAATTCGCCAATG
AAGCGGGTCGCTGCAGGGTCGCTCGGGTGTTCGACATTGGTGAGCACGGGCTCCAAGCCCTTGAATTCGCCAATG
ACAAGACGCTGGGGTGGAGAGGCTTTTTGCTCTCTGTTGCTCAGCTGTCACCACACACTGCTCGACACTGCTCGACTGCTCGACTTGGGTGGAAACATTC
CAGGCCTGGGTGGAGAGGCTTTTTGCTCTCTGTTGCTCAGCTGTCACCACACACTGCTCGACACTGCTCGACTGCTCGACTTGGGTGGAAACATTC
CCCTCGACCTGGGGTGGAGAGGCTTTTTGCTCTCTGTTGCTCAGCTGTCACCACACACTGCTCGACACTGCTCGACTGCTCGACTTGGGTGGAAACATTAGT
TGCTTTTTCAGTCAAAGAAATAGAGAAATAGATCAAATGATTTAAATGATTTAAAATACTGTAATAAACTGTAATAAACTGTAATAAACTGTAATAAACTGTAATAAACTGTAATAAACTGTAATAAACTGTAATAAACTGTAATAAACTGTGGGGCAGTGT

Figure 5A (SEQ ID NO: 1, cont.)

GCAGCTCTGGCTTCCCACGAGACTCGAGCTGAGTGCCTTCTGAGCTGCTGCTGCTTGTTTAACCCCACAACCAGAATAAATGTCTTTCTGCCAGCATCTAGAACAAAG
GCTGATTGTATTTGAGCATGATGCTTAATTCTTCTTCCAACTCTAGATTCCAGAGTGCTTGAGGAGAGTTACCCCAAACCCAGCCTTGTTACCTGTATGTGATAGGAATG
GTCTTAACTACCCCCTCCTGATGAACTCAACTTCAGGCGCCGGAAGCTCTACCCACCTGAGGACACCAAGATGCTTTGGGATCCTGACAGCCAAACCCATACTCAGTTAA
CCCTTCACCGAGTCTATTGACATAGGGATGGAGTAAGCTAATGTCATTGTGACTAAAGGTACCCACTCTTCTCTTTTGCTAAGATTCCTCCTGTGTATACACGCTCTGA
GAGGTCACCATATCCATCGAGCTGAAGAAGTCTGTTTCACATTGTGGTTTCAACAAATGCTCGAGCTGATTACAAGATGCACCAGTACAGAAGATTGCACCAGTACATATCTCCGGCTTGAGAA
GCCTGCCCTGGAGTTTAAACCTACAGGCGCGGAGTCAGCTCAGCCTCCCTCACTGTCTGTTCTACCCTGTCTTTAATGTTGGTAAGAAGGGCCTGCTGCCAGGGTGCTTTATCTGGCAGTGAGTGGTT
TGCTGGTGACTCACTCATTGTGTATCCACGAATCTCCTTTGGACATTGGACTGTAGACTCACATTAGTGTAGACTCAGATTGAAATCTCACCTATGTTATATTAACCTGTTAAAG
TGTTTTCTTCCTGAAGTTATTTAAGTTAGAAGATTCCACCAGATGCAGTGCTTTTAAATTCATGGAGGATATTGAGAAGTCGAAGCTCGATAGGCATTCCTAGCACCAAGTATTCAAAGG
AAACACCGTTGTCTTTTAAGGTGTCTCTCTACTCACGAAGTGTCTCTCTCTCTCCCTTAATTCCACACACATTTAAAACAATTCCAAAGGACACTGCAGCTGAGAGAGTTACATTG
TGGCTGTGCTGTGCACCATGTCTATATAAATAATGTTGCTAGCCTTTAAGAAGTGTCTCTCCTTTATTGTAGAAGGCAGAGAGAAGTCAAAATACATC
TGAAAAATATATTCTTATATAATGTATCCTATACGAAGTTATAAGCTTTCCCAGAGTCATTGTTACTCCGCCTGTGGAGGTGGGAAGGAACCACTTGACAGAGTCTCCTCTCCTACCCA
AAGCTTATAACTTCGTATATCAGATACCGCATATTTAACATGACTAACTAATTTGCAAAGGGACTACCTCTGTTGATTGCATTTCTGTTTGAAATGGAGAGCTTGTTTTACCAATTAAAATAGGATCCGCCATTGCAAAGGCCAGAGCCACAGACATGATA
TTCTATATCAGATACCGCATATTTAACATGACTAACTAATTTGCAAAGGGACTACCTCTGTTGATTGCATTTCTGTTTTACCCGAAATGGAGAGCTTGTTTTACCAATTAAAATAGGATCCGCCATTGCAAAGGCCAGAGCCACAGACATGATA
TTAGCTTTAAGATTATCAAAGGAAAGACATTTAGAAGAGAATAAGGCCTATATTCAATTGAACCTCAATGATGTGTTCCATATTAAAATACGATCTGTTACCCCACTCAGTAAATTTCCTTCCCTGAA
TTTTTGGAATTTAAATTCTCATTAATGCTATTACATTTGATCAGCCTCAATTTGATCTGATTTTATGTAGCTGATGTATATACGACTGTATATACGATCTGTTACTTGAGATAGTGTACTTGAGATAGTGAGTTACACAAAGG
CAACTTGATTAATTTCTTTATTTTGCAGAATATTATAAAACAAAGTATAACCTGACCTGACACTGAATAACCAGCCAATCTCAACCAGCCACACATCTTCAGGTAAGAGCCACAGATGATA
TATGAAACTTTTTGCAGAATATTATAAAACAAAGTATAACCTGACCTGACACTGAATAACCAGCCAATCTCAACCAGCCACACATCTTCAGGTAAGAGCCACAGATGATA
CTGAGGTTGCACAGGGGGGCTTGCTTTGGAGTTCTAACCAGTGGAGTTCTAACAGTGCTGAGAAGAGGAAGGCAAATGGAAAGTCTGCAGAACAAACAGGTAATGAGGTGCTAGTCACCGGACTAAGGGTTTA
GAATGTAGGCATACCTAAGTTGGAGTTCTAACCAGTGCTGAGAAGAGGAAGGCAAATGGAAAGTCTGCAGAACAAACAGGTAATGAGGTGCTAGTCACCGGACTAAGGGTTTA
TTGAATCAGAAGGGGAAAGCACTTCCTCTAAGCAGTGCTTTAGGGTTCTAACCAGTGCAGTGGAGTTCTAACCAGTGGAGTTCTAACCAGTGGTGAGTTCTAACCAGTGGAGTTCTAACCAGTGGAG
CATTGCTTCTTTAAGTTTGAGGTTATTATAATGACATCATTTCTCTTTCCTGCAAGCACTGCCGTGAGTTGAGAAGGTCGCCATGGTATTGAGTTACTTTG
CGTTTTCAATATGTACAGCCTGCTCAAGCATGACCTAATTTGAAGTTCAACATTATCAGTATAGCAATGACCTGTGAGTTAGGAAGGTCGCCATGGTATTGAGTTACTTTG
AACATCCTTGTTGGTAAAACTTGGGTTCCTGGCCACTGGTCTTTATATAGATTGCTTTGCTTTATATGATTTGCTTTTCTTACTCAGAGGAACTGCCTTCTGACCTGTCCTTCTGACTGCAGAGAATCCTGGTTCCGGAACTCTGTG
TACGATTTTCACCATGGTCCCTTAGTGAAGTTGGTTCTCTCCCCAGCAGTTTGTCTCCCAGCATACTGCCTTCACTCGCCTTCACTCGCCCCAGAGAACCTGCTTCTTTGACTGCAGAGGAACTGCTCAAGGAGCTCAGACAGCCAGCGAT
CTATACATCCAATCCAGCATCACTGTGGAGAAAAGCGTTTGTCTCCCAGCATACTGCCTTCACTCGCCTTCACTCGCCCCAGAGAACCTGCTCTTTGACTGCAGAGGAACTGCTCAAGGAGCTCAGACAGCCAGCGAT
GCTGGTGTGGGTGTCAGATCACTTCCCGTGATTTTAGGTATGCCTGTGTTTAGGTATGCCTGTGTTGCCAGAAATTTGATTTGCAACAAATGGAATTAAGTTAAAGTTGTATTTTCCTATATTT
CTAAAAGATGACAAGGACCATGTGCCCATTTAACACATGAAAAAGAAACTGTACTGTTAACACATGAAAAAGAAACTGTACTGTTATCCTGAAGTAGCAGACCATTGAGATCTTGTCAAGTTAGAGAGCAGCAAGCC
CCCTGAGACCGGATCATTGCTCCTGTAGCAGTGATGCTGAGAATAGGGTGAGAATGCGGATATAGTTCTTCAAAACTAACCTCATGTTAGCAGCAGCCTCCGCTCCTTCTTAT
TCTGGTCACTTTTTTCCTGTTAGTGAACGTCTGTATACAAAGAAATCTTTGTCATATAGATAGTTGGTCATATAGATAGTTGTAGAGTGGTTGTAGAGCATCTTAACATAGTAATG
TGAGCAATAGTCCCAGTTATCCTACCTGAGTACTTGATACAGTCTGCAACACAGGCTTAAACATGCTCTGTGCTCTATGCTCTGACATAGGATGTATTGATCTCATCTCCAAGAG

Figure 5A (SEQ ID NO: 1, cont.)
CAGAAATTGAGGCACAGAGAAAGTTTGTAAGTTGCAAGAAGCTGCTCACTTGGTTCAGGAGGTGAGCCCACTGCAGTAGCCAGTAGCCACTGCAGGACCTCCACGTTGGTCCTCTCAGT
CAGCTCTGCTTTGCCACCATAAACAGAAGTCAAAGCAGTAAGCTGTTCTGCATTAGAACCGACTGTGTGCAGAGTCCCAGGCCAGGTAAGCTTGGAAGTGCGTTTCTTCT
TAGGATGACTTTTAGAGTTGCTTGCTTTGTTGCTTTAACTCAAAGTGTTGCTTTTCTGAGCTGTCTTTGGAGGGTTGAAAGAAAGTTATAAAAATGTCTTTGCAGATACCCT
AACTTAGACTTCGGGTGGAAAAAAATCTATTGATAGCAAGTCTTTCATCTCAAGCTGTAACTCCTCGTTGCTGAGAGTGATAATTACTGTAAGCACAGCACAACTGTAGTCCCTGA
ACATGCTGCACATCAAGGTGCTACTAGACCCTCCTTAGAAAACCATGACCAAATGTCTGTGAACTGCAAAAGGTTGCCCGCTGTAAGCTCCAAAGTGAGGTTTCAA
CGGATCTTACAGCAATTAATGGTCTTTTCTTACAATAAAAACCTTGCCAATGCAGTTATGATTTAGTTAACAGAGACTTTGCCAAGGAAATCAGCTGAATTACTTCAAGCAGGAA
ATACCTGTACAACCAACTACCTCAGATCCATTCAGAATTTGTACAATTATGAGAACCAGCCCAGCACTCAAGGACTCTGACAGGATGACTTCGAGCAGAGCCCTTCTGTTGGGTACT
TAACACATCTACCTCAGATGGAGCCCCATCGGGACTGATTCTCCAGGCTTTGACACTGTCAAATGCCAGTGATGGGTTTAACCTGAGCGGCTTGGCGACTCCTTTTTAAAG
CCTCAAGGACTCTTGGCCCCAATCGGGGACTGATTCTCCAGGCTTTGCACGTACCCTGATGCTCATGAAGGCGCGCCTTTCATATATGAGAAGCAAAAGGTAAGGCACGATTCTCGTTCTGGGCTGTGCTCTTCA
CATGCTATCACCACATATCTGTTTTGCAGTTACCCAGTTACCCATGGGAATT
GTGTGCCTGAAAACAGGCCAAGTTACCCATGGGAATT

Figure 5B (SEQ ID NO: 2)

```
ATAACTTCGTATAATGTATGCTATACGAAGTTATTAGGTCCCCTGACCTGCAGCCCAAGCTTGATATCGAATTCTACCGGGTAGGGGAGGCGCTTTCTCCAAGGCAGTCTGGAGCA
TGCGCTTTAGCAGCCCCGCTGGGCACTTGGCGCTACACAAGTGGCCTCTGGCCTCCGCACACATTCCACATTCCACCGGTAGGCGCCAACCGGCTCCGTTCTTTGTGGCCCCTTGC
GCCACCTTCTACTCCTCCCCCGGAGTCGAAGTTCCCCCGCGCTCGCGTCGTGCAGGACGTGACAAATGAAGTAGCACGTCTCACTAGTCTCGTGCAGATGACAGCA
CCGCTGAGCAATGGAAGCGGGTAGGCCTTTGGGCAGCGGCCAATAGCAGCTTTGCTCCTTGCTCTTCGCCTTTGACTCTGCCGCGCTTGCAGAGCTCGGAAGGGGTGGTCCGGGGCGGGCTCAGGGAC
GGGCTCAGGGGCGGGGCGGGCGCCGAAGTCCCTCCGGAGGCCCGAAGTTCTGCACGCATTCTGACGCTTCAAAAGCGCACGTCTGCGCGCTTGGGGTGGCTATTCGGCTATGACTGGGCACAACAGACAATCGGCTGTCT
CTGCAGCCAATATGGGATCGGCGTGTCCGGCTGCAGCGGCGAGCAGCTGCAGCAGCCGCCATTGAACAAGATGGATTGCACGCAGGTTCTCCGGGTCTATGACTGGGCACAACAGACAATCGGCTGTCT
GATGCCGCCGTGTTCCTTGCCAGCTGTCAGCGCAGGGGCGCCCCGGTTCTTTTGCTACTGAAGCGGGAAGGGACTGGCTGTCATTGGGCGAAGTGCCGGGCAGATCTCCTGTCATCCACCTTGCTCTG
CACGACGGGCGTTCCTTGCCAGCGTGTGATGCAATGCGGCGGTCGACATACGCTTGAAGCGGGAAGGGACTGGCTGCTATTGGGCAATTCGACCACCAAGCGAAACATGCATCGAGCGACACGTACTCGGATG
CCGAGAAAGTATCCATCATGGCTGATCAGGATGATCTCGACGAAGAGCATCAGGGGCTCGGCCAGCAGCTGTTCGCAGCCGAACTGTTCGCAGCCTGGGGTCAGGCTCAAGGCGCCTATCTCTGTGAC
GAAGCCGGTCTCTTGCCTGCTTGCGAAGAGCTCGATCAGGATGTGGAATGCGGCGTCGAGAAAATGCGCCTTCCTCGTGCCTTCTGAGTAGTTGTATCAGGTATCATTCATGGTATGCCAGCGACATCTGTTGTTGCCCCTGACCCTTCTTCGCCTTCTCAACACCCTTGACGAGCTTCTC
TGAGGGATCAATTCTCTAATAAAATGAGGAAATTGCATCGCATTGGTTCTGAGGCGGAACCAGTGCCCTGTCTTTCTATGGCTCAGCTAGTCGTCCGAGATCATCAGCAGCGACGGGGTGAGCTCCTAGTTCTAGCTGACGATAAGCTTG
GCAGGCATGCGGGGATCCCGCGGAAACTCGGCTGGGTGTTTTGGGGCTGACCCGTTGTCGCGCGTAGGAGAGGCGTAGGAGGTCAGGATACATGCGGTCAGGTCCGCCGAAGATGCGGTCAGGCCCATCCAAAACCATG
ATCTGCCCAGAAATCCGGCGGTGTTCGCAGCGCGGAATCTGGCGGACTCGACCCCACGCGTTGTCGCAGCCAACGCCCTCCAGCGGGCTGAGCGAACCTTGGGGAAAGGAAGAAACGCGGGCTATTGCCGTCCTAACCCACGGGCCCGT
GGTCTGTCTGTCAGTGCAGGGCCTGCGCGCCCGACGTTGGCTGGACGGGGAAAAGATGGAAGAACGCGGGCTATTGCCGTCCTAACCCACGGGCCCGT
GGCTATGGCAGGGTATCGACAGAGTGCCAGCCCTGGGACCCCGGAACCTGGCCAGCCCTGGGACCCGTTTATGAACAAACGTGCGCCAGGTCGCGAGATCGTCGGTATGGAGCCGTTGGCGGTCTGACGTGGGTCTGATC
TTCCGGTATTGTCTCCTTCCGTGTTTCAGTTAGCCTCCAGTTAGCCTCCCGGCAGTTGGTCGTAATCAGGTCAGGATAAACGTGTCCCGATATGGGTCGTGGCCCGGTCCTCCAGGCCGTTGCTCTGGGCCTCGGCACCCT
ATCCCGGAGGTAAGTTGCAGCAGGTGCCCGTTGGGGGTCCGGAAAGCTGTCCCCAGGAGCAACTGTCCCCAATCTCCCGCCAGTGTCTGCAGATCAGGCTGCCCCCTGCTGTCTCCTCCGGATCGCCGGCAAGATCGGCGGCGATGAG
AAACACGTTGTACAGGTCGCCCGTCCCCGAAAGCTGTCCCCGGCGCGCTCGGGCCCGCTGGGCGCTGGCCCGGCAAGCTGTCCCCCCAACACGGGCGGCGATGGATGGCGGCAAGATGAGGGCGGGGCGGGG
GGGGCCCACACGCCCGCTCAAGCCCGTCAAGGCGGTTGTTGTGTGGTGGGCGCCCGGCGTCGCGGCCCAGCCTGGGGGCGGGATACGCCAGGGGCGGGGCGGGTCAGGGACCGATACGCCAGGGCGTCC
CCGGCCGATATCTCACCCTGTCAAGGCGGTTGTTGTGTGGTGGGTCTGGTTTTCCCCACTCCGTTGCCGCAGTCTGCGGACCGTCCATCCCGTGGCCGGGACCGTCGATTGTCTGGGACCGTCGATTGTCTGGGACCGTCCCGAAGCCAATCGGCTCGGGCCGGCTCGGAAAAGCCATCGCTCCGGGGACTTCCG
GTCGCGCGAACCAGGGGAACCAGGGCGCAACGCAGTTGCGCAACGCCTGTTGCGAACGCCGTCCAACGCCGCACGGCCGGACGAGCCAGCGAGCCGAGGAAGCCAGCGAGGCACACGCCTGGGGTACGAAGCCATAGC
TGGCTTCTTGCTGCCGGAGGGCCACCAGGCAGTTGCGCAACGCAGTTGCGCAACGCCGTCCAATAGCCCAGTGACCTGGGGTGCTGTTAAGGCGGTCGCTGAGGGTCGCTGTTCGGAGGCGCACACGCCACA
```

Figure 5B (SEQ ID NO: 2, cont.)
CGCGTCACCTTAATATGCGAAGTGGACCTGGGACCGCGCGCCCCGACTGCATCTGCGTGTTCGAATTCGCCAATGACAAGACGCTGGGCGGGGTTTGCTCGACATTGGGTGGAAA
CATTCCAGGCCTGGGTGGGAGAGGCTTTTGCTTCTCCTCTTGCAAAACCACACTGCTCGACATTGGGTGGAAACATTCCAGGCCTGGGTGGAGAGGCTTTTGCTTCCTCTTGAAAAC
CACACTGCTCTAGAGGATCCGGAACCCTTAATATTAACTTCGTATAATGTATGCTATACGAAGTTATTAGGTCCCTCGACCCTGCAGCCCGGGGATCCACTAGTTCTAGAGC
GGCCGCGTCGACACTCACCTTTATTTCTGATATTCTGTGTAGTAATAGTTTGAAAACTCACGGAATAAAAATGCTTTTCAGTCAAAAGAAATAGATCAAATGATTAATAT
TTAAAAGGCTCTATTTTAAATACTTTGTTTAACCCACACAGAAATAAATGTCTTTTCTTGCCAGCATCTAGAACAAAGGCTGATTGTATTGATAGGAGTCTTAATTCTTCTTCCA
CTGAGCTGCTGCTCAGAGTGCTTGAGGGAGAGTTACCCAGAGACACCACCAAGATGCTTTGGGATCCTGACACGCCAAACCCATGTCTTAACTACCCCCTCCTGATGAACTCAACTTCAGGC
ACTCTAGATTCCAGAGTGCTTACCCACCTGAGGACACCACCAAGATGCTTTGGGATCCTGACACGCCAAACCCATGTCTTAACTACCCCCTCCTGATGAACTCAACTTCAGGC
GGCGGAAGCTCTACCCACTCGATTACAAGATTGCACCAGTACAGACGCTCTCCACATATTCTCCGGCTGATCAAGCCTCTTCCAGAGAGCCATGAGGTTTAAACTCACAGGCGCGGAGTCAGC
ATGTCATTGTCTCAACAAATGCTCACCTCTTAATGTGTCGAGCTGATTACAAGATTGCACCAGTACAGAACGCTCTCCACATATTCTCCGGCTGTGACTGAGTTTAAACTCACAGGCGCGGAGTCAGC
CATTGTCTCAACAAATGCTCACCTCTTAATGTGTCGAGCTGATTACAAGATTGCACCAGTACAGACGCTCTCCACATATTCTCCGGCTGTGACTCACTCATTGTATCCCACGAATCCTCCT
TACTGTGTCTCTTAATGTCTCGAGCTGATTACAAGATTGCACCAGTACAGACGCTCTCCACATATTCTCCGGCTGTGACTCACTCATTGTATCCCACGAATCCTCCT
TACTTCACTAGCTGTAGACTCACATTAGTGTAGGATATTGAGAAGGTCGTACCTTAAATGAAATCTCACCTATGTATATTTAACCGTATATTTTAACGGAAACACCCGTTTGCTTTAAGTTAGAAGATTACCAAGATGC
ATTGACTTTAAATTCATGAGGATATTGAGAAGGTCGAAGCTCGGATAGCATTCCTGGACTTGCTTGTCATTGTGCCTGTGTCATTGTGCACCATGCCAGCATGCAGAGGGC
AGTGATCATTCAAGGTGGTGTTTCAGTGGGAACATTTAAACAATTCCAAAGAGCACTGCAGCTGAGAGAGTTACATTGTGAAAAATATTATTCTTATATAAATAATAATGTTGCTA
GCCTTTTAAGAAGTCTCTCTCTTCCTCCCTTAATTCCAAAGTCTTCCTGGAGAATTCATTGGGGAGAATGTGTGCCTTAAGCTTATAACTTCGTATAATGTATGCTATACGAAGTTAT

Figure 6
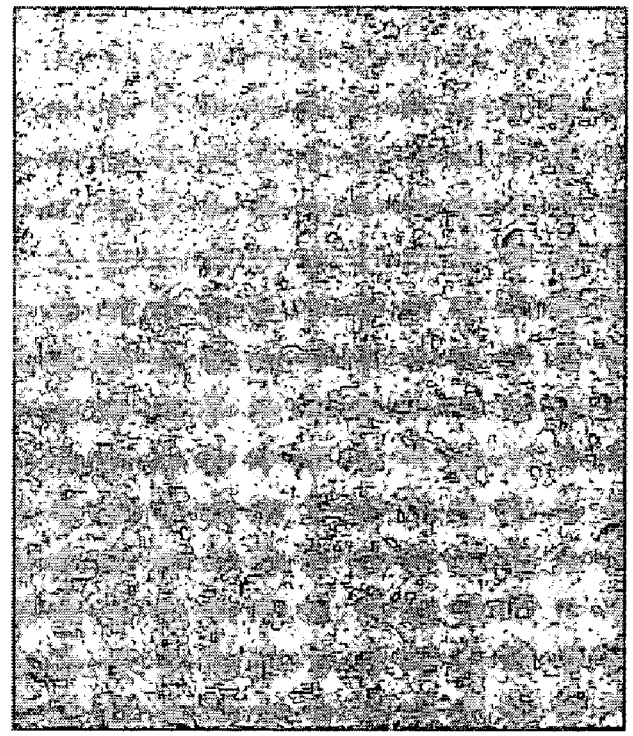
Adenovirus-Cre-Infected
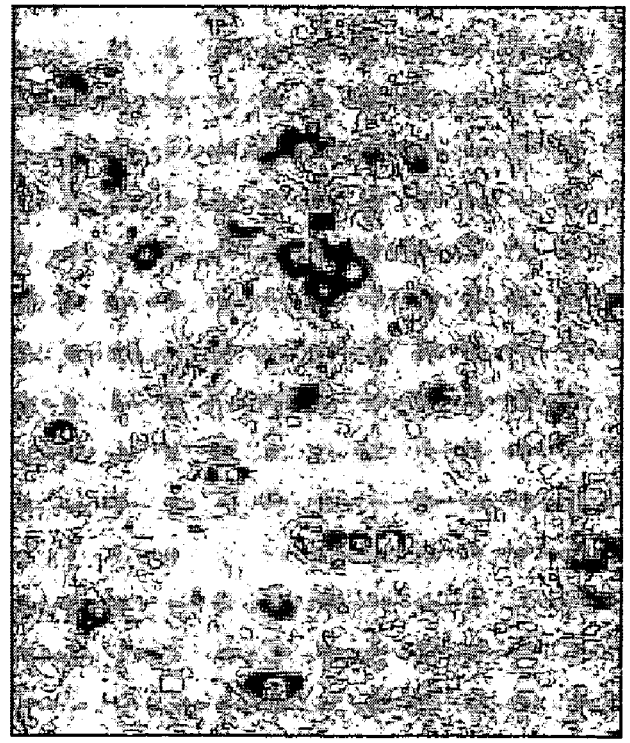
Mock-Infected
Dicer-Conditional MEFs

CONDITIONAL DISRUPTION OF DICER1 IN CELL LINES AND NON-HUMAN MAMMALS

RELATED APPLICATIONS

This application claims the benefit of prior-filed U.S. Provisional Patent Application Ser. No. 60/591,268, filed Jul. 26, 2004, entitled "Conditional Disruption of Dicer1 in Cell Lines and Non-Human Mammals." The content of the referenced application is incorporated herein by reference.

STATEMENT AS TO FEDERALLY SPONSORED RESEARCH

Funding for the work described herein was at least in part provided by the federal government (N.I.H. grants R01 CA77735 and R01 CA95216).

BACKGROUND OF THE INVENTION

In recent years, numerous experiments performed in a variety of model organisms have uncovered the cellular process of RNA-induced silencing. In this process, double-stranded RNA or some other form of RNA acts as a trigger for highly sequence-specific silencing of gene expression. To date, research efforts have achieved an improved understanding of the molecular mechanisms active in the RNA-induced silencing process of RNA interference (RNAi), but very little is known about the role(s) that RNAi plays in, e.g., development and disease-related processes in complex multicellular organisms.

The RNAi pathway has been robustly conserved in evolution, and initiates RNA silencing by utilizing double-stranded RNAs that are cleaved into short 21-23 nt dsRNA molecules by a cellular enzyme known as Dicer. The short dsRNA generated by Dicer cleavage are incorporated into a large multi-protein complex known as the RNA-induced silencing complex, or RISC. RISC then utilizes the short, sequence-specific RNA generated by Dicer cleavage to target and silence homologous RNA transcripts, thereby silencing the gene. As Dicer is a key enzyme in this process, a great deal of research interest in Dicer biochemistry and in the role of Dicer in this process has ensued. Dicer has been purified, and recombinant forms of this enzyme that can process dsRNA into siRNA in vitro are commercially available.

In addition to its role in generating siRNA, Dicer has also been found to generate another class of small RNA molecules referred to as microRNA (miRNA). The miRNA molecules are derived from slightly larger (~70 nt) endogenous, non-coding RNA containing many secondary structures, including stem loops and bulges. Unlike siRNAs, the miRNAs are not perfectly complementary in sequence to their RNA targets, and those directed to mRNA targets have been demonstrated to act by complexing with the 3' untranslated region (3' UTR) of their target message to inhibit translation. Several experiments have suggested that these miRNAs play a role in nematode development, as mutations in miRNA induce developmental defects in nematodes. Dicer has therefore been speculated to play a developmental role in higher eukaryotes, possibly through regulation of miRNA generation.

Although a recent publication has revealed that mouse embryos homozygous for a dicer1 mutant allele die for unclear reasons prior to gastrulation (Bernstein et al. *Nature Genetics* 35:215-217), improved tools are required to ascertain the role of Dicer in processes such as embryonic development, tissue-specific development, disease-related processes, etc., especially in organisms of greater complexity than nematodes.

SUMMARY OF THE INVENTION

The present invention is based, at least in part, on the generation of viable non-human animals that contain a synthetic conditional allele of the Dicer1 gene. The functional significance of Dicer in a wide range of tissues and at several timepoints throughout development may now be assessed through use of the constructs, methods, animals and cell lines of the instant invention. Animals, tissues, cell lines, etc. containing conditional alleles of Dicer1 additionally provide a valuable tool for drug discovery studies, especially those that involve testing of nucleotide, peptide and small molecule drugs directed against or reliant upon activities of the RNAi pathway.

Accordingly, one aspect of the instant invention features a recombinant vector comprising sites of inducible recombination that flank a nucleic acid sequence containing at least one exon of vertebrate Dicer1 genomic sequence.

In one embodiment, the recombinant vector features sites of inducible recombination that flank Dicer1 exons encoding for a PAZ domain.

In certain embodiments, the recombinant vector comprises sites of inducible recombination that flank a nucleic acid sequence containing at least one exon of mouse Dicer1. In other embodiments, the recombinant vector features sites of inducible recombination that flank a nucleic acid sequence containing at least one exon of exons 1 through 20 of mouse Dicer1. In additional embodiments, the recombinant vector comprises sites of inducible recombination that flank a nucleic acid sequence comprising at least one exon of mouse Dicer1 exons 14, 15, or 16. In other related embodiments, the recombinant vector comprises sites of inducible recombination that flank a nucleic acid sequence comprising mouse Dicer1 exons 14, 15, or 16. In still further embodiments, the recombinant vector comprises sites of inducible recombination that flank a nucleic acid sequence comprising a sequence of at least 20 nucleotides in length that is greater than 80% identical to the sequence of mouse Dicer1 exons 14, 15, and 16 or portions thereof. In certain related embodiments, the percent identity is determined across a portion of at least 30, 50, 80, 100, 200 or 500 nucleotides, and further may be determined across the full-length of the exon or exons.

In other embodiments, the recombinant vector of the instant invention additionally comprises at least one operably linked selectable marker cassette that is flanked by sites of inducible recombination. In a related embodiment, the recombinant vector comprises a first nucleotide sequence domain comprising two recombinase target sites that flank a sequence of at least 20 nucleotides in length that is greater than 80% identical to the sequence of mammalian Dicer1 exons 14, 15, and 16 or portions thereof; and a second polynucleotide sequence containing a marker cassette comprising, in operable combination, recombinase target sites that flank a polynucleotide sequence encoding for a marker. The first nucleotide sequence may be located either 5' or 3' of the marker cassette.

In other embodiments of the instant invention, the recombinant vector additionally comprises nucleic acid sequences flanking the sites of inducible recombination, wherein the flanking sequence is homologous to a genomic Dicer1 sequence and is capable of directing homologous recombination when the recombinant vector is introduced into a cell.

In some embodiments, the flanking nucleic acid sequence of the the recombinant vector comprises, on one flank, a sequence of greater than 80% identity to the genomic sequence located within 5 kb upstream (5') of the Dicer1 exon(s) that are flanked by sites of inducible recombination within the recombinant vector, and, on the other flank, a sequence of greater than 80% identity to the genomic sequence located within 5 kb downstream (3') of the Dicer1 exon(s) that are flanked by sites of inducible recombination within the recombinant vector. In other related embodiments, the flanking nucleic acid sequence of the recombinant vector comprises, on one flank, a sequence of at least 20 nucleotides in length greater than 80% identical to the mouse Dicer1 E13-E14 intron or portions thereof, positioned immediately 5' of a site of inducible recombination, and additionally comprises a sequence of at least 20 nucleotides in length greater than 80% identical to the mouse Dicer1 E16-E17 intron or portions thereof, positioned immediately 3' of a site of inducible recombination.

In additional embodiments, the recombinant vector of the instant invention comprises nucleic acid sequence that flanks sites of inducible recombination, wherein said flanking nucleic acid sequence comprises, on one flank, a sequence of at least 20 nucleotides in length of greater than 80% identity to genomic sequence located within 5 kb upstream (5') of Dicer1 exon 14, and, on the other flank, a sequence of at least 20 nucleotides in length of greater than 80% identity to genomic sequence located within 5 kb downstream (3') of Dicer1 exon 16. In related embodiments, the sequences flanking sites of inducible recombination are capable of directing homologous recombination when the recombinant vector is introduced into a cell.

In one embodiment, the recombinant vector comprises sequence SEQ ID NO:1. In another embodiment, the recombinant vector comprises sequence SEQ ID NO: 2.

In certain embodiments, the sites of inducible recombination of the recombinant vector are lox sites. In related embodiments, the sites of inducible recombination are loxP sites.

In some embodiments of the instant invention, the recombinant vector is operably linked to a marker cassette comprising neomycin phosphotransferase. In a related embodiment, the recombinant vector is operably linked to a marker cassette comprising thymidine kinase.

In other embodiments, the recombinant vector is propagated as a component of an autonomously replicating vector.

Additional aspects of the instant invention feature a cell or cell line comprising the recombinant vector of the instant invention. In related embodiments, the recombinant vector is genomically integrated into the cell or cell line of the invention. In an additional embodiment, recombination at the Dicer1 conditional allele of the cell or cell line is induced by exposure to a recombinase. In another embodiment, recombination at the Dicer1 conditional allele of the cell or cell line is induced by expression of a recombinase. In a related embodiment, exposure to the Cre recombinase induces recombination at the Dicer1 conditional allele in the cell or cell line of the instant invention. In an additional embodiment, expression of the Cre recombinase induces recombination at the Dicer1 conditional allele in the cell or cell line.

In another embodiment, the cell or cell line contains sites of inducible recombination that flank at least one exon of at least one genomic Dicer1 allele. In other embodiments, the cell or cell line of the invention contains at least one genomic Dicer1 allele from which at least one exon has been removed and that additionally comprises at least one site of inducible recombination. In additional embodiments, a diploid cell or cell line is disrupted for Dicer1 exons 14-16 at both genomic alleles of Dicer1, wherein both Dicer1 genomic sequences contain exons 1-13 of Dicer1 and at least one site of inducible recombination.

Another embodiment features a diploid cell or cell line conditionally disrupted for at least one genomic allele of Dicer1. An additional embodiment features a transgenic cell or cell line, wherein administration or inducible expression of an agent or performance of a state change causes an irreversible reduction in Dicer activity through genetic rearrangement of the Dicer1 locus. In certain embodiments, the cell or cell line of the instant invention is of human origin. In additional embodiments, the cell or cell line is an embryonic stem (ES) cell or cell line.

One additional aspect of the instant invention features the method of inducibly disrupting at least one genomic allele of Dicer1 for exons 14 through 16 in a cell or cell line. The method involves exposing the cell or cell lines of the instant invention to a Dicer1 knockout inducing agent, such that at least one genomic allele of Dicer1 is disrupted for exons 14 through 16 in the cell or cell line.

In an additional aspect, the invention features a non-human mammal whose genome comprises at least one conditional allele of Dicer1 at the genomic position of the endogenous Dicer1 gene, wherein the conditional allele is produced by insertion of heterologous DNA sequences comprising at least two sites of inducible recombination that flank at least one exon of the Dicer1 gene. In additional embodiments, the non-human mammal contains a recombinant vector or portion thereof of the instant invention. In related embodiments, the non-human mammal is homozygous for a conditional allele of Dicer1. In other embodiments, the non-human mammal contains an engineered conditional allele of Dicer1 at each of the two genomic alleles of the endogenous Dicer1 gene.

In certain embodiments, the non-human mammal is a mouse. In related embodiments, the mouse contains inducible recombination sites flanking exons 14 through 16 of the Dicer1 gene. In other embodiments, the genome of the mouse contains at least one Dicer1 allele comprising a disruption of the Dicer1 allele between exons 14-16 and at least one site of inducible recombination.

In additional embodiments, at least one conditional allele of Dicer1 is transmitted through the germline of the non-human mammal of the invention.

Certain aspects of the invention feature a method of producing a non-human mammal that not only contains a conditional allele of Dicer1 capable of germline transmission, but additionally contains a gene capable of expressing a Dicer1 knockout inducing agent. The method involves mating the non-human animal containing a conditional allele of Dicer1 with a non-human animal that contains a gene capable of expressing a Dicer1 knockout inducing agent and selecting offspring, such that selected offspring contain at least one conditional allele of Dicer1 and a gene capable of expressing a Dicer1 knockout inducing agent. In certain embodiments, the Dicer1 knockout inducing agent is a recombinase. In additional embodiments, the Dicer1 knockout inducing agent is Cre recombinase.

Related aspects of the instant invention feature the non-human mammal produced by the method of mating a conditional Dicer1 non-human mammal (e.g., mouse) with a non-human mammal expressing a Dicer1 knockout inducing agent and selecting offspring, such that selected offspring contain at least one conditional allele of Dicer1 and a gene capable of expressing a Dicer1 knockout inducing agent. In certain embodiments, the non-human mammal comprises a tissue-specific disruption of the Dicer1 allele.

Additional embodiments feature a non-human mammal transgenic for at least one Dicer1 allele, wherein administration or inducible expression of an agent or performance of a state change causes an irreversible reduction in Dicer activity in at least one cell type of the non-human mammal, through a genetic rearrangement of the Dicer1 locus in at least one cell type of the non-human mammal.

Another embodiment features a non-human mammal whose genome comprises a homozygous conditional disruption of Dicer1 that replaces the endogenous Dicer1 gene, wherein the conditional disruption is produced by insertion of a heterologous DNA sequence, wherein the non-human mammal exhibits Dicer levels and activities that are substantially normal in the absence of a Dicer1 knockout inducing agent, and Dicer levels and/or activities that are substantially decreased as compared to a wild-type mouse in the presence of a Dicer1 knockout inducing agent.

Other embodiments feature a non-human mammal that is conditionally disrupted for Dicer1 in a temporal- or tissue-specific manner. In additional embodiments, the non-human mammal is mosaic for a Dicer1 disruption. In certain embodiments, all tissues of the non-human mammal of the instant invention, except for those tissues that do not express a Dicer1 knockout inducing agent, are disrupted for Dicer1.

In other related embodiments, the disrupted Dicer1 allele of the non-human mammal of the invention lacks at least one exon of Dicer1 exons 14-16.

A related aspect of the instant invention features a cell line derived from any of the non-human mammals of the instant invention.

Another aspect of the instant invention features a method of testing the efficacy of a compound in a cell, cell line or non-human animal of the instant invention. The method comprises administering the test compound to the cell, cell line, or non-human animal of the instant invention, and comparing a response of the cell, cell line, or non-human animal to the test compound with the response of an appropriate control to the test compound, such that the efficacy of a compound in the cell, cell line, or non-human animal of the instant invention is tested. In certain embodiments, the test compound is an RNA silencing agent. In other embodiments, the test compound is an RNA silencing inhibitory agent. In additional embodiments, a potential cancer treatment is tested. In other embodiments, a potential treatment for Spinal Muscular Atrophy (SMA) is tested.

An additional aspect of the instant invention features a method for identification of miRNAs involved in adipocyte development/differentiation comprising administration of an siRNA agent that targets a miRNA target to a Dicer-null or Dicer conditional cell or cell line and assaying for differentiation in the siRNA-treated cell or cell line.

BRIEF DESCRIPTION OF THE DRAWINGS

FIG. 3A depicts a schematic diagram of the genomically integrated conditional Dicer1 allele following removal of a neo/tk selectable marker cassette, but still containing loxP sites of inducible recombination that flank sequence for Dicer1 exons 14, 15 and 16. FIG. 3B presents results of Southern blots performed on ES cell clones following administration of Cre recombinase (which induced excision of integrated targeting vector sequence encoding for selectable markers) and FIAU selection against cells containing the thymidine kinase (tk) selectable marker cassette, using probes as indicated in the schematic diagram. Asterisked cells indicate those cell lines of the instant invention used for injection.

FIG. 4 displays results of a polymerase chain reaction (PCR) test that confirmed the successful generation of mice containing a conditional Dicer1 allele (possessing structure as indicated in FIG. 3A and in the schematic diagram below PCR assay results). Locations of primers and lengths of amplification products for PCR assays are as indicated in the schematic diagram.

FIG. 5A depicts the insert sequence of the targeting vector containing the Dicer1 conditional allele. Dicer1 exons 9-17 are underlined and loxP sequences are shaded (SEQ ID NO: 1). FIG. 5B displays those sequences of the construct that are flanked by loxP sites (shaded). These sequences are targeted for deletion by Cre-induced recombination events (SEQ ID NO: 2).

FIG. 6 shows that Dicer activity was required for adipogenesis of Dicer-conditional MEFs (mouse embryonic fibroblasts). MEFs lacking Dicer due to Cre-mediated excision of the conditional alleles failed to differentiate (right panel, cells show no Oil Red O (ORO) lipid staining that would indicate differentiated adipocytes), whereas conditional cells that were mock Cre-treated displayed differentiated cells (left panel, cells stained with ORO).

DETAILED DESCRIPTION OF THE INVENTION

Figure 1:
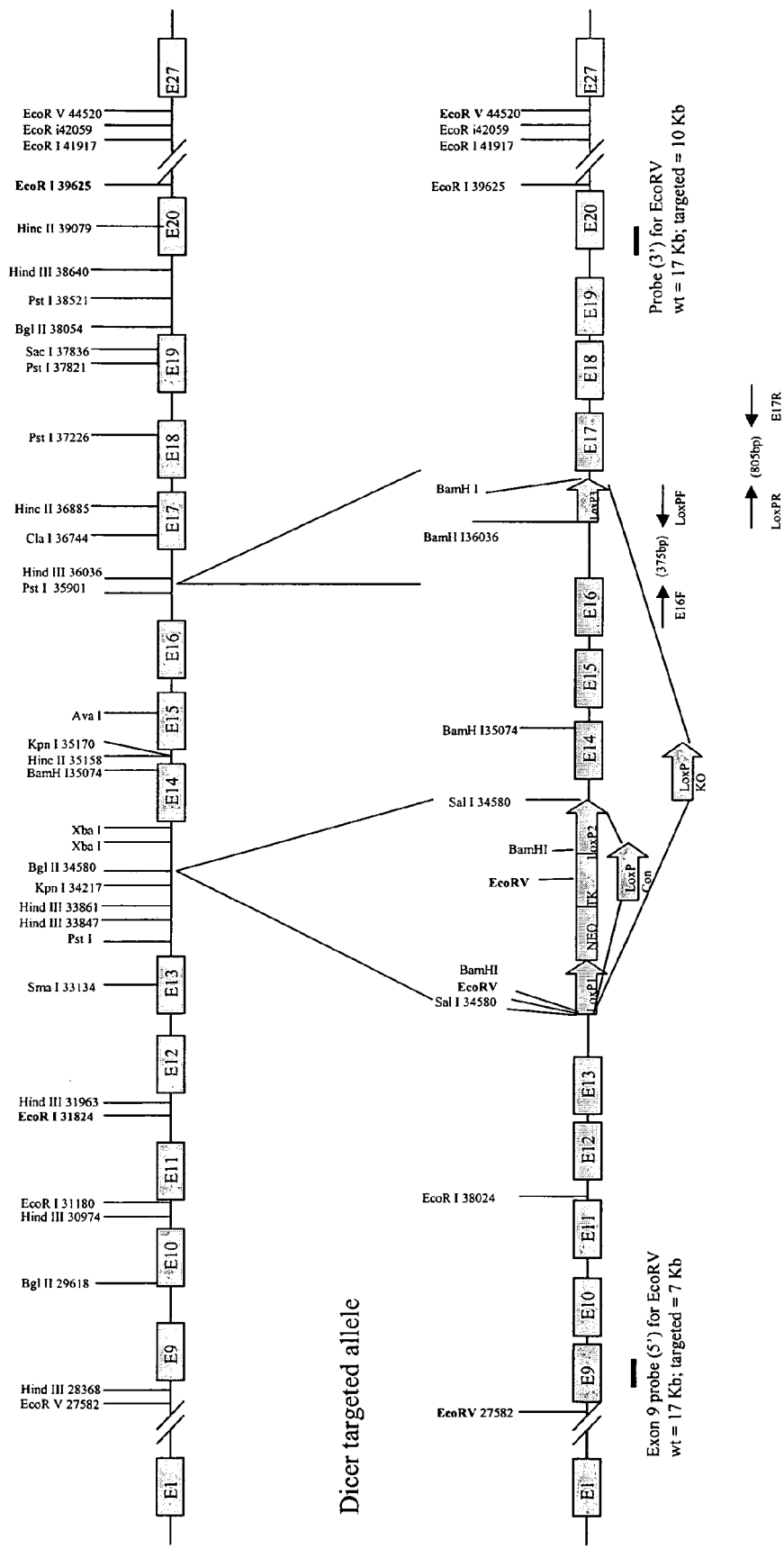
FIG. 1 is a schematic representation of the structure of the mouse genomic Dicer1 wild-type allele and the Dicer1 targeted allele generated by correct homologous recombination-mediated insertion of the synthetic construct of the instant invention. This synthetic construct contains three loxP sites, two of which directly flank sequences encoding for Neomycin Phosphotransferase (NEO, conferring neomycin/G418 resistance) and Thymidine Kinase (TK) selectable markers as shown, with this selectable marker cassette located between exons 13 and 14 of Dicer1 following genomic integration, and a third loxP site located between Dicer1 exons 16 and 17 following genomic integration as indicated. Cre recombinase-mediated loxP recombination of the Dicer1 targeted allele and selection for loss of the selectable marker cassette can result in either of two forms of the Dicer1 targeted allele—a conditional allele (indicated as "Con", and also referred to as a "floxed" allele of Dicer1) from which the NEO and TK selectable markers have been excised to generate a targeted Dicer1 allele containing two loxP sites flanking Dicer1 exons 14 through 16; or a knockout ("KO") allele that lacks NEO, TK and Dicer1 exons 14 through 16. Probe and primer oligonucleotides used to confirm genomic integration of the synthetic construct and arrangement of the loxP-containing Dicer1 targeted allele are also depicted.

The present invention is based, at least in part, on the generation of cells and viable non-human animals that contain a synthetic conditional allele of the Dicer1 gene. In cells and cell lines of the invention, the Dicer1 gene is replaced by homologous recombination between the endogenous allele and a conditional allele of the Dicer1 gene, or portion thereof. In the nonhuman animal of the invention, such replacement of the Dicer1 gene with a conditional allele of the Dicer1 gene or portion thereof has been performed in an embryonic stem cell precursor of the animal. The embryonic stem cell precursor is then allowed to develop (i.e., by microinjection into a blastocyst and implantation of the blastocyst into a pseudopregnant foster animal), resulting in an animal having at least one conditional allele of the Dicer1 gene. The animal may have one Dicer1 gene allele replaced by the Dicer1 conditional allele of the instant invention (i.e., the animal may be heterozygous for the conditional allele), or more preferably, the diploid animal has both Dicer1 gene alleles replaced by conditional alleles (i.e., the animal is homozygous for the conditional allele). The non-human animal of the instant invention may also be chimeric for the conditional Dicer1 allele. In one embodiment of the invention, replacement of both Dicer1 gene alleles with conditional alleles produces animals in which expression or administration of the Cre recombinase of bacteriophage P1 is capable of producing a functional knockout of the Dicer1 gene, within those cells of the animal containing the conditional Dicer1 allele and exposed to the Cre recombinase. In these animals, expression of the Dicer1 gene product from the genomically-integrated conditional alleles is substantially reduced or substantially absent relative to non-mutant animals, within those cells of the animal expressing or administered the Cre recombinase. The conditional Dicer1 genes may also be mutant or polymorphic alleles of Dicer1, such that an altered Dicer1 gene product is conditionally produced in the animal (the altered form of Dicer may be present in those cells or tissues not expressing or administered the Cre recombinase, whereas the altered form of Dicer is not expressed by cells expressing or administered the Cre recombinase). One nonhuman animal of the invention having a replaced Dicer1 gene is a mouse.

The DNA construct(s) of the instant invention may also be used to generate mammalian cell lines containing the synthetic conditional allele of Dicer1. The conditional allele of Dicer1 in such cell lines may be genomically integrated at the Dicer1 allele in heterozygous or homozygous fashion, or the conditional allele may be randomly integrated into the genome.

The animals of the invention are useful, for example, as inducible animal models of RNAi pathway disruption that allow for precise temporal- and tissue-specific control of Dicer, and therefore RNAi pathway function, as an in vivo system to evaluate the role of Dicer in various biological processes (e.g., embryonic development, RNAi pathway function, association with disease states, etc.), and as standard controls to evaluate the efficacy and side effects of putative Dicer inhibitors. The animals can also be used to identify disease states for treatment with Dicer, RNAi pathway, and siRNA-comprising inhibitors.

So that the invention may be more readily understood, certain terms are first defined.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Alternatively, a vector can be linear.

The term "recombinant vector" includes a vector that has been altered, modified or engineered such that it contains greater, fewer or different nucleic acid sequences than those included in a naturally-occurring vector.

The term "floxed" has its art-recognized meaning, specifically referring to nucleotide sequences that are flanked by two or more lox sites, most commonly loxP sites. In certain embodiments of the instant invention, such floxed nucleotides exist within nucleic acid constructs, or as genomic integrants present in targeted alleles of a gene. A genotype, e.g., for Dicer1 in a mouse in which both genomic alleles of Dicer1 contain two or more loxP sites each, can be notated as e.g., dicer1$^{flox/flox}$.

The term "site of inducible recombination", as used herein, refers to a region of DNA sequence identified in the art as a target region for the activity of a recombinase. In the Cre/lox system featured in certain embodiments of the invention, a recombinase protein, e.g., the Cre recombinase protein, interacts specifically with its respective site-specific recombination sequence, known as lox sites, to invert or excise the intervening sequences.

The term "inducible recombination", as used herein, refers to the process mediated by a recombinase, wherein inversion or excision of nucleic acid sequences flanked by recombinase target sites occurs.

The term "vertebrate Dicer1 genomic sequence", as used herein, refers to any sequence found in a vertebrate (e.g., mouse, human, dog, rat, monkey, horse, cattle, etc.) genome that is recognized in the art as the Dicer1 gene. While sequence for C57BL/6 mouse Dicer1 is listed herein, genomic Dicer1 sequence has been identified in a number of vertebrate species including mouse and human, and is readily identified in all vertebrate animals on the basis of sequence homology and/or alignment. Dicer1 sequence for a number of vertebrates is readily available through Genbank, and various other art-recognized sequence databases. Reference to "mouse Dicer1 genomic sequence" is in no way intended to limit such sequence to that listed herein for the C57BL/6 strain of mouse, as sequence polymorphisms are known to occur at an average rate of approximately one polymorphic base per kilobase of sequence in comparing sequences of the most commonly used inbred laboratory strains of Mus musculus (Lindblad-Toh, K. et al., 2000 *Nat. Genet.* 24, 381-6). Thus, the term "mouse Dicer1 genomic sequence" refers both to the C57BL/6 sequence listed herein, and to any genomic sequence readily identifiable as the Dicer1 gene or portion thereof, in any strain of Mus musculus. Sequence polymorphism may also be exogenously introduced into a Dicer1 sequence, and reference to Dicer1 sequence is intended to include all sequences or portions thereof that remain readily recognizable as Dicer1 sequence, regardless of exogenously introduced polymorphism.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "PAZ domain" refers to Polyubiquitin Associated Zinc finger domain. Such domains are art-recognized features identifiable within certain polypeptide sequences, and are functionally believed to mediate protein-protein interactions, protein modifications, etc. In the mouse Dicer1 genomic sequence, exons 14, 15 and 16 are located within the PAZ domain-encoding sequence.

"Operably linked" or "in operable combination", as used herein, refer to an arrangement of elements wherein the components so described are configured so as to perform their desired function. Thus, a sequence encoding for a given selectable marker (e.g., neomycin phosphotransferase, thymidine kinase, etc.) operably linked, e.g., to a given region of sequence that is targeted for homologous recombination-mediated genomic integration is capable of conferring a phenotype to cells in which genomic integration has occurred for the targeted sequence. (Alternatively, in some instances, lack of genomic integration or removal of such a selectable marker may confer a phenotype indicative of a desired state of genomic integration or configuration of the targeted sequences.) Such sequence for a selectable marker need not be contiguous with the targeted sequence, so long as it functions as a marker of the state of integration or configuration of the targeted sequence. Thus, for example, intervening sequences may be present between the sequence for the selectable marker and sequences targeted for genomic integration or rearrangement. An "operably linked" selectable marker might also function in any orientation (e.g., 5' or 3' of a targeted sequence, in forward or reverse orientation) relative to a targeted sequence.

By "selectable marker" or "marker", as used herein, are meant a gene which confers a phenotype on a cell expressing the marker, such that the cell can be identified under appropriate conditions. Generally, a selectable marker allows selection of transfected cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a nucleic acid element containing the selectable marker when the cells are grown in an appropriate selective medium. For example, selectable markers include: cytotoxic markers and drug resistance markers, whereby cells are selected by their ability to grow on media containing one or more of the cytotoxins or drugs; auxotrophic markers by which cells are selected by their ability to grow on defined media with or without particular nutrients or supplements, such as thymidine and hypoxanthine; metabolic markers by which cells are selected for, e.g., their ability to grow on defined media containing the appropriate sugar as the sole carbon source, or markers which confer the ability of cells to form colored colonies on chromogenic substrates or cause cells to fluoresce.

"Transformation," as used herein, refers to the insertion of an exogenous polynucleotide into a host cell, irrespective of the method used for insertion: for example, transformation by direct uptake, transfection, infection, and the like. The exogenous polynucleotide may be maintained as a nonintegrated vector, for example an episome, or alternatively, may be integrated into the host genome.

The term "RNA interference" or "RNAi" (also referred to in the art as "gene silencing" and/or "target silencing", e.g., "target mRNA silencing"), as used herein, refers generally to a sequence-specific or selective process by which a target molecule (e.g., a target gene, protein or RNA) is downregulated. In specific embodiments, the process of "RNA interference" or "RNAi" features degradation or post-transcriptional silencing of RNA molecules, e.g., RNA molecules within a cell, said degradation or silencing being triggered by an RNAi agent. Degradation and post-transcriptional silencing of target RNA is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "RNA silencing agent", as used herein, refers to an RNA (or analog thereof), having sufficient sequence complementarity to a target RNA (i.e., the RNA being degraded) to direct RNA silencing (e.g., RNAi). An RNA silencing agent having a "sequence sufficiently complementary to a target RNA sequence to direct RNA silencing" means that the RNA silencing agent has a sequence sufficient to trigger the destruction or post-transcriptional silencing of the target RNA by the RNA silencing machinery (e.g., the RISC) or process. An RNA silencing agent having a "sequence sufficiently complementary to a target RNA sequence to direct RNA silencing" is also intended to mean that the RNA silencing agent has a sequence sufficient to trigger the translational inhibition of the target RNA by the RNA silencing machinery or process. An RNA silencing agent having a "sequence sufficiently complementary to a target RNA encoded by the target DNA sequence such that the target DNA sequence is chromatically silenced" means that the RNA silencing agent has a sequence sufficient to induce transcriptional gene silencing, e.g., to down-modulate gene expression at or near the target DNA sequence, e.g., by inducing chromatin structural changes at or near the target DNA sequence.

An "RNA silencing inhibitory agent", as used herein, refers to any agent that is capable of interfering with the RNA silencing process. Such inhibitors might include, e.g., inhibitors of RISC assembly, inhibitors of siRNA or miRNA processing, 2'-O-methyl-oligonucleotides that are complementary to certain siRNA guide strands or miRNAs, small molecules and/or chemical compounds that interfere with RNA silencing, etc.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, the term "microRNA" ("miRNA") refers to an RNA (or RNA analog) comprising the product of an endogenous, non-coding gene whose precursor RNA transcripts can form small stem-loops from which mature miRNAs are cleaved by Dicer (Lagos-Quintana et al., 2001; Lau et al., 2001; Lee and Ambros, 2001; Lagos-Quintana et al., 2002; Mourelatos et al., 2002; Reinhart et al., 2002; Ambros et al., 2003; Brennecke et al., 2003b; Lagos-Quintana et al., 2003; Lim et al., 2003a; Lim et al., 2003b). miRNAs are encoded in genes distinct from the mRNAs whose expression they control. Mature miRNAs represent the single stranded product of Dicer cleavage that then function as guide RNA fragments in mediating RNA silencing when incorporated into RISC.

As used herein, "transgenic animals" refers to those animals which have incorporated a heterologous or foreign gene into their genome. The term "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term "genetic manipulation" includes the introduction of a recombinant DNA molecule. This molecule is preferably integrated within a chromosome to ensure that it will be passed on to offspring, or it may be extrachromosomally replicating DNA.

In aspects and embodiments of the instant invention, transgenic animals are non-human mammals. According to the present invention, exemplary mammals include, without limitation, rodents (such as rats and mice), dogs, cats, pigs, sheep, cows, goats, horses and rabbits. Desirably the mammal is non-human. As used herein, the term "rodent" refers to all members of the phylogenetic order Rodentia. In one embodiment, a rodent is a mouse.

As used herein, the term "conditional allele" refers to any form of a gene that may be inducibly altered in function and/or structure by application, administration or expression of an exogenous reagent (e.g., Cre recombinase expression) or state change (e.g., temperature change), such that the activity or abundance of the gene, expressed transcript, or encoded gene product is changed. In certain embodiments of the instant invention, a Dicer1 conditional allele specifically refers to a synthetic form of the Dicer1 gene or portion thereof comprising sites of recombination (in some embodiments of the invention, loxP sites) upon which expression or administration of a recombinase (e.g., Cre recombinase) is capable of acting to alter—and in certain embodiments, functionally disrupt—Dicer1 and/or Dicer activity.

The term "Dicer1 knockout inducing agent", as used herein, refers to any reagent or state change that induces excision of targeted Dicer1 sequences within a conditional Dicer1 allele of the invention, such that production of functional Dicer is inhibited at least at the conditional Dicer1 allele.

Additionally, as used herein, the terms "conditional disruption" and "conditional knockout" refer to both the act of and final product of administering or expressing a reagent, force or state change capable of functionally disrupting the activity of a targeted gene or gene product.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A gene "involved" in a disorder includes a gene, the normal or aberrant expression or function of which effects or causes a disease or disorder or at least one symptom of said disease or disorder.

Various methodologies of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi-modulatory agent (e.g., an oligonucleotide, compound, etc., that alters sequence-specific RNAi activity) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

One aspect of the invention pertains to a nonhuman animal having cells in which at least one allele of an endogenous Dicer1 gene is replaced by a conditional allele of Dicer1. In certain embodiments, both the somatic and germ cells of the animal have a Dicer1 conditional allele. In some of these embodiments, the somatic and germ cells have both alleles of the Dicer1 gene replaced by a Dicer1 conditional allele, which in many embodiments is the lox site-flanked ("floxed") Dicer1 allele of the instant invention. Thus, the invention provides nonhuman animals in which Dicer activity may be readily functionally disrupted via expression or administration of an exogenous reagent, force or state change. In certain embodiments, disruption of Dicer1 is caused by expression or administration of the Cre recombinase.

As used herein, a Dicer1 gene that is "functionally disrupted" has a mutation that prevents the normal function of the Dicer1 gene, e.g., prevents expression of a normal Dicer1 gene product and/or prevents expression of normal amounts of the Dicer1 gene product. The mutation causing the functional disruption can be an insertion, deletion or point mutation(s). In certain embodiments of the invention, the functional disruption is a Cre recombinase-induced deletion of Dicer1 exons 14, 15 and 16, and in some embodiments, exons 14, 15 and 16 are deleted from a genomically integrated Dicer1 conditional allele in an animal or cell line. In one embodiment, both Dicer1 gene alleles are functionally disrupted such that expression of the Dicer1 gene product is substantially reduced or substantially absent in cells of the animal. The term "substantially reduced" is intended to mean that less than 50% of the normal amount of Dicer protein is produced in cells of the animal. The term "substantially absent" is intended to mean that essentially undetectable amounts of Dicer1 gene product are produced in cells of the animal. A mutation in which Dicer1 protein expression is substantially absent is also referred to in the art as a "null mutation" and an animal carrying such a null mutation is also referred to as a "knockout animal." Although animals with substantially reduced or substantially absent levels of a target protein are typically made by disrupting the coding region of the target gene, an alternative approach is to disrupt the cis-regulatory element(s) of the gene such that transcription of the gene is downmodulated. Such an approach, referred to as a "knockdown" mutation, is described further in McDevitt, M. A. et al. (1997) *Proc. Natl. Acad. Sci. USA* 94:6781-6785. Thus, a conditional allele of Dicer1 might also be constructed through conditional alteration of cis-regulatory sequences of the Dicer1 gene.

In another embodiment, both Dicer1 gene alleles comprise mutant or polymorphic/variant forms of the Dicer1 conditional allele, such that an altered form of the Dicer1 gene product is expressed in cells of the animal in the absence of expression or administration of Cre recombinase, whereas in the the presence of Cre recombinase expression or administration, these Dicer1 conditional alleles are functionally disrupted [in certain embodiments, through recombinase-induced deletion of exons 14, 15 and 16 of the conditional Dicer1 allele(s)]. For example, one or more point mutations or deletion mutations can be introduced into the Dicer1 gene to thereby alter the amino acid sequence of the Dicer1 gene product encoded therein. Dicer1 is known to encode for a protein comprising a helicase domain, a PAZ domain, two RNase III domains, and a dsRBD domain. Mutations or polymorphisms present within any of these domains could impact the functional activity of Dicer. Exons 14, 15 and 16, inducibly excised in certain embodiments of the instant invention, are located within the PAZ domain-encoding sequence of the mouse Dicer1 gene.

In the animals of the invention, at least one allele of an endogenous Dicer1 gene contains exogenous DNA that has been inserted into the endogenous Dicer1 gene such that expression of the endogenous Dicer1 gene is functionally unaffected in the absence of a recombination-inducing agent, but functionally disrupted in the presence of a recombination-inducing agent, such as the Cre recombinase in certain embodiments of the instant invention. As used herein, the term "exogenous DNA" is intended to refer to DNA that is not found within the endogenous Dicer1 gene in the genome of the animal as it exists in nature. That is, exogenous DNA represents "transgenic" DNA that has been specifically introduced into the genome of the animal by genetic manipulation. In one such embodiment, the exogenous DNA, when initially inserted into the endogenous Dicer1 gene, comprises a selectable marker (e.g., a neomycin phosphotransferase gene), which aids in identifying cells that have exogenous DNA specifically inserted into the Dicer1 gene. In all embodiments of the instant invention, the exogenous DNA additionally comprises sequences that may be recognized and acted upon by a recombinase—in certain embodiments, the Cre recombinase of bacteriophage P1.

In one embodiment, a conditional Dicer1 allele is generated in a cell by homologous recombination between the endogenous Dicer1 allele and a targeting vector comprising a conditional Dicer1 gene, or portion thereof, that is introduced into the cell. The genomically integrated conditional Dicer1 gene may comprise wild-type, mutant or polymorphic forms of the Dicer1 allele in the absence of administration or expression of a recombinase. In the presence of a recombinase, at least one region of this conditional Dicer1 allele is deleted via excision. In certain embodiments, excision of Dicer1 exons 14, 15 and 16 generates a functional knockout of the Dicer1 allele. The cell can be a differentiated cell type that normally expresses Dicer. Alternatively, the cell can be a pluripotent progenitor cell that can develop into an animal, such as an embryonic stem cell. When the cell is an embryonic stem cell, the cell can be introduced into a blastocyst and the blastocyst allowed to develop in a foster animal to thereby produce an animal having somatic and germ cells in which a Dicer1 gene allele is a conditional allele. Such an animal is referred to herein as a "homologous recombinant" animal. One homologous recombinant animal of the invention is a mouse.

To create a homologous recombinant cell or animal, a targeting vector is prepared which contains DNA encoding a Dicer1 gene, or portion thereof, having exogenous DNA and/or a mutation introduced therein. One such targeting vector for creating a null mutation in an endogenous Dicer1 gene includes Dicer-encoding DNA into which has been inserted non-Dicer-encoding DNA. For example, in one embodiment, a targeting vector of the invention for replacing an endogenous Dicer1 allele with a conditional allele of the Dicer1 gene in a cell comprises:

a) a replacement portion containing nonhomologous sequence comprising at least two sites of inducible recombination derived from an exogenous source (e.g. loxP, FRT, att, etc.), wherein the sites of inducible recombination are positioned at least on either flank of sequence homologous to the endogenous Dicer1 gene sequence [sites of inducible recombination additionally may flank other nonhomologous sequence(s) for which inducible deletion is desirable, e.g. selectable markers];

b) a first homology region located upstream of the replacement portion, the first homology region having a nucleotide sequence with substantial identity to a first Dicer1 gene sequence; and c) a second homology region located downstream of the replacement portion, the second homology region having a nucleotide sequence with substantial identity to a second Dicer1 gene sequence, the second Dicer1 gene sequence having a location downstream of the first Dicer1 gene sequence in a naturally occurring endogenous Dicer1 gene.

Thus, the replacement portion is flanked 5' and 3' by nucleotide sequences with substantial identity to Dicer1 gene sequences. A nucleotide sequence with "substantial identity" to a Dicer1 gene sequence is intended to describe a nucleotide sequence having sufficient homology to a Dicer1 gene sequence to allow for homologous recombination between the nucleotide sequence and an endogenous Dicer1 gene sequence in a host cell. Typically, the nucleotide sequences of the flanking homology regions are at least 90%, more preferably at least 95%, even more preferably at least 98% and most preferably 100% identical to the nucleotide sequences of the endogenous Dicer1 gene to be targeted for homologous recombination. Most preferably, the flanking homology regions are isogenic with the targeted endogenous allele (e.g., the DNA of the flanking regions is isolated from cells of the same genetic background as the cell into which the targeting construct is to be introduced). Additionally, the flanking homology regions of the targeting vector are of sufficient length for homologous recombination between the targeting vector and an endogenous Dicer1 gene in a host cell when the vector is introduced into the host cell. Typically, the flanking homology regions are at least 1 kilobase in length and more preferably are at least several kilobases in length.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al, (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

In certain embodiments, greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between polymorphic forms (e.g., species- and musculus strain-dependent forms) of targeted exons or portions thereof of Dicer1, is preferred. Alternatively, homology between polymorphic exons or portions thereof of Dicer1 may be defined functionally as a nucleotide sequence (or oligonucleotide sequence) a portion of which is capable of hybridizing with a polymorphic form of Dicer1. Examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology,* 1995, F. M. Ausubel et al., eds., John Wiley & Sons, Inc., sections 2.10 and 6.3-6.4, incorporated herein by reference.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Commonly used selectable markers include those which confer resistance to drugs, such as G418, hygromycin and methotrexate. Nucleic acid encoding a selectable marker can be introduced into a host cell on the same vector as that encoding Dicer or can be introduced on a separate vector. Cells stably transfected with the introduced nucleic acid can be identified by drug selection (e.g., cells that have incorporated the selectable marker gene will survive, while the other cells die).

To create a cell homozygous for the Dicer1 conditional allele, the G418 escalation method of Mortensen, R. N. et al. ((1992) *Mol. Cell. Biol.* 12:2391-2395) can be used on the heterozygous cells. Alternatively, the first allele of a wild type host cell can be replaced with a Dicer1 conditional allele by a first homologous recombination event that is selected with one marker (e.g., G418 resistance) and then the second allele of the heterozygous cells can be replaced with a Dicer1 conditional allele by a second homologous recombination event that is selected with a different marker (e.g., hygromycin resistance) (see e.g., TeRiele, H. (1990) *Nature* 348:649-651).

A typical targeting vector has a positive selection expression cassette as a nonhomologous domain of the replacement portion. The term "positive selection expression cassette" refers to nucleotide sequences encoding a positive selection marker operatively linked to regulatory elements that control expression of the positive selection marker (e.g., promoter and polyadenylation sequences). A "positive selection marker" allows for selection of cells which contain the marker, whereas cells that do not contain and express the marker are selected against (e.g., are killed by the selecting agent). For example, one such positive selection expression cassette includes a neomycin phosphotransferase ("neo") gene operatively linked to a promoter and a polyadenylation signal. Cells carrying and expressing the neo gene exhibit resistance to the selecting agent G418.

In addition to the positive selection expression cassette, a targeting vector of the invention typically also includes a negative selection expression cassette. A "negative selection expression cassette" refers to nucleotide sequences encoding a negative selection marker operatively linked to regulatory elements that control expression of the negative selection marker. A "negative selection marker" allows for selection against cells which carry the marker, e.g., cells that contain and express the marker are killed by a selecting agent, whereas cells that do not contain and express the negative selection marker survive. For example, one such negative selection expression cassette includes a herpes simplex virus thymidine kinase ("tk") gene operatively linked to a promoter and a polyadenylation signal. Cells that contain and express the tk gene can be killed, for example, by the selecting agent gancyclovir.

Figure 2:
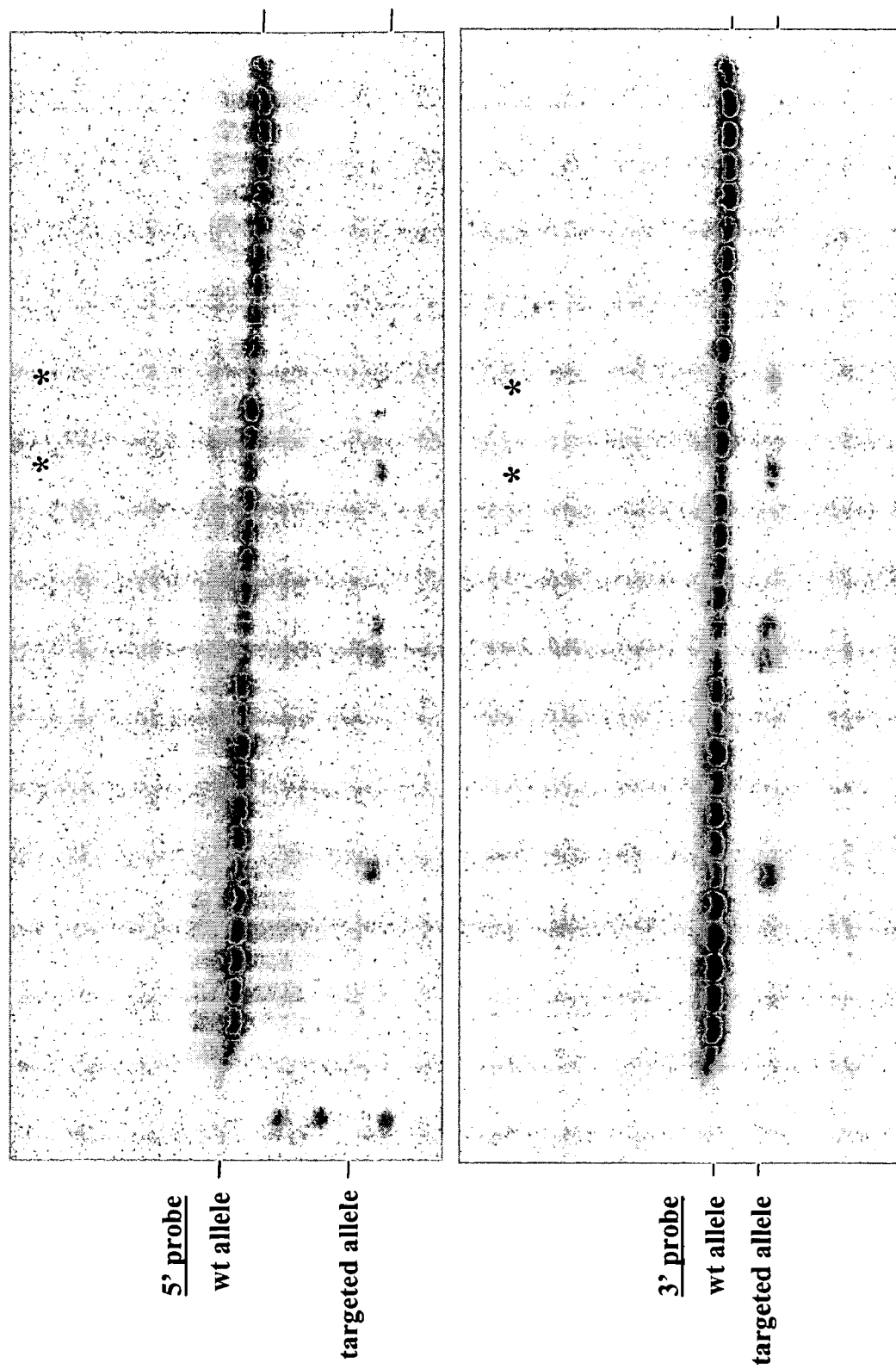
FIG. 2 displays results of Southern blots, using probes as indicated in FIG. 1, performed on embryonic stem (ES) cell clones following transfection with the targeting construct of the instant invention and selection of neomycin-resistant clones with G418. Asterisks indicate those cell lines exhibiting correct genomic integration of targeting construct sequence.

In certain embodiments, this configuration of the targeting vector allows for implementation of an iterative process of positive, then negative selection during generation of homologous recombinant cells that contain a conditional allele of Dicer1. Cells into which the targeting vector has been introduced are selected that contain and express the positive selection marker. Accordingly, these cells carry the nonhomologous replacement portion DNA (e.g., the inserted neo gene). Such cells may then be assessed for correct genomic integration of the replacement portion DNA (refer to Example 3? and FIG. 2). Nonhomologous sequences of the replacement domain—potentially all sites other than at least one site of inducible recombination—may then be eliminated by inducing recombination at sites flanking the negative selection cassette, with selection against the negative selection cassette (e.g. thymidine kinase) allowing for enhanced efficiency of recovery of cells lacking the negative selection cassette but still containing a conditional Dicer1 allele that may be subsequently induced to delete Dicer1 sequences located between remaining sites of recombination. In certain targeting vectors of the instant invention, the replacement domain sequence contains three loxP sites, two of which flank sequences for a selectable marker cassette, and a third loxP site located on the opposite flank of Dicer1 exons 14, 15 and 16 from the loxP-flanked selectable marker cassette. Induction of loxP-mediated excision by Cre recombinase and selection of cells with FIAU (a selection agent that excludes cells containing thymidine kinase) yielded five embryonic stem cell lines containing a genomically-integrated inducible conditional allele of Dicer1 from which selectable markers of the original targeting construct had been excised, and also containing loxP sites flanking sequences for exons 14, 15 and 16 of the Dicer1 gene (generation of such cell lines is detailed in Example 4).

In one embodiment, the targeting vector includes flanking homologous regions having substantial identity to mouse Dicer1 gene sequences to thereby target an endogenous mouse Dicer1 gene in a mouse host cell (e.g., a murine embryonic stem cell) for homologous recombination. Murine Dicer1 genomic DNA used as the flanking homology regions of the targeting vector can be isolated from a murine genomic DNA library (e.g. murine BAC library—the BAC library of the instant invention is commercially available and was obtained from Invitrogen. It contains female mouse 129SV-strain genomic DNA inserted into the EcoR1 sites of the pBACe3.6 vector.) by screening the library with a cDNA probe encompassing all or part of the murine Dicer1 cDNA using standard techniques. For example, a genomic BAC library can be screened with a probe from the mouse Dicer1 cDNA to isolate mouse Dicer1 genomic DNA for use in a targeting vector (see Example 1). Cloning of a mouse Dicer1 cDNA is described in detail in Nicholson and Nicholson (*Mamm. Genome* 13:67-73), and the nucleotide sequence of the mouse Dicer1 cDNA is available in the GenBank database at least at accession number NM_148948.1. The Dicer1 gene has been localized to mouse chromosome 12 (Nicholson and Nicholson *Mamm. Genome* 13:67-73).

A restriction map of approximately 17 kb of the mouse Dicer1 gene is shown in FIG. 1. To create a targeting vector for introducing an inducible conditional allele of the endogenous mouse Dicer1 gene into a cell line, the nonhomologous replacement portion (e.g., exogenous sequence comprising sites of inducible recombination, such as loxP sites; a positive selection expression cassette, such as the neo gene) preferably is inserted immediately downstream of a homology region in the targeting vector that is highly homologous to at least a portion of the sequence of the genomic Dicer1 intron that is located between exons 13 and 14 of Dicer1 in wild-type mice (in some embodiments, 129 strain mice). In certain embodiments of the invention, an additional loxP site is positioned immediately upstream of sequence comprising exons 16 and 17 of Dicer1.

The replacement portion (containing both nonhomologous exogenous sequences, e.g., loxP sites in certain embodiments, and homologous Dicer1 allele sequences flanked by sites of inducible recombination) preferably is flanked upstream by approximately 3.5 kb of adjacent Dicer1 gene sequence and downstream by approximately 3.6 kb of adjacent Dicer1 gene sequence (refer to FIG. 1A for a schematic diagram of one such targeting construct). However, it will be appreciated by the skilled artisan that a replacement portion, including flanking loxP sites in certain embodiments of the instant invention, can be constructed to target and inserted at other locations within the Dicer1 gene, and flanked by different homology regions, to thereby generate a conditional allele of the gene. Construction of a targeting vector for generating a conditional allele of a mouse Dicer1 gene is described in further detail in Example 1. Conditional disruption of the mouse Dicer1 gene sequence may prevent expression of a full-length mouse Dicer1 mRNA transcript (e.g., by inducible deletion of exons 14, 15 and 16) or may lead to expression of a mouse Dicer1 mRNA transcript that encodes an altered form of mouse Dicer.

Alternatively, to target a human Dicer1 gene in a human host cell (e.g. in immortalized human cell lines) for homologous recombination, the targeting vector includes flanking homology regions having substantial identity to human Dicer1 gene sequences. Human Dicer1 genomic DNA sequences can be isolated by screening a human genomic DNA library with a cDNA probe encompassing all or part of the human Dicer1 cDNA using standard techniques. Cloning of the human Dicer1 cDNAs is described in detail in Matsuda et al. (*Biochim Biophys Acta* 1490:163-169) and the nucleotide sequence of the human Dicer1 cDNA is available in the GenBank database at least at accession number NM_177438. As described for the mouse Dicer1 gene, the conditional disruption of the human Dicer1 gene sequence in a human cell may prevent expression of a full-length human Dicer1 mRNA transcript or may lead to expression of a human Dicer1 mRNA transcript that encodes an altered form of human Dicer, following induction (e.g. Cre recombinase administration in certain embodiments) of the conditional disruption in the human cell.

To create a homologous recombinant animal of the invention, an embryonic stem cell having at least one conditional Dicer1 gene allele is introduced into a blastocyst, the blastocyst is implanted into a pseudopregnant foster mother, and the embryo allowed to develop to term. The resultant animal is a chimera having cells descendant from the embryonic stem cell. Chimeric animals in which the embryonic stem cell has contributed to the germ cells of the animal can be mated with wild type animals to thereby produce animals heterozygous for the Dicer1 conditional allele in all somatic and germ cells. The heterozygous animals can then be mated to create animals homozygous for the Dicer1 conditional allele (i.e., having both Dicer1 gene alleles replaced with inducible conditional alleles of Dicer1). These animals can be used as control or test animals for in vivo assays (described in further detail below). Additionally, cells of the animal homozygous for the Dicer1 conditional allele can be isolated from the animals and cultured for use in in vitro assays. Furthermore, immortalized cell lines can be prepared from cells of the animal using standard techniques for cell immortalization, e.g., by transfection of the cells with an expression vector encoding myc, ras or SV40 large T antigen.

Targeting vectors and methodologies for creating and integrating a murine Dicer1 conditional allele by homologous recombination are described in further detail in Examples 1-2. Moreover, in addition to the foregoing and the Examples, other methods and reagents known in the art for specifically altering an endogenous gene in a host cell can be applied to the Dicer1 gene to create cells and animals of the invention.

For a general review on gene targeting in embryonic stem cells see Moreadith and Radford (1997) *J. Mol. Med.* 75:208-216. For additional descriptions of targeting vectors and methodologies, see also e.g., Thomas, K. R. et al. (1986) *Cell* 44:419-428; Thomas, K. R. et al. (1987) *Cell* 51:503-512; Thomas, K. R. et al. (1992) *Mol. Cell. Biol.* 12:2919-2923; Deng, C. and Capecchi, M. R. (1992) *Mol. Cell. Biol.* 12:3365-3371; Hasty, P. et al. (1992) *Mol. Cell. Biol.* 12:2464-2474; Li, E. et al. (1992) *Cell* 69:915; Zhang, H., et al. (1994) *Mol. Cell. Biol.* 14:2404-2410; Bradley, A. in *Teratocarcinomas and Embryonic Stem Cells: A Practical Approach*, E. J. Robertson, ed. (IRL, Oxford, 1987) pp. 113-152; PCT International Publication No. WO 90/11354; PCT International Publication No. WO 91/01140; PCT International Publication No. WO 91/19796; PCT International Publication No. WO 92/20808; and PCT International Publication No. WO 93/04169. Both copies of a Dicer1 gene can also be replaced with conditional alleles according to the methods described in PCT International Publication WO 93/16177.

Alternative approaches to the positive/negative selection method of homologous recombination described above are available in the art, such as "hit and run" gene targeting (see e.g., Lakhlani, P. P. et al. (1997) *Proc. Natl. Acad. Sci. USA* 94:9950-9955) and transposon-generated "knock-out" and "knock-in" gene targeting (see e.g., Westphal and Leder (1997) *Curr. Biol.* 7:530-533). Methods for efficient gene targeting, allowing for a high frequency of homologous recombination events, are described in Templeton, N. S. et al. (1997) *Gene Ther.* 4:700-709. This type of efficient gene targeting can allow for detection of homologous recombination events without the need for the use of selectable markers. Moreover, efficient methods for screening for homologous recombination in ES cells using reverse transcription-polymerase chain reaction (RT-PCR) have been described (see Danoff, T. M. et al. (1997) *Biotechniques* 22:22-24, 26.

In certain embodiments of the instant invention, recombinase-mediated homologous recombination is used to functionally disrupt a Dicer1 conditional allele (see e.g., PCT International Publication WO 93/22443). Numerous examples of the use of the Cre/Lox recombinase system of bacteriophage for precise genomic manipulation are known in the art (see e.g., Gagneten, S. et al. (1997) *Nucl. Acids Res.* 25:3326-3331; Xiao and Weaver (1997) *Nucl. Acids Res.* 25:2985-2991; Agah, R. et al. (1997) *J. Clin. Invest.* 100:169-179; Barlow, C. et al. (1997) *Nucl. Acids Res.* 25:2543-2545; Araki, K. et al. (1997) *Nucl. Acids Res.* 25:868-872). One advantage of the Cre/Lox system is that it can allow for conditional inactivation of a gene interest. Additionally, methods and reagents for conditional inactivation of a gene of interest using a tetracycline-regulated gene expression system are described in PCT Publication WO 94/29442 and U.S. Pat. No. 5,650,298.

In addition to allowing for introduction of conditional alleles of the wild-type Dicer1 gene, similar techniques to those discussed above can be used to introduce polymorphisms, point mutations or deletions into a Dicer1 gene allele, wherein the polymorphic or mutant allele may be subject to induction of conditional excision of the Dicer1 gene allele to create a functional knockout of Dicer1 at that allele. For example, a point mutation(s) can be introduced into one or more of the functional domains of Dicer1 (the helicase domain, the PAZ domain, the two RNase III domains and/or the dsRBD domain). Point or deletion mutations can be introduced into a Dicer1 gene allele by, for example, the "hit and run" homologous recombination procedure (as described in Valancius, V. and Smithies, O. (1991) *Mol. Cell. Biol.* 11: 1402-1408; and Hasty, P. et al. (1991) *Nature* 350:243-246) or by the double replacement homologous recombination procedure (as described in Wu, H. et al. (1994) *Proc. Natl. Acad. Sci. USA* 91:2819-2823). Accordingly, in another embodiment, the invention provides homologous recombinant cells and animals (e.g., human cells or nonhuman animals) that contain a conditional allele of an altered Dicer1 gene product.

In another embodiment, the invention provides a nonhuman animal containing a conditional allele of the Dicer1 gene and which further comprises a transgene encoding a recombinase protein. In one embodiment, the transgene is randomly integrated into the genome of the animal. The transgene in certain embodiments encodes a recombinase protein from a different species as the animal (e.g., bacteriophage P1 Cre recombinase). Such an animal can be made, for example, by mating the animal containing the Dicer1 conditional allele with a second animal that carries a recombinase transgene in its genome. In one embodiment, the animal to which the conditional Dicer1 allele-containing animal is mated carries a recombinase transgene whose expression is limited to a particular cell type (based upon the regulatory sequences to which the transgene is linked). For example, a Dicer1 conditional allele-containing animal of the invention can be crossbred with a recombinase transgenic animal which expresses the recombinase only in liver cells due to use of a liver-specific promoter.

In another embodiment, the invention provides a nonhuman animal having a conditional allele of the endogenous Dicer1 gene and which further comprises a transgene encoding a Dicer protein. In one embodiment, the transgene is randomly integrated into the genome of the animal. The transgene can encode a Dicer protein from the same species as the animal (e.g., a mouse Dicer transgene in a Dicer1 conditional mouse). Such an animal can be made, for example, by mating the Dicer1 conditional animal with a second animal that carries a Dicer1 transgene in its genome. In one embodiment, the animal to which the Dicer1 conditional animal is mated carries a Dicer1 transgene whose expression is limited to a particular cell type (based upon the regulatory sequences to which the transgene is linked). For example, a Dicer1 conditional animal of the invention can be cross-bred with a Dicer1 transgenic animal containing a Dicer1 allele that expresses Dicer only in liver cells due to use of a liver-specific promoter. Resulting offspring of such a cross may then be conditionally disrupted at the integrated conditional allele of Dicer1 (e.g., through expression or administration of Cre recombinase), resulting in, e.g., adult mice expressing Dicer only in the liver.

Alternatively, the Dicer1 transgene can encode a heterologous Dicer1 protein (i.e., a Dicer1 protein from a different species than the animal). For example, an animal of the invention homozygous for a Dicer1 conditional allele, or a cell derived therefrom, can be augmented with a human Dicer1 gene to create a nonhuman cell or animal that expresses a human Dicer1 gene product. Following directed administration or expression of recombinase, these cells and animals can then be used to screen compounds to identify agents that inhibit the activity of human Dicer1, either in cultured cells or in vivo in animals (described further below). A human Dicer1 augmented animal can be made, for example, by introducing nucleic acid encoding human Dicer1 into the genome of embryonic progenitor cells obtained from an animal of the invention and allowing the embryonic cells to develop using standard techniques for creating transgenic and homologous recombinant animals. Nucleic acid encoding human Dicer1 can be integrated randomly into the genome of a Dicer1 conditional allele-containing animal (e.g., by microinjection of a human Dicer1 gene construct into fertilized oocytes obtained from an Dicer1 conditional allele-containing animal). Alternatively, a conditional allele of the human Dicer1 gene may be generated and integrated by homologous recombination into the endogenous Dicer1 locus of a non-human cell or animal (i.e., the endogenous Dicer1 gene can be replaced by an exogenously introduced human conditional Dicer1 gene). The human Dicer1 gene construct (whether or not the allele is a conditional human allele of Dicer1) can include upstream and/or downstream regulatory elements that allow for either tissue-specific, regulated expression of the Dicer1 polypeptide or constitutive expression of the human Dicer1 polypeptide in cells of the mammal. A human Dicer1 transgenic animal of the invention also provides a source of nonhuman cells that express human Dicer1 polypeptide. Such cells can be isolated from the animal and, if necessary, immortalized by standard techniques.

The features and characteristics of the animals of the invention, and cells derived therefrom, make them useful for a wide variety of applications, as described in further detail in the subsections below:

I. Cre/lox System

The present invention utilizes a site specific recombinase system, e.g., the Cre/lox system of bacteriophage P1, which is widely used to engineer gene recombination in mice and plants. Other different site specific recombinase systems that may be used include the FLP/FRT system of yeast (see e.g., O'Gormen et al. (1991) Science 251:1351), the Gin recombinase of phage Mu, the Pin recombinase of *E. coli*, and the R/RS system of the pSR1 plasmid. In the Cre/lox system, a recombinase protein, e.g., the Cre recombinase protein, will interact specifically with its respective site-specific recombination sequence, known as lox sites, to invert or excise the intervening sequences.

Cre is a 38 kDa recombinase protein from bacteriophage P1 which mediates intramolecular (excisive or inversional) and intermolecular (integrative) site specific recombination between loxP sites (see review article by Brian Sauer in Methods of Enzymology; 1993, Vol. 225, 890-900). The constructs and genetically-manipulated animals of the instant invention feature loxP sites placed in an orientation such that excisive site specific recombination occurs. A loxP site (locus of crossing over) consists of two 13 bp inverted repeats separated by an 8 bp asymmetric spacer region.

The nucleotide sequence of the insert repeats and the spacer region of LoxP is as follows: ATAACTTCGTATA ATGTATGC TATACGAAGTTAT (SEQ ID NO: 3). Other suitable lox sites include LoxB, LoxC2, LoxL and LoxR sites which are nucleotide sequences isolated from *E. coli*. These sequences are disclosed and described by Hoess et al., Proc. Natl. Acad. Sci. USA 79:3398 (1982), the entire disclosure of which is hereby incorporated herein by reference. Preferably, the lox site is LoxP.

One molecule of Cre binds per inverted repeat or two Cre molecules line up at one loxP site. The recombination occurs in the asymmetric spacer region. Those 8 bases are also responsible for the directionality of the site. Two loxP sequences in direct orientation dictate excision of the intervening DNA between the sites leaving one loxP site behind.

In particular, recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site.

Any nucleotides located between two lox sites (in certain embodiments of the invention, between two loxP sites) may be referred to as flanked by lox sites, or "floxed", with the Dicer1 genotype of a diploid animal containing, e.g., two lox-flanked alleles of the Dicer1 gene, referred to as, e.g., dicer1$^{flox/flox}$.

II. Constructs/Transgene

A construct is a recombinant nucleic acid, generally recombinant DNA, generated for the purpose of the expression of a specific nucleotide sequence(s), or is to be used in the construction of other recombinant nucleotide sequences. A transgene is a construct that has been or is designed to be incorporated into a cell, particularly a mammalian cell, that in turn becomes or is incorporated into a living animal such that the construct containing the nucleotide sequence is expressed (i.e., the mammalian cell is transformed with the transgene). The transgene includes a sequence (e.g., a Dicer-encoding sequence) that is endogenous to the transgenic animal. A transgene may be present as an extrachromosomal element in some or all of the cells of a transgenic animal or, preferably, stably integrated into some or all of the cells, more preferably into the germline DNA of the animal (i.e., such that the transgene is transmitted to all or some of the animal's progeny), thereby directing expression of the product of the transgene in one or more cell types or tissues of the transgenic animal. Unless otherwise indicated, it will be assumed that a transgenic animal comprises stable changes to the chromosomes of germline cells. In one embodiment, the transgene is present in the genome at a site such that it does not interfere with gene expression.

Such transgenic animals are created by introducing a transgenic construct of the invention into its genome using methods and vectors as described herein.

A transgenic construct of the invention includes the encoding sequence targeted for conditional deletion flanked by appropriate sites of inducible recombination. The transgene optionally includes selectable marker sequences, as well as promoter, enhancer and other non-coding sequences (for example, intron and/or 5' or 3' untranslated sequences).

III. Vectors and Host Cells

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Some vectors of the invention comprise a synthetic Dicer1 conditional or heterologous Dicer1 allele, or in some aspects of the invention, comprise a Cre recombinase-encoding nucleic acid operatively linked to one or more regulatory sequences (e.g., promoter sequences). The phrase "operably linked" is intended to mean that the nucleotide sequence of interest (e.g., the Cre recombinase-encoding sequence) is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Other elements included in the design of a particular expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The vectors described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al., "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al., "Techniques for human adenovirus vector construction and characterization," in Methods in Molecular Genetics, Ed. K. W. Adolph, Academic Press, Orlando, Fla., Volume 7B, pp: 12-30, 1995; Hitt, et al., "Construction and propagation of human adenovirus vectors," in Cell Biology: A Laboratory Handbook," Ed. J. E. Celis. Academic Press. pp: 479-490, 1994, also hereby incorporated by reference. The methods include, for example, stable or transient transfection, lipofection, electroporation and infection with recombinant viral vectors.

Another aspect of the invention pertains to host cells into which a host construct of the invention has been introduced, i.e., a "recombinant host cell." It is understood that the term "recombinant host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known to those skilled in the art.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders, such as disease and disorders associated with mutant or aberrant gene expression, gain-of-function mutants and neurological diseases and disorders.

The present invention is also not limited to the use of the cell types and cell lines used herein. Cells from different tissues or different species (human, mouse, etc.) are also useful in the present invention.

IV. Generation of Conditional Alleles

Often, generation of knockout mice results in an early embryonic lethal phenotype. While informative regarding the role of the targeted gene in development, analysis of the role of the gene in tissue development, aging, cancer and other diseases may be unobtainable. To circumvent this problem, researchers have begun utilizing Cre-lox technology to generate mice bearing conditional alleles, and ablating the gene function in a temporal or tissue-specific manner (Gu, H., et al. *Science* 265:103-106; Wang, Y., et al. *Proc. Natl. Acad. Sci. USA* 93:3932-3936; Shibata, H., et al. *Science* 278:120-123; Xu, X., et al. *Nat. Genet.* 22:37-43; Meuwissen, R., et al. *Exp. Cell Res.* 264: 100-110; Resor, L., et al. *Hum Mol Genet.* 10:669-675). To this end, loxP sites are introduced into the target locus flanking as much as the entire gene or as little as one exon encoding key functions. In addition, a positive selection marker must also be used in the targeting vector, and must also be flanked by loxP sites in order to permit subsequent removal of the drug cassette following identification of a properly "floxed" (flanked by loxP) gene. This is especially critical in generating conditional alleles, as expression of the floxed gene must remain unaffected by the addition of loxP sites. The loxP sites themselves may be safely inserted into introns as well as upstream or downstream of the gene, as the 34 bp loxP site has not been found to alter expression levels of the targeted gene. However, loxP sites do contain several ATG nucleotides, and researchers often prefer to introduce the loxP sites in reverse orientation with respect to transcription of the host gene to ensure that the loxP sites themselves do not induce aberrant initiation of translation.

Addition of Cre to the targeted ES cells will result in some clones that excise the drug cassette, but retain the loxP sites that flank key endogenous sequences (FIG. 3A). The ES cells are used to generate mice following identification via Southern analysis of genomic DNA of those ES clones with correct targeting. Subsequent addition of Cre to these mice will induce excision of the intervening sequences to produce a null allele. Cre may be added to the mice either by infection of the mice with recombinant viral vectors encoding for Cre (Wang, Y., et al. *Proc. Natl. Acad. Sci. USA* 93:3932-3936; Shibata, H., et al. *Science* 278:120-123), or by breeding the mice to transgenic mice expressing Cre in a known temporal or spatial manner (Xu, X., et al. *Nat. Genet.* 22:37-43; Meuwissen, R., et al. *Exp. Cell Res.* 264: 100-110; Resor, L., et al. *Hum Mol Genet.* 10:669-675). Thus, Cre-mediated gene ablation is controlled by regulating expression of Cre in the mice bearing the floxed allele. The availability of mice with well-established patterns of Cre transgene expression is crucial, and the numbers of Cre transgenic mouse lines increases with each year (see section regarding Cre transgenic mice below).

V. Construction of Conditional Knockout and Transgenic Animals

In one aspect, the present invention provides a non-human animal whose genome contains a construct or transgene of the invention comprising a conditional Dicer1 allele. The present invention further provides methods for making a transgenic non-human animal whose genome contains a Dicer1 conditional allele construct or transgene of the invention, or a Dicer1 conditional allele derived therefrom (e.g. through an inducible excision event that removes selection markers from the targeting construct while retaining a conditional Dicer1 allele, e.g. floxed exons 14, 15 and 16 of Dicer1 in certain embodiments of the invention).

The transgenic animal used in the methods of the invention can be, e.g., a mammal, a bird, a reptile or an amphibian. Suitable mammals for uses described herein include: rodents; ruminants; ungulates; domesticated mammals; and dairy animals. Commonly used animals include: rodents, goats, sheep, camels, cows, pigs, horses, oxen, llamas, chickens, geese, and turkeys. In one embodiment, the non-human animal is a mouse.

Various methods of making transgenic animals are known in the art (see, e.g., Watson, J. D., et al., "The Introduction of Foreign Genes Into Mice," in Recombinant DNA, 2d Ed., W. H. Freeman & Co., New York (1992), pp. 255-272; Gordon, J. W., Intl. Rev. Cytol. 115:171-229 (1989); Jaenisch, R., Science 240: 1468-1474 (1989); Rossant, J., Neuron 2: 323-334 (1990)). An exemplary protocol for the production of a transgenic pig can be found in White and Yannoutsos, *Current Topics in Complement Research: 64th Forum in Immunology*, pp. 88-94; U.S. Pat. No. 5,523,226; U.S. Pat. No. 5,573,933; PCT Application WO93/25071; and PCT Application WO95/04744. An exemplary protocol for the production of a transgenic rat can be found in Bader and Ganten, Clinical *and Experimental Pharmacology and Physiology*, Supp. 3:S81-S87, 1996. An exemplary protocol for the production of a transgenic cow can be found in *Transgenic Animal Technology, A Handbook*, 1994, ed., Carl A. Pinkert, Academic Press, Inc. An exemplary protocol for the production of a transgenic sheep can be found in *Transgenic Animal Technology, A Handbook*, 1994, ed., Carl A. Pinkert, Academic Press, Inc. Exemplary methods are set forth in more detail below.

A. Injection into the Pronucleus

Transgenic animals can be produced by introducing a nucleic acid construct according to the present invention into egg cells. The resulting egg cells are implanted into the uterus of a female for normal fetal development, and animals which develop and which carry the transgene are then backcrossed to create heterozygotes for the transgene. Embryonal target cells at various developmental stages are used to introduce the transgenes of the invention. Different methods are used depending on the stage of development of the embryonal target cell(s). Exemplary methods for introducing transgenes include, but are not limited to, microinjection of fertilized ovum or zygotes (Brinster, et al., Proc. Natl. Acad. Sci. USA (1985) 82: 4438-4442), and viral integration (Jaenisch R., Proc. Natl. Acad. Sci. USA (1976) 73: 1260-1264; Jahner, et al., Proc. Natl. Acad. Sci. USA (1985) 82: 6927-6931; Van der Putten, et al., (1985) Proc. Natl. Acad. Sci. (USA) 82: 6148-6152). Procedures for embryo manipulation and microinjection are described in, for example, *Manipulating the Mouse Embryo* (Cold Spring Harbor Laboratory Press, Cold Spring Harbor, N.Y., 1986, the contents of which are incorporated herein by reference). Similar methods are used for production of other transgenic animals.

In an exemplary embodiment, production of transgenic mice employs the following steps. Male and female mice, from a defined inbred genetic background, are mated. The mated female mice are previously treated with pregnant mare serum, PMS, to induce follicular growth and human chorionic gonadotropin, hCG, to induce ovulation. Following mating, the female is sacrificed and the fertilized eggs are removed from her uterine tubes. At this time, the pronuclei have not yet fused and it is possible to visualize them using light microscopy. In an alternative protocol, embryos can be harvested at varying developmental stages, e.g. blastocysts can be harvested. Embryos are recovered in a Dulbecco's modified phosphate buffered saline (DPBS) and maintained in Dulbecco's modified essential medium (DMEM) supplemented with 10% fetal bovine serum.

Foreign DNA or the recombinant construct (e.g. Dicer-encoding construct or transgene) is then microinjected (100-1000 molecules per egg) into a pronucleus. Microinjection of an expression construct can be performed using standard micro manipulators attached to a microscope. For instance, embryos are typically held in 100 microliter drops of DPBS under oil while being microinjected. DNA solution is microinjected into the male pronucleus. Successful injection is monitored by swelling of the pronucleus. Shortly thereafter, fusion of the pronuclei (a female pronucleus and a male pronucleus) occurs and, in some cases, foreign DNA inserts into (usually) one chromosome of the fertilized egg or zygote. Recombinant ES cells, which are prepared as set forth below, can be injected into blastocysts using similar techniques.

B. Embryonic Stem Cells

In another method of making transgenic mice, recombinant DNA molecules (e.g., constructs or transgenes) of the invention can be introduced into mouse embryonic stem (ES) cells. Resulting recombinant ES cells are then microinjected into mouse blastocysts using techniques similar to those set forth in the previous subsection.

ES cells are derived from the inner cell mass of a mouse blastocyst-stage embryo harvested at day 3.5 of gestation (Evans and Kaufman *Nature* 292, 154-156; Martin *Proc. Natl. Acad. Sc. USA* 78, 7634). The embryo is composed of two cell types at this stage of development: inner cell mass (ICM) cells and trophectoderm cells. The ICM is the source of ES cells, which will subsequently give rise to all embryonic tissues during development. In order to retain their pluripotency, researchers harvest and grow these ES cells in vitro under conditions that mimic the embryonic environment of the inner cell mass. ES cells are plated and grown upon a feeder layer of cells, typically either cultured or embryonic fibroblasts, in order to simulate the cell-cell contacts shared between ES cells and trophectoderm in vivo. Leukemia inhibitory factor (LIF) has been found to be important for maintenance of ES cell pluripotency (Williams et al. *Nature*, 336, 684-687; Smith et al. *Nature*, 336, 688-690). Thus, either the feeder cells are transduced with a LIF transgene, or LIF is supplied exogenously to the culture media. In addition, the feeder cells must also contain genes providing resistance to the various drugs that will be employed in the gene targeting. Regardless of whether the feeder cells are derived from embryonic tissue (mouse embryonic fibroblasts) or are a modified cell line such as STO cells (Smith and Hooper *Exp. Cell Res.* 145, 458-462), the feeder cells must be mitotically inactivated in order to prevent the cells from dividing faster than the ES cells and subsequently overwhelming the culture. Feeder cells are growth arrested by exposure either to the DNA cross-linking drug mitomycin C, or to gamma irradiation. As an alternative to using feeder cells, some ES cell lines have been adapted to grow on tissue culture plasticware in the absence of feeders, with recombinant LIF being supplied to the culture media (Pease et al. *Dev. Biol.* 141, 344-352). This avoids the need for mitotically inactivated drug-resistant feeders in order to culture and target the ES cells. However, the majority of researchers using ES cells continue to utilize a feeder cell layer, as the feeders may be supplying additional factors to the ES cells and the general consensus is that use of feeders increase the likelihood of the targeted ES cells contributing to the germline in mice.

The utility of ES cells is due not only to their ability to contribute to all tissues during development, including the germ cell layer (Bradley et al. *Nature* 309, 255-256; Gossler et al. *Proc. Natl. Acad. Sci USA* 83, 9065-9069; Robertson et al. *Nature* 323, 445; Kuehn et al. *Nature* 326, 295-298), but also to the fact that large numbers of these cells may be grown with relative ease in culture. The growth and drug selection of large numbers of ES cells means that very rare events such as homologous recombination between exogenously added DNA and an endogenous gene (approximately 1 in $10^6$ to $10^7$ cells) can be identified (Lin et al. *Proc. Natl. Acad. Sci USA* 82, 1391-1395; Smithies et al. *Nature* 317, 230-234; Doetschman et al. *Nature* 330, 576-578; Thomas et al. *Cell* 51, 503-512; Hasty et al. *Mol. Cell. Biol.* 11, 5586-5591). Furthermore, ES cell clones isolated containing these rare events can be sufficiently expanded to facilitate detailed analysis of the genetic changes in the clone. By maintaining and targeting the ES cells under rigorous culture conditions, the expanded ES cell clones will retain their pluripotency and will contribute to both the somatic and germ cell lineage upon reintroduction into mice (Robertson, in Teracarcinomas and Embryonic Stem Cells: A Practical Approach (Robertson, E. J., Ed.), pp. 71-112, IRL Press, Oxford; Bradley, in Teracarcinomas and Embryonic Stem Cells: A Practical Approach (Robertson, E. J., Ed.), pp. 113-151, IRL Press, Oxford).

C. Gene Targeting in ES and Other Cells: Knockouts and Knockins

A common approach to ablate or "knockout" gene functions in mice has been to utilize a gene replacement vector for gene targeting experiments in ES cells. (Such procedures may also be implemented, e.g., to create a Dicer1 conditional locus, in any mammalian cell line, including e.g., human cell lines.) The targeting vector typically is composed of short regions (2 to 4 Kbp) of mouse genomic DNA flanking the portion of the gene to be targeted. A drug selection marker, typically a gene encoding resistance to neomycin, hygromycin, or puromycin, is included in the construct in order to identify those ES cells that incorporate the transduced vector into the genome (Hasty, P., et al. *Mol. Cell. Biol.* 11:4509-4517; te Riele H., et al. *Proc Natl Acad Sci USA*. 89:5128-5132; Mansour, S. L., et al. *Nature* 336:348-352; Thompson, S., et al. *Cell* 56:313-321; Ramirez-Solis, R., et al. *Analytical Biochemistry* 201:331-335). Depending upon the regions of target gene homology present in the flanking arms of the vector, recombination between the vector and the targeted locus can result in deletion of some or all of the target coding sequences, which are replaced by the drug selection marker gene and any other sequences contained within the replacement portion of the vector (e.g., Dicer1 gene sequence comprising exons 14, 15 and 16 in certain embodiments of the instant invention).

Diploid cells containing Dicer1 conditional alleles at both genomic Dicer1 loci may optionally be created following initial integration of a Dicer1 conditional allele. Such a cell line may be subjected to a second round of selective integration of a conditional Dicer1 allele, by a similar process as employed for initial integration of a conditional Dicer1 allele, though selecting with a marker distinct from that used to monitor integration of the initial Dicer1 conditional allele. Such procedures will most often be employed to generate cell lines for a conditional Dicer1 allele directly, as non-human animals harboring conditional Dicer1 alleles will most often be generated by traditional methods of creating heterozygous founder animals, then homozygosing such alleles through directed matings.

Any ES cell line that is capable of integrating into and becoming part of the germ line of a developing embryo, so as to create germ line transmission of the targeting construct, is suitable for use herein. For example, a mouse strain that can be used for production of ES cells is the 129J strain. One ES cell line is murine cell line D3 (American Type Culture Collection catalog no. CRL 1934). The ES cells can be cultured and prepared for DNA insertion using methods known in the art and described in Robertson, *Teratocarcinomas and Embryonic Stem Cells: A Practical Approach*, E. J. Robertson, ed. IRL Press, Washington, D.C., 1987, in Bradley et al., *Current Topics in Devel. Biol.*, 20:357-371, 1986 and in Hogan et al., *Manipulating the Mouse Embryo: A Laboratory Manual*, Cold Spring Harbor Laboratory Press, Cold Spring Harbor, N.Y., 1986, the contents of which are incorporated herein by reference.

The expression construct can be introduced into the ES cells by methods known in the art, e.g., those described in Sambrook et al., *Molecular Cloning: A Laboratory Manual*, $2^{nd}$ Ed., ed., Cold Spring Harbor laboratory Press: 1989, the contents of which are incorporated herein by reference. Suitable methods include, but are not limited to, electroporation, microinjection, and calcium phosphate treatment methods. The foreign DNA (e.g. construct or transgene) to be introduced into the ES cell is preferably linear.

After introduction of the expression construct, the ES cells are screened for the presence of the construct. The cells can be screened using a variety of methods. ES cell genomic DNA can be examined directly. For example, the DNA can be extracted from the ES cells using standard methods and the DNA can then be probed on a Southern blot with a probe or probes designed to hybridize specifically to the transgene. The genomic DNA can also be amplified by PCR with probes specifically designed to amplify DNA fragments of a particular size and sequence of the construct or transgene such that, only those cells containing the construct or transgene will generate DNA fragments of the proper size. Where a marker gene is employed in the construct, the cells of the animal can be tested for the presence of the marker gene. For example, where the marker gene is an antibiotic resistance gene, the cells can be cultured in the presence of an otherwise lethal concentration of antibiotic (e.g., G418 to select for neo). Those cells that survive have presumably integrated the transgene construct. If the marker gene is a gene that encodes an enzyme whose activity can be detected (e.g., β-galactosidase), the enzyme substrate can be added to the cells under suitable conditions, and the enzymatic activity can be analyzed.

A gene replacement vector may integrate into the ES cell genome either at the desired target locus via homologous recombination or randomly in the host genome (non-homologous recombination). In general, the frequency of targeted integration is several orders of magnitude less than the frequency of random integration (Mansour, S. L., et al. *Nature* 336:348-352). This ratio of targeted integration versus random integration will determine the ease with which a properly-targeted clone can be identified. Factors which have been found to influence the frequency of homologous recombination include the length of homology shared between the vector and the targeted gene, the degree of polymorphic variation between the vector and the target sequences, and the confluency of the ES cells at the time of transduction (Thomas, K. R. and Capecchi, M. R. *Cell* 51:503-512; Hasty, P., et al. *Mol. Cell. Biol.* 11:5586-5591; Hasty, P., et al. *Mol. Cell. Biol.* 11:4509-4517). Although the frequency of homologous recombination is low ($10^{-6}$), the ratio of targeted events to random integrants can be enriched by including a negative selection marker in the vector. Placing this negative selection marker at either end of the homologous sequences permits selection against random integration events that favor inclusion of the negative marker into the host genome (Mansour, S. L., et al. *Nature* 336:348-352). Proper homologous recombination between the targeting vector and the endogenous gene should result in loss of the negative selection cassette, usually the herpes simplex virus thymidine kinase (HSV-tk), yielding clones that are tk minus and therefore survive the negative drug selection (gancyclovir). Thus, the use of appropriate drug resistance cassettes in the gene replacement vector and positive-negative drug selection of the ES cells following transduction of the targeting vector increases the likelihood of recovering properly targeted clones.

Following growth of the ES cell clones in the appropriate selection media; colonies are usually picked from the plates and arrayed into 96-well tissue culture plates that were pre-seeded with inactivated feeder cells. These clones are expanded and a portion of each clone is frozen down, while the rest of the cells are passed onto plates lacking the feeder cell layer to avoid subsequent DNA contamination from the feeder cells. Genomic DNA is prepared from the ES cell clones for Southern or PCR-based analysis. The use of PCR has the advantage that a large number of clones may be screened and that fewer cells are needed per clone to give adequate DNA for screening. Furthermore, the PCR analysis may be done on pools of clones (Joyner, A. L., et al. Nature 338:153-156). Typically, the one primer for the PCR would anneal to DNA sequences included in the targeting vector and the other primer of the pair would recognize genomic sequences that are outside (or external) to the flanking sequences present in the vector (McMahon, A. P., and Bradley A. Cell 62:1073-1085; Soriano, P. et al. Cell 64:693-702; Thompson, S., et al. Cell 56:313-321). However, these assays run the risk of having significant numbers of false positives and negatives, making it difficult to identify properly targeted clones, and DNA sequence information must be obtained in order to generate the primer pair. Often, the relative targeting frequencies of genes in ES cells are sufficient to permit Southern analysis to be performed on genomic DNA isolated from each clone—either in a 96 well format or following expansion of the clones to larger wells. By using a portion of the targeted locus that is not present on the targeting vector, it is possible to screen for the presence of a junction fragment of anticipated size following endonuclease digestion of the genomic DNA (Ramirez-Solis, R., et al. Analytical Biochemistry 201: 331-335). This method of analysis is more reliable than PCR-based methods and does not require identification of the DNA sequence, but rather a simple restriction map of the locus. However, it does require more DNA, and most researchers often use a combination of both approaches in order to analyze their clones.

A variation on the gene targeting knockout strategy is to engineer the gene replacement vector so that a reporter gene encoding an easily assayable product (such as green fluorescence protein or β-galactosidase), but lacking eukaryotic promoter elements is introduced into the targeted gene locus along with the positive selection marker. Proper integration of this vector by homologous recombination serves not only to ablate the targeted gene function, but also places the reporter gene included in the construct under transcriptional control of the endogenous gene promoter elements. Assaying the pattern of marker gene expression in mice derived from these ES cells containing a reporter gene "knockin" can greatly facilitate promoter analysis of the targeted gene in addition to generating a knockout allele (for examples, see Vaulont, S., et al. Transgenic Res. 4:247-255; Tajbakhsh, S., et al. Dev. Dyn 206:291-300).

Knockin strategies have proven very useful in placing gene coding sequences under the transcriptional control of specific heterologous promoter regions. A cDNA encoding a protein of interest may be included in the knockin construct in lieu of a reporter gene. Recombination of the knockin vector with the target locus would result in expression of the cDNA being regulated by the target locus (Wang, Y., et al. Nature 379:823-825). Although more time-consuming and laborious than the classic pronuclear microinjection approach to generating transgenic mice, the ES cell knockin strategy is superior in that transgene copy number is strictly regulated and expression of the transgene is not altered by positional effects of integration. Furthermore, all upstream and downstream elements that might contribute to regulation of gene expression are present at the knockin locus, whereas only those elements included in the transgene construct will contribute to regulation of gene expression in the transgenic mice.

Using a similar approach, researchers have performed knockin experiments to replace portions of the endogenous targeted gene with a similar region of the gene encoding several base pair changes or even a single point mutation. This strategy facilitates the introduction of single nucleotide alterations into a target gene without altering the chromosomal location of the gene, thus expression levels should precisely copy that of the endogenous wildtype allele, thereby permitting mouse modeling of point mutations observed in human patients (for example, see Wang, Y., et al. Nature 379:823-825). Furthermore, the use of ES cell knockin technology allows structure-function experiments to be performed in vivo in ES cells and in mice (Jimenez, G. S., et al. Nat Genet. 26:37-43).

Once the properly targeted ES cell clone is identified by its ability to survive drug selection, and proper targeting is confirmed by Southern analysis of genomic DNA isolated from the clone, a Cre cassette may be electroporated into the ES cell clone in order to excise the positive selection cassette. The Cre cassette usually contains a eukaryotic promoter driving expression of the bacteriophage Cre gene, which encodes for Cre fused to a eukaryotic nuclear localization signal. Transient expression of cre in ES cells mediates highly efficient recombination of the loxP sites, thereby deleting the drug selection cassette from the targeted locus. Following confirmation of proper Cre-mediated excision of the marker (either by Southern analysis or PCR experiments using ES clone genomic DNA), the ES cells are used to generate mice. This methodology allows the introduction of subtle mutations into a targeted locus without additional alterations or complications arising from nearby placement of a strong promoter or marker gene. This methodology also allows for subsequent utilization of the excised marker in other gene targeting vector if a second round of gene targeting in the ES clone is desired (Abuin, A. and Bradley, A. Mol. Cell. Biol. 16:1851-1856). This recycling of markers is particularly useful as only a handful of drug selection cassettes have been found to work well in ES cells, and most feeder cells used to grow and target ES cells are resistant to only a few of the drugs.

Addition of the Cre cassette to targeted ES cells necessitates a second round of electroporation, which increases the risk that the ES cells might lose their totipotency. Furthermore, since approximately 1-5% of ES cells are transduced following electroporation, many of the electroporated cells will lack the desired excision of the positive selection marker. To circumvent this problem, researchers often include a negative selection marker such as the HSV tk gene in addition to the positive selection cassette flanked by loxP sites. Once the targeted clone is electroporated with the Cre cassette, the cells are placed on negative drug selection media (gancyclovir) to select only for those clones that have expressed Cre and excised sequences between the loxP sites. While this greatly enhances the likelihood of recovery of properly targeted and Cre-excised clones, the use of this approach means that the HSVtk gene can no longer be used as a negative selection cassette in the initial gene targeting. Recently, ES cells bearing a stable, integrated Cre transgene under transcriptional control of the mouse Protamine gene promoter (O'Gorman S, et al. *Proc. Natl. Acad. Sci U.S.A.* 94:14602-14607) have been used in gene targeting experiments to introduce subtle gene mutations into the p53 gene (Jimenez, G. S., et al. *Nat Genet.* 26:37-43). Because Cre did not have to be added exogenously to the ES cells, the negative selection marker could be used at the end of one arm of homology to aid in identification of properly targeted clones. Once ES clones were identified that contained the subtle mutations (as well as the positive selection marker flanked by loxP sites), introduction of the ES cells into mice resulted in excision of the positive selection cassette in the sperm of males, where expression of the protamine transgene was induced. Alternatively, the ES cells bearing the floxed positive marker cassette could be used to generate chimeric mice, which are then mated with transgenic mice that express Cre, in order to excise the marker gene (Schwenk, F., et al. *Nucleic Acids Res.* 23:5080-5081; Lakso, M., et al. *Proc. Natl. Acad. Sci U.S.A.* 93:5860-5865). However, this approach requires production of an additional generation of mice in order to obtain the properly targeted locus in mice.

Cre-lox technology has also been used in ES cells to generate deletions of endogenous sequences, including entire genes and gene clusters (Ramirez-Solis, R., et al. *Nature* 378:720-724; Zheng, B., et al. *Mol Cell Biol.* 2:648-655). The targeting of one locus with a knockin vector that contains half of a functional hypoxanthine phosphoribosyltransferase (hprt) mini-gene and a loxP site is followed by the targeting a second gene lying (in cis) on the same chromosome with a knockin vector that introduces the other half of the hprt minigene, plus a second loxP site. Subsequent addition of a Cre vector to these cells results in deletion of sequences lying between the loxP sites and results in the two halves of the hprt minigene being brought together. Thus, hprt-minus ES cell can be selected in HAT media to select for those clones that contain the reconstructed hprt minigene. This type of approach has been used recently to generate ES cells deleted for megabase pair length regions of DNA. The use of these modified ES cells to generate mice haploinsufficient for large regions of DNA should assist in identifying tumor suppressor genes that lie within the region in question. Haploinsufficient mice can be mutagenized with chemicals such as ethylnitrosourea (ENU), or infected with retroviruses to insertionally-inactivate genes (reviewed in 67,68). Tumorigenesis in these mice would likely be a byproduct of mutation of genes in the remaining wildtype allele corresponding to the region of DNA excised in the ES cells by Cre, as these mice do not have to undergo loss of heterozygousity for genes in the defined region following an initial mutagenic event.

D. Implantation

The zygote containing a recombinant nucleic acid molecule of the invention (e.g., construct or transgene) is implanted into a pseudo-pregnant female mouse that was obtained by previous mating with a vasectomized male. In a general protocol, recipient females are anesthetized, paralumbar incisions are made to expose the oviducts, and the embryos are transformed into the ampullary region of the oviducts. The body wall is sutured and the skin closed with wound clips. The embryo develops for the full gestation period, and the surrogate mother delivers the potentially transgenic mice. Finally, the newborn mice are tested for the presence of the foreign or recombinant DNA. Of the eggs injected, on average 10% develop properly and produce mice. Of the mice born, on average one in four (25%) are transgenic for an overall efficiency of 2.5%. Once these mice are bred they transmit the foreign gene in a normal (Mendelian) fashion linked to a mouse chromosome.

E. Generating Chimeric Mice Using Targeted ES Cells

Two different approaches have been successfully used to introduce targeted mutations in ES cells into the germline of mice. In the first method, blastocyst embryos are harvested from pregnant female mice at day 3.5 post coitus (p.c.) by flushing the uterus with media (Bradley, A. in *Teracarcinomas and Embryonic Stem Cells: A Practical Approach* (Robertson, E. J., ed.), pp. 113-151, IRL Press, Oxford, UK). Approximately 15 targeted ES cells are microinjected into each blastocyst using a finely-drawn glass needle. Following microinjection, the blastocysts are surgically implanted into the uterus of a pseudopregnant female mouse that had been previously mated with a vasectomized male. These foster mothers will give birth 17 days after transplantation of the blastocysts. Chimeric mice can also be generated using targeted ES cells by morula aggregation. Eight cell stage (day 2.5 p.c.) embryos are harvested from the oviduct of C57Bl/6 pregnant females, and treated with a mild acid-saline solution to dissolve the outer zona pellucida membrane. Two of these non-compacted embryos are placed in a small indentation in a tissue culture dish, along with a clump of targeted ES cells, and cultured overnight. This indentation was produced originally by pressing a darning needle into the plastic culture dish, giving rise to the nickname the "darning needle" method. Once the inner cell mass of the embryos and the ES cells have fused and undergone compaction, the resulting blastocysts are surgically implanted into the uteri of pseudopregnant female mice permitting subsequent development of chimeric mice. Although this procedure may be less efficient in generating chimeras compared to blastocyst injection of ES cells, morula aggregation does have the advantage of not requiring an expensive injection microscope or quite as much training and practice in microinjection (Wood S A, et al. *Nature* 365, 87-89).

Regardless of the approach used to generate chimeras, the chimeric mice are analyzed and bred similarly. Since the ES cells were originally derived from the inner cell mass of a 129-strain mouse blastocyst, they will colonize the inner cell mass of the injected blastocyst and contribute to the formation of the resulting mouse. Since the inner cell mass of the recipient blastocyst is not removed, the resulting mouse will be a chimeric, with endogenous and exogenously-added ES cells contributing to formation of the embryo. The amount of contribution of the injected ES cells to the resulting chimeric mouse can be estimated by the color of the fur: 129 strain mice are homozygous for agouti (brown) coat coloration, whereas the recipient blastocysts are usually harvested from non-agouti (black), C57Bl/6 mice. Therefore, the chimeric mice will have a mixed coat color, with the amount of agouti present in the coat of the chimeric mice serving as a rough indicator of the degree of chimericism. Germline contribution of the targeted and injected ES cells can be determined by crossing the chimeric mice with a C57Bl/6 mouse and scoring the offspring for the presence of agouti mice, as agouti is a dominant trait. The agouti F1 mice have a 50% chance of inheriting the targeted allele from the chimeric parent, and can be scored for the presence of the targeted allele by Southern or PCR-based analysis of genomic DNA isolated from tail biopsy. Mice that are heterozygous for the targeted allele can be intercrossed to obtain homozygous-targeted mice.

F. Screening for the Presence of the Transgenic Construct

Transgenic animals can be identified after birth by standard protocols. DNA from tail tissue can be screened for the presence of the transgene construct, e.g., using southern blots and/or PCR. Offspring that appear to be mosaics are then crossed to each other if they are believed to carry the transgene in order to generate homozygous animals. If it is unclear whether the offspring will have germ line transmission, they can be crossed with a parental or other strain and the offspring screened for heterozygosity. The heterozygotes are identified by southern blots and/or PCR amplification of the DNA. The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed based on the sequence of the construct or transgene, or a marker gene, or both.

Other means of identifying and characterizing the transgenic offspring are known in the art. For example, western blots can be used to assess the level of expression of a gene targeted for interference by probing the with an antibody against the protein encoded by the target gene. Alternatively, an antibody against a marker gene product can be used, when a marker gene is expressed.

G. Mice Containing Multiple Transgenes

Transgenic mice containing "floxed" genomic alleles of Dicer1 as described herein can be crossed with mice that contain additional transgene(s). Mice that are heterozygous or homozygous for floxed genomic alleles of Dicer1 can be generated and maintained using standard crossbreeding procedures. One aspect of the invention features crossing mice that contain a conditional Dicer1 allele regulatable by a recombinase with mice expressing a corresponding recombinase. In a specific embodiment, mice that contain floxed Dicer1 sequences, as described herein, are crossed with mice expressing Cre. Such Cre expressing mice are known in the art and are publicly available, for example, from the Jackson Laboratory (Bar Harbor, Me.) or from Taconic.

The invention further pertains to cells derived from transgenic animals. Because certain modifications may occur in succeeding generations due to either mutation or environmental influences, such progeny may not, in fact, be identical to the parent cell, but are still included within the scope of the term as used herein.

VI. Cre Transgenic Mice

Animals of the instant invention that contain a conditional allele of Dicer1 in some embodiments, mice that are either heterozygous (dicer1$^{+/flox}$ or dicer1$^{flox/-}$) or homozygous (dicer1$^{flox/flox}$) for the conditional (foxed) Dicer1 allele—can be bred with animals transgenic for the bacteriophage P1 Cre recombinase, as one method for effecting temporally- and/or spatially-directed elimination of Dicer expression in specific cells, tissues or organs of the animal. Restricted expression of Crc recombinase in animals containing foxed alleles of Dicer1 will enable generation and characterization of animals possessing no, or in the case of animals of genotype dicer1$^{+/flox}$, only one functional allele of Dicer1 in only those cells expressing the Cre recombinase. Many lines of mice transgenic for Cre expression in temporally- and/or spatially/tissue-directed patterns are publicly/commercially available (for an extensive listing of a number of such Cre transgenic mice, refer, for example, to those produced by the Samuel Lunenfeld Research Institute.

In certain embodiments of the instant invention, disruption of the Dicer1 gene in all tissues with the exception of a small number of protected tissues might be desirable. Such tissue-specific protection from disruption of an otherwise globally disrupted Dicer1 allele may be achieved through e.g., Cre expression systems that are additionally under the control of e.g., tissue specific repressors.

Additional detail and protocols for generating transgenic mice either through microinjection of oocytes or blastocysts, or the culturing and growth of embryonic stem cells, may be found in any of a number of manuals on these subjects [e.g. Hogan, B. et al. (1994). *Manipulating the Mouse Embryo: A Laboratory Manual* (2$^{nd}$ *Edition*). Cold Spring Harbor Laboratory Press, Plainview, N.Y.; Ramirez-Solis, R. et al. (1993) in Methods in Enzymology: Guide to Techniques in Mouse Development (Wasserman, P. M., and DePamphilis, M. L., Ed.) pp 855-877, Academic Press, Inc., San Diego; Tymms, M. J. and Kola, I. (2001). *Gene Knockout Protocols. Methods in Molecular Biology, Vol.* 158. Humana Press, Totowa, N.J.; Kmiec, E. B. (2000). *Gene Targeting Protocols. Methods in Molecular Biology, Vol.* 137. Humana Press, Totowa, N.J.; Joyner, A. L. (2000). *Gene Targeting: A Practical Approach,* 2$^{nd}$ ed. Oxford University Press, Oxford].

VII. Uses of the Animals, Cells and Methods of the Invention

In one embodiment, the animals of the invention are used as models for inducible Dicer1/RNAi pathway deficiency. Dicer is a critical component of the RNAi pathway, thus conditional disruption of Dicer can also conditionally disrupt the RNAi pathway in a spatially- and temporally-controlled manner. Such spatial and temporal control of Dicer function can be achieved via directed manipulation of exposure to and/or expression of an inducing agent (e.g., Cre recombinase) in cells and animals of the instant invention comprising at least one conditional allele of Dicer1. Animals with spatially- and temporally-controlled expression of recombinases such as Cre have been described in the art, and animals and/or cell lines of the invention containing both a conditional Dicer1 allele and e.g., a Cre transgene may be produced by standard mating and/or selection techniques.

The animals of the invention are generally useful to study the role of Dicer in various biological processes, including embryonic development, tissue differentiation and function, etc. The process by which developmental abnormalities in particular are assessed in Dicer1 conditional animals initially involves attempts to generate animals homozygous for the Dicer1 conditional allele(s) of the invention.

For developmental assessment of Dicer1 conditional mice, once mice heterozygous for a germ-line inducible conditional allele of Dicer1 are generated, they are crossed to each other in an attempt to generate offspring nullizygous for the mutation. Knockout of both germline Dicer1 alleles has been shown to confer embryonic lethality (Bernstein et al. *Nature Genetics* 35: 215-217). The development of embryonic lethality occurs early in the 19 day gestation period (e.g., E7.5 day embryos homozygous for a mutant Dicer1 allele are both underrepresented relative to Mendelian expectations and those Dicer1-null embryos present are morphologically abnormal; Bernstein et al. *Nature Genetics* 35: 215-217). Conditional knockout of Dicer1 in temporal- and tissue-specific fashion is anticipated to allow for enhanced evaluation of the role of Dicer1 function in development.

The initial test of an embryonic lethal condition is to simply determine the genotypes of the offspring of heterozygote crosses at weaning if there are no obvious morphological abnormalities among the weanlings. If there is a significant reduction in the numbers of nullizygotes obtained, or no nullizygotes among the offspring, and the neonates are consistently healthy, then an embryonic lethal condition exists. If the neonates do die frequently, this may be indicative of a perinatal lethality effect. In this case, a thorough pathological analysis of both abnormal and normal control neonates should be undertaken. This should be done in collaboration with a skilled veterinary pathologist or mouse embryologist. Useful reference books on the anatomy of the various mouse organ systems can be helpful here (Rugh, R. *The Mouse: Its Reproduction and Development*. Oxford Science Publications, Oxford, UK; Kaufman, M. H. and Bard, J. B. L. *The Anatomical Basis of Mouse Development*. Academic Press, New York, N.Y.; Hogan, B., et al., *Manipulating the Mouse Embryo: A Laboratory Manual* ($2^{nd}$ Edition). Cold Spring Harbor Laboratory Press, Plainview, N.Y.).

If viable nullizygotes are not obtained, the next step is to analyze progressively earlier stage embryos. Pregnant mothers in heterozygous crosses may be sacrificed, e.g., at day 10.5 to 12.5 post-coitus. Days post-coitus are measured from a morning observation of vaginal plugs in mating females. The presence of a vaginal plug corresponds corresponds to day 0.5 (at noon) of embryonic development (Hogan, B., et al. in *Manipulating the Mouse Embryo: A Laboratory Manual* ($2^{nd}$ Edition). Cold Spring Harbor Laboratory Press, Plainview, N.Y.). Once the pregnant mothers are sacrificed, the individual embryos are removed and examined after cutting a small tail segment for DNA analyses. The embryos can then be fixed and sectioned in order to detect more subtle defects in organogenesis. If defects are observed in roughly one quarter of the embryos, then PCR genotyping of DNA from the tail biopsies can confirm that the defective embros are indeed null for the targeted gene.

If no defective or nullizygous embryos are observed at midgestation, then earlier embryo analyses must be performed. Typically, embryos would then be examined at day 8.5 p.c. because the dissections are easily performed, the embryo readily separated from the maternal deciduum, and the yolk sac (which is embryonic in origin) yields enough DNA for PCR or even Southern analysis, facilitating genotyping of each embryo. Furthermore, defects in gastrulation (day 6.5 p.c.) or turning of the embryo (day 8 p.c.) are often reflected by an aberrant morphology at day 8.5 (93). If no null embryos are recovered at day 8.5, one is faced with a series of dissections that must be performed at various days earlier in the gestation of the embryo in order to document the phenotype. Initially, flushing the uteri of pregnant heterozygous females that have been mated with heterozygous males may be performed in order to recover blastocyst-stage embryos at day 3.5 p.c. Although genotyping of embryos at this stage requires a PCR-based method and the use of the entire embryo to generate sufficient genomic DNA for use in the PCR reaction, the embryos are easily removed from the females and may be photo-documented or allowed to develop further in vitro before genotyping. Absence of null blastocysts or inability of the blastocysts to adhere to tissue culture plasticware and expand in culture indicates a very early phenotype, such as was observed recently in Ini1 tumor suppressor-null embryos (Guidi, C., et al. *Mol. Cell. Biol.* 21:3598-3603). In contrast, the presence of healthy null blastocysts would also provide a rationale for harvesting and scoring embryos for nullizygosity between day 4 (implantation) and day 8.5 p.c.

Egg-cylinder stage embryos may be harvested from female partners of timed matings at day 6.5 and 7.5 and dissected free of the maternal deciduum with some little practice. An ectoplacental cone, an extra-embryonic tissue that is fetal in origin and will give rise to the placenta, caps these embryos. This structure may be removed and genotyped by PCR to identify any null embryos. Embryos harvested between day 4 and 6.5 p.c. are more difficult to free from the surrounding maternal decidua without damaging embryonic morphology, and these embryos are generally left in their individual deciduum during harvest. The entire embryo is usually fixed and sectioned for histologic analysis, precluding any definitive genotyping of the embryo. However, if one quarter of the embryos display an aberrant phenotype, it is customary to assume that these embryos are the nulls. If uncertainty persists, some sections may be taken from the embryos and genotyped on the slide via PCR. While the day 4-day 6 p.c. timepoint in development is probably the most challenging time to analyze the phenotype of a null embryo, ablation of many genes involved in DNA recombination and repair, tumor suppression, and modifiers of tumor suppressor functions result in lethality during this period of development (Jones, S. N., et al. *Nature* 378:206-208). However, information can be gleaned, even from these early lethal embryos, by using a combination of careful structural analysis (histology), DAPI staining or TUNEL assays for aberrant apoptosis, BrdU incorporation to document cell proliferation, and antibody staining to observe the formation of the three tissue lineages (Kaufman, M. H. and Bard, J. B. L. *The Anatomical Basis of Mouse Development*. Academic Press, New York, N.Y.; Hogan, B., et al., *Manipulating the Mouse Embryo: A Laboratory Manual* ($2^{nd}$ Edition). Cold Spring Harbor Laboratory Press, Plainview, N.Y.; Kaufman, M. H. in *Pathology of Genetically Engineered Mice*, Ward, J. M. (ed)., Iowa State University Press, Ames, Iowa, pp. 63-88; Maronpot, R. R., et al. in *Pathology of Genetically Engineered Mice*, Ward, J. M. (ed)., Iowa State University Press, Ames, Iowa, pp. 45-62).

The Dicer1 conditional animals of the invention may be bred with, e.g., recombinase-expressing animals and animals expressing heterologous forms of Dicer, to produce animals with precisely controlled tissue- and temporal-specific patterns of Dicer1 expression (and therefore precisely controlled RNAi pathway activity). Such animal models of manipulable RNAi pathway activity will have significant commercial and research interest to any individual or group developing siRNA-based and RNAi pathway therapeutics.

Cells and/or animals of the present invention may also be suitable for use in methods to identify and/or characterize potential pharmacological agents, e.g. identifying new pharmacological agents from a collection of test substances and/or characterizing mechanisms of action and/or side effects of known pharmacological agents. Such testing of pharmacological agents in animals and cells containing Dicer1 conditional alleles is of particular use in identifying compounds that modulate the RNAi pathway and/or RNAi agent activity.

The present invention therefore also relates to a system for identifying and/or characterizing pharmacological agents comprising: (a) a cell (e.g., a eukaryotic cell) or organism (e.g., a eukaryotic non-human organism) containing a construct or transgene of the invention and (b) a test substance or a collection of test substances wherein pharmacological properties of said test substance or said collection are to be identified and/or characterized. Optionally, the system as described above can further comprise suitable controls.

Test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993)

Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.)).

In one embodiment, the library is a natural product library, e.g., a library produced by a bacterial, fungal, or yeast culture. In another embodiment, the library is a synthetic compound library.

Compounds or agents identified according to such screening assays can be used therapeutically or prophylactically either alone or in combination.

Of particular use in performance of such screening assays, the animals of the invention, or cells derived therefrom, are used as positive control animals by which to evaluate the efficacy of Dicer/RNAi pathway inhibitors. That is, the homozygous animals of the invention can provide a temporal- or tissue-specific standard for 100% Dicer1/RNAi pathway disruption. In a screening assay to identify and assess the efficacy of Dicer inhibitors, a wild type animal (or cells derived therefrom) not treated with the inhibitor can be used as the 0% inhibition standard, an animal heterozygous for a Dicer1 conditional allele (or cells derived therefrom) can be used, following recombinase-induced excision of targeted Dicer1 sequence, as the 50% inhibition standard and an animal homozygous for an the Dicer1 conditional allele (or cells derived therefrom) can be used as the 100% inhibition standard, again following recombinase-induced excision of targeted sequences. The amount of Dicer and/or RNAi pathway activity in a subject treated with a Dicer inhibitor is then assessed relative to these standards.

The animals of the invention, or cells derived therefrom, also can be used to screen Dicer inhibitors for side effects or toxicity resulting from the inhibitor's action on a target(s) other than Dicer itself. General methods for evaluating the toxicity (e.g., pharmaceutical toxicity, tissue-specific, e.g., liver-specific, toxicity, etc.) of a compound are well known in the art. In certain embodiments, a Dicer inhibitor is administered to an animal of the invention homozygous for a Dicer1 conditional allele in which recombinase-mediated excision of critical sequences has been induced and the resulting effects are monitored to evaluate side effects or toxicity of the inhibitor. Since the animal lacks the normal target of the Dicer inhibitor (i.e., active Dicer protein), an effect observed upon administration of the inhibitor to the disrupted Dicer1 conditional allele can be attributed to a side effect of the Dicer inhibitor on another target(s) (e.g., a Dicer isoform). Accordingly, the animals of the invention are useful for distinguishing these side effects from the direct effects of the inhibitor on Dicer activity.

The animals of the invention can also be used in in vivo screening assays to identify diseases in which Dicer and/or the RNAi pathway play a role in the pathogenesis of the diseases. Such screening assays are further useful for identifying diseases that may be treated by Dicer inhibitors. To identify a disease condition involving Dicer and/or the RNAi pathway, and thus potentially treatable by a Dicer inhibitor, a disease condition is induced in an animal of the invention homozygous for the disrupted Dicer1 conditional allele. In one embodiment, the induction of the disease condition involves administering a stimulus to the animal that induces the disease condition in a wild-type animal (e.g., induction of rheumatoid arthritis through administration of type II collagen in Freund's adjuvant, transplantation of lymphmoma or other cancer to a subject animal, etc.). In another embodiment, the attempt to induce the disease condition involves breeding an animal of the invention with another animal genetically prone to a particular disease. The animals are crossbred at least until they are homozygous for the Dicer1 conditional allele. Useful animal models are well-known and include but are not limited to models for Alzheimer's disease (AD, e.g., ApoE, presenilin mutant mice), diabetes (e.g., Insulin receptor, PPARy, etc. mutant mice), ALS, heart disease, autoimmune diseases, numerous forms of cancer, etc. Mouse models for a wide range of diseases can be found at least at http://jaxmicejax.org.

To perform in vivo screening assays with animals of the instant invention, for example, an animal of the invention can be bred with an animal prone to a particular autoimmune disease to assess the involvement of Dicer in the pathology of the autoimmune disease and to determine whether a Dicer inhibitor is effective in treating the autoimmune disease. Examples of mouse strains genetically susceptible to particular autoimmune diseases include the MRL/lpr mouse (Cohen, P. L. et al. (1991) Ann. Rev. Immunol. 9:243-269), which is a model for lupus erythematosus, and the NOD mouse (Rossinni, A. A. (1985) Ann. Rev. Immunol. 3:289-320), which is a model for insulin-dependent diabetes mellitus. Non-limiting examples of other mouse strains (and their disease susceptibilities) which can be bred with the animals of the invention include: DBA/1 (collagen-induced arthritis; model for rheumatoid arthritis; Wooley, P. H. et al. (1981) J. Exp. Med. 154:688-700), BALB/c (proteoglycan-induced arthritis and spondylitis; model for rheumatoid arthritis and ankylosing spondylitis; Glant, T. T. et al. (1987) Arthritis Rheum. 30:201-212), PL/J (experimental autoimmune encephalomyelitis; model for multiple sclerosis; Fritz, R. B. et al. (1983) J. Immunol. 130:191-194), NZB/KN (polyarthritis; model for rheumatoid arthritis and osteoarthritis; Nakamura, K. et al. (1991) Arthritis Rheum. 34:171-179), C57BL (osteoarthritis; Pataki, A. et al. (1990) Agents Actions 29:201-209), STR/ORT (polyarthritis; model for rheumatoid arthritis and osteoarthritis; Dunham, J. et al. (1990) J. Orthop. Res. 8:101-104), and Tsk/+ (systemic sclerosis; Siracusa, L. D. et al. (1993) Genomics 17:748-751). For MHC-associated disease models, offspring of the crossbreeding are selected that maintain the disease-susceptible MHC haplotype. Many mouse strains genetically susceptible to particular diseases are available from The Jackson Laboratory, Bar Harbor, Me. or other commercial or academic sources. The disease condition is then induced in the crossbred animals either spontaneously or experimentally.

Following induction of the disease condition in the Dicer1 conditional animal, the susceptibility or resistance of the animal to the disease condition is determined. Resistance of the animal to the disease condition, relative to a wild-type control animal, is indicative that the pathology of the disease condition involves Dicer and thus that the disease condition is treatable with an Dicer inhibitor.

In another embodiment, an animal of the invention homozygous for a Dicer1 conditional allele, or a cell derived therefrom, is reconstituted with a human Dicer1 gene or human conditional Dicer1 gene of the invention to create a nonhuman cell or animal that expresses a human Dicer1 gene product (described above). These cells and animals can then be used to screen compounds to identify agents that inhibit the activity of human Dicer, either in cultured cells or in vivo in animals. For example, a panel of compounds can be administered individually to the animal conditionally disrupted for genomic Dicer1 and the level of human Dicer activity in the animal can be measured. Decreased human Dicer activity in the animal in the presence of an agent, as compared to human Dicer activity in the animal in the absence of the agent, is indicative that the agent inhibits human Dicer in vivo.

The animals of the invention can also used to create additional animals having multiple mutations. In one embodiment, an animal of the invention is bred with an animal carrying another null mutation(s) to create double (or triple, etc.) knockout animals. In another embodiment, an animal of the invention is used to create an embryonic stem cell line into which targeting vectors for functional manipulation/disruption of additional genes can be introduced. In such a manner, animals having multiple deficiencies in molecules involved in signal transduction can be created, to assess the roles of these molecules in signal transduction.

The Dicer1 conditional animals also can be bred with other knockout or transgenic animals to examine the role of the deficient gene products in various disease conditions. Non-limiting examples of knockout and transgenic animals known in the art (and their disease susceptibilities) which can be bred with the animals of the invention to examine disease states include: interleukin-2 (IL-2) knockout (inflammatory bowel disease; Sadlack, B. et al. (1993) *Cell* 75:253-261), T cell receptor knockouts (inflammatory bowel disease; Mombaerts, P. et al. (1993) *Cell* 75:275-282), Major Histocompatibility Complex (MHC) Class II knockout (inflammatory bowel disease; Mombaerts, P. et al. (1993) *Cell* 75:275-282), interleukin 10 (IL-10) knockout (inflammatory bowel disease; Kuhn, R. et al. (1993) *Cell* 75:263-274), TGFβ1 knockout (multi-organ inflammation; Shull, M. M. et al. (1992) *Nature* 359:693-699), TNFα transgenic (arthritis; Keffer, J. et al. (1991) *EMBO J.* 10:4025-4031) and TNFα transgenic-T cell specific (systemic toxicity of TNFα; Probert, L. et al. (1993) *J. Immunol.* 151:1894-1906). A disease condition can be induced spontaneously or experimentally in the double (triple, etc.) conditional/knockout or transgenic animals to assess the involvement of the affected gene products in the disease.

One useful aspect of animals with targeted germ line mutations is the ability to derive cells from virtually any tissue of the mutant mouse to study the effects of the deficiency under standard cell culture conditions. In those situations where the null or inducible conditional animal is viable (e.g., $p53^{-/-}$, $p19^{ARF-/-}$, or $p16^{-/-}$ mice), the derivation of cultured cells is straightforward and has been performed for a wide array of cell types in the case of several null mutant mice, e.g., $p53^{-/-}$ mice (Donehower, L. A., et al. *Semin. Cancer Biol.* 7:269-278; Harvey, M., et al. *Oncogene* 8:2457-67).

Since Dicer1 deficient null mice have been shown to exhibit embryonic lethality, deriving cultured cells from Dicer1 conditional knockout mice can prove to be problematical. Less differentiated cell types (e.g. embryonic fibroblasts) can often be obtained from mice that undergo late embryonic lethality, such as Rb null mice (Jacks, T., et al. *Nature* 359:295-300). However, mice displaying early embryonic lethality, such as Dicer1 null mice, may present greater obstacles in obtaining viable cells in culture. One way to circumvent this particular problem is to derive embryonic stem cells from homozygous mutant 3.5 day blastocysts after heterozygote crosses. In some cases, however, even this approach is impossible if the homozygous mutant state induces a cell lethal effect. (Such a phenotype has been observed in Chk1$^{-/-}$ cells (Liu, Q., et al. *Genes Dev.* 14:1448-1459). Even Chk1 null ES cells undergo rapid apoptosis.)

One widely studied cell type from transgenic mice is the embryo fibroblast. These are obtained from the mincing of midgestation mouse embryos (11-14 days post-coitus) and plating the fragments on plastic tissue culture dishes under standard medium conditions. Fibroblasts grow out and can be grown for about 10-25 passages before they decline in growth rate. Details of the embryo fibroblast derivation and culturing methods have been published elsewhere (Harvey, M., et al. *Oncogene* 8:2457-67; Freshney, I. R., in *Culture of Animal Cells: A Manual of Basic Technique*. Allan R. Liss, Inc., N.Y.). Once these cells are obtained, basic biological characterizations include standard growth curves, cell cycle analyses by flow cytometry, transformation susceptibility, response to DNA damage, genomic stability assays, and senescence assays. These transgenic cells and their wild type counterparts afford an excellent opportunity to compare the effects of relevant cancer-related and growth signaling pathways through standard biochemical assays.

The methods, animals and cell lines of the present invention will find commercial application, for example in biotechnology, drug development and medicine. For example, in biotechnology, the ability to rapidly develop large numbers of transgenic animals with desired modulation of specific genes will allow for the analysis of gene function and the evaluation of compounds that potentially modulate gene expression, protein function, and are useful in treating a disease or disorder. In particular, by observing the effect of down-regulating specific genes in transgenic animals, the biological function of those genes may be determined. In medicine the methods of the invention may be used to treat patients suffering from particular diseases or disorders, for example, neurological diseases or disorders, or to confer immunity or resistance to particular pathogens. For example, specific cells may be infected in vivo or ex vivo with recombinant retrovirus encoding a siRNA that down-regulates the activity of a gene whose activity is associated with a particular disease or disorder.

The skilled artisan will appreciate that the enumerated organisms are also useful for practicing other aspects of the invention, e.g., making transgenic organisms as described infra.

This invention is further illustrated by the following examples which should not be construed as limiting. The contents of all references, patents and published patent applications cited throughout this application are incorporated herein by reference.

EXAMPLES

The following materials, methods, and examples are illustrative only and not intended to be limiting.

Example I

LoxP-Flanked ("Floxed") Dicer1 Constructs

Exons 14, 15 and 16 of the mouse Dicer1 gene were selected for flanking with loxP sites. Deletions of these exons removed the PAZ functional domain and rendered the remaining coding sequences (those exons 3' of exon 16) out of frame with exons 1-13. This deletion therefore produces no functional Dicer protein. An EcoRI fragment from a BAC identified as containing the murine Dicer1 allele of a strain 129 mouse was isolated by standard methods (The BAC library is commercially available and was obtained from Invitrogen. It contains female mouse 129SV-strain genomic DNA inserted into the EcoR1 sites of the pBACe3.6 vector). This 8.6 kb EcoRI fragment (nucleotides numbered 31024 to 39625, refer to FIG. 1) was cloned into a pBluescript SK plasmid (vector 1; Stratagene). A BglII fragment was subcloned from vector1 into a separate pBluescript SK backbone cut with BglII and BamHI (vector2). This vector2 contained only a single HindIII site at 36036. A loxP site flanked by HindIII sites was inserted into the vector2 HindIII site at 36036 (vector3). The EcoR1 (31824) to BglII (34580) fragment of Dicer taken from vector1 was inserted into vector3, thus adding the 5' arm of homology to the vector (vector4). The BglII site in vector4 was changed to a Sal1 site using linkers (generating vector5). The 3' arm of homology was added by removing a Sac1 (37836) to Spe1 (located in the pBluescript SK polylinker of vector1 3' of the 3' terminal R1 site at 39630) fragment from vector1 and cloning it iinto vector5 that was restriction digested with Sac1 (37836 and Spe1). The resulting vector was vector6. Vector6 was opened at the Sal1 site (the former BglII site at 34580), and the floxed NEO TK cassette (encodes the Neomycin resistance gene and a thymidine kinase (TK) gene flanked by loxP sites) was inserted as a Sal1 fragment. This is the final targeting vector (vector7). Vector7 was screened for orientation of the loxP and floxed NEO-TK inserts (confirmation of orientation included performance of a Southern blot, using probes as indicated in FIG. 1, to ensure that the loxP sites were all sharing the same orientation with respect to each other within this construct.). Vector7 was then lineraized with AscI (located in the 5' polylinker), and electroporated into ES cells.

Example II

Genomic Integration of Targeting Vector

The resulting targeting vector contained 2756 bp of uninterrupted homology on the "left arm", and 3589 bp of uninterrupted homology on the "right arm" to the Dicer1 genomic sequence. Embryonic stem (ES) cells derived from 129 strain mice (refer to references of above ES cell sections for derivation of ES cell lines) were transfected using electroporation with this linearized targeting vector and screened by positive selection for the Neo marker. Surviving clones (Neomycin resistant) were screened by Southern analysis to identify those that had correctly integrated the targeting vector at the Dicer1 genomic locus. These clones were expanded, and Cre was added to induce recombination between the loxP sites. Following selection against the presence of the TK gene to identify only those clones having undergone Cre-mediated excision, Southern analysis confirmed that five clones (designated 3A11, 3A8, 3C2, 3C9, and 3B12, with clone 3A11 used in all subsequent methods and Examples) had undergone proper recombination of loxP sites to generate a conditional Dicer1 allele (refer to schematic of FIG. 1).

Example III

Generation of Dicer1 Conditional Mice

The above cells were injected into E3.5 blastocysts of 129 strain mice to generate chimeric mice by standard methods (refer to sections above regarding generation of transgenic animals) as offspring. Germline transmission of the floxed Dicer1 allele was assessed by crossing these chimeric mice with C57BL/6 strain mice. Agouti offspring heterozygous for the conditional Dicer1 allele were identified by Southern analysis of genomic DNA isolated from tail biopsies (refer to FIG. 4).

Example IV

Identification of a Dicer Requirement for Adipogenesis

To determine if Dicer and, by extension, miRNA molecules are required for adipogenesis, mouse embryonic fibroblasts (MEFs) harboring conditional Dicer1 alleles were assayed for the ability to differentiate into adipocytes in vitro. Several additional lines of Dicer-null MEFs were generated by infecting Dicer-conditional MEFs with either a recombinant adenovirus expressing the Cre recombinase gene (Ad-Cre) or with a control virus (Ad-Bgal). After confirming Cre-mediated deletion of the Dicer1 floxed gene region by Southern analysis in the Ad-Cre infected MEFs, the Dicer-deleted and Dicer-wt MEFs were expanded and the cells assayed for the ability to differentiate into adipocytes via addition of isobutylmethylxanthine (IBMX), dexamethasone, insulin, and the PPAR-$\gamma$ agonist Troglitazonethe to the media. Although differentiation was readily detected in the Dicer-wt MEFs as determined by staining of lipids with oil red O (ORO), cells that were deleted for Dicer failed to undergo differentiation into adipocytes, thereby demonstrating that Dicer is critical for adipogenesis (see FIG. 6).

It was reasoned that any block in adipocyte differentiation in Dicer-null cells would result from the loss of specific miRNA molecules needed to induce or maintain adipocyte differentiation. To confirm that miRNA molecules were indeed altered in these cells following loss of Dicer, the levels of two representative miRNA molecules (miR29A and miR193) were analyzed in Dicer-conditional MEFs that were either Ad-Cre infected or mock infected. The results revealed increased levels of pre-miRNA species and the absence of the mature miRNA species specifically in the Dicer-deleted cells.

Figure 7:
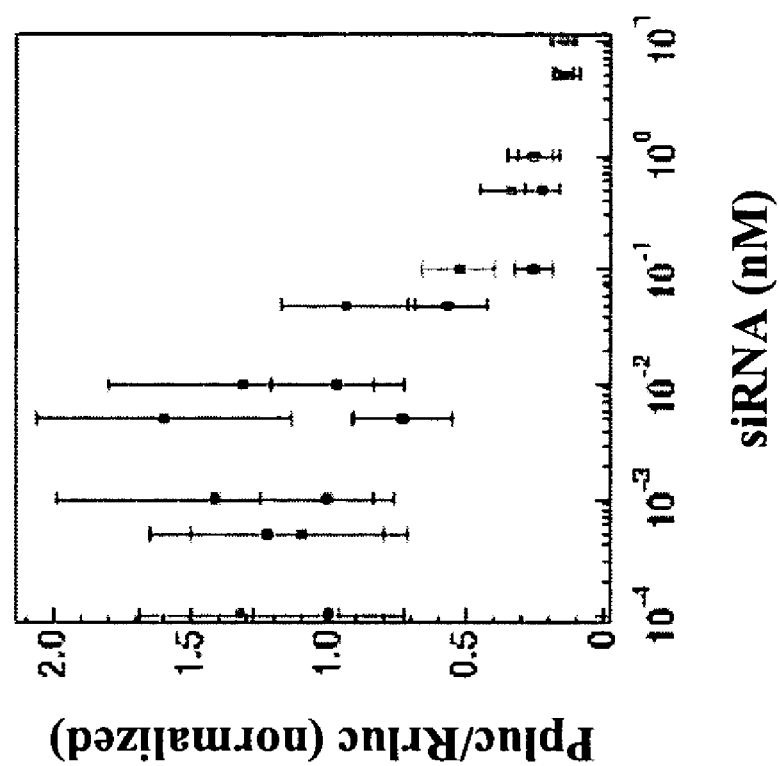
FIG. 7 graphically depicts that no significant difference exists between siRNA-mediated inhibition of gene expression in Dicer-wt and Dicer-deleted MEFs. A plasmid (Ppluc) encoding firefly luciferase was cotransfected into Dicer-conditional that were either mock-transduced (Ad-Bgal) or Cre-transduced (Ad-Cre) along with increasing amounts of an siRNA that targets the firefly luciferase RNA. The ratio of Ppluc to a Renilla luciferase control plasmid (Rrluc) was normalized to control transfections containing no siRNA. No significant difference was seen in siRNA-mediated suppression of target gene expression when Dicer was present or absent in the cells at siRNA concentrations>0.01 nM.

RNAi molecules representing specific miRNA species that, according to the literature, are upregulated or downregulated during adipocyte differentiation were reintroduced into the Dicer-null MEFs. RNA was harvested from Dicer-deleted or Dicer-wt MEFs to analyze alterations in miRNA species using a chip array representing known miRNA. (Such arrays are also used to analyze differences in miRNA species between non-differentiated and adipocyte-differentiated MEFs. Comparing the mouse miRNAs that are altered during differentiation to the published human data identifies specific miRNAs likely to play a role in adipocyte differentiation.) To confirm that exogenous siRNA functions in the absence of Dicer to inhibit target gene expression, Dicer-deleted MEFs or Dicer-wt MEFs were co-transfected with a firefly luciferase reporter construct and increasing amounts of siRNA that targets the luciferase RNA. The results (FIG. 7) showed that the RISC complex did not require Dicer to load siRNA molecules into the complex to inhibit the expression of target RNA.

These various results showed that Dicer is important in adipocyte differentiation. Furthermore, the ability to achieve sufficient differentiation in MEFs and the ability of the RISC complex to utilize the exogenous siRNA molecules to inhibit target RNA function in the absence of Dicer in MEFs exhibited the ability to use the Dicer-deleted MEFs to screen and identify miRNA molecules that are required for adipogenesis. In addition, an immortalized line of the Dicer-conditional MEFs has been generated using a 3T3 assay that can be tested in the differentiation assay. Additional data using the Dicer-conditional MEFs indicated that Dicer-deleted primary cells also failed to differentiate into melanocytes in culture, were highly prone to polyploidy yet maintained X-inactivation, and underwent premature senescence. Thus, these other results further demonstrated the utility of the Dicer-conditional MEFs in determining the role of Dicer and of miRNA in cell growth and cell differentiation.

Example V

Production of Mice Homozygous for the Dicer1 Conditional Allele

Agouti offspring heterozygous for the Dicer1 conditional allele are:
(1) Backcrossed for 6-12+ generations with C57BL/6J mice to generate congenic mice of homozygous C57BL/6J background (to control for effects induced by strain-specific genomic variability).
(2) Intercrossed to provide mice homozygous for the Dicer1 conditional allele.

Mice produced by either of these processes may be used to assess the effect(s) of spatially- and temporally-controlled Dicer1 deletions, via direct administration of the Cre recombinase or by breeding methods such as described below.

Example VI

Breeding and Analysis of Dicer1 Conditional Allele

Mice homozygous for the Dicer1 conditional allele are crossed with mice containing Cre recombinase-expressing constructs. Cre recombinase may be expressed in a variety of tissue- and temporal-specific patterns. Some patterns of Cre administration or expression allow for discrimination of the effect of Dicer1 deletion in, e.g., tissues of an adult mouse, and manipulation of Cre expression can enable precise control of RNAi pathway functionality on a tissue-by-tissue basis in a whole animal containing the Dicer1 conditional allele of the instant invention. Such precise manipulation of Dicer1 expression, and therefore RNAi pathway activity, provides a highly attractive model system for work involving siRNA and RNAi-directed agents, drugs and therapeutics. For example, siRNA directed against a transcript for which its absence is known to be deleterious in liver cells might be effectively globally administered to mice containing a conditional allele of Dicer1, and in which the Cre recombinase is specifically not expressed in liver but is expressed in other tissues. The effect of such an siRNA administration to the mouse in tissues other than liver might therefore be more reliably assessed.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant vector comprising sequence SEQ ID NO: 1.

2. A recombinant vector comprising sequence SEQ ID NO: 2.

3. An isolated cell or cell line comprising the recombinant vector of any one of claims 1, or 2.

4. An isolated cell or cell line comprising a genomically integrated form of the recombinant vector or portion thereof of any one of claims 1, or 2.

5. The cell or cell line of claim 4, wherein disruption of the Dicer1 conditional allele is induced by exposure to or expression of a recombinase.

6. The cell or cell line of claim 5, wherein disruption of the Dicer1 conditional allele is induced by exposure to or expression of the Cre recombinase.

7. The cell or cell line of claim 3, wherein the nucleic acid sequence of at least one exon of at least one genomic Dicer1 allele has been removed, wherein the altered genomic Dicer1 allele additionally comprises at least one site of inducible recombination.

8. The cell or cell line of any of claims 3 or 4, wherein the cell or cell line is of human origin.

9. The cell or cell line of any of claims 3 or 4, wherein the cell or cell line is an embryonic stem (ES) cell or cell line.

* * * * *

SEQUENCE LISTING

```
<160> NUMBER OF SEQ ID NOS: 3

<210> SEQ ID NO 1
<211> LENGTH: 11870
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 1
aattcatttt gattagatgt cgttttaaaa gatgggatgt agctgtgtta gaacccttgc      60
ctcataacgt gtgagaccct ggattctatc ccagcactac caaagtttaa aacaaatcgg     120
aacaactaga aggcttgaaa gcttgttggt attttcaaac taaagtactt ggttgtggca     180
gcttgggtgt cagcagtatt aggcagaggt tctgagtctg ccccgtgggc tggtaaacgt     240
aattgggaaa tgctctgttc ttgttttcag ggtccaccga tggacagtgt acggttggct     300
gaaagagtgg tagctctcat ttgctgtgaa aaactgcaca aaattggtat gtaaacatgc     360
ttggaaaaca tttatcagtg agaaaaaggt ggcaaagtgt ccgtcagaag cacatggagg     420
cctctgcggg tttctgggtt tgtcagggcc tagacatgct gctttgacta tacctcggtc     480
ggctcactat gccttttctg tacctcagag accctacaga gctgggcagg gctgctgact     540
ttcacagctt cactgtaaac agctgccact ttttgcttct gttgttggcc ccttttacac     600
acataaggat gctctaacta ttggattcta agccagccat atgtatgttt aatgtattag     660
```

```
actatgtcta atgtattaat gtattagaca tgtattaatg tattagacta tgtcaggtta    720
gtctatgtcg gtgaagaaga caatccttta aaaagtgaaa aacttgtgct taaaagggat    780
gtgtgagcct ggctagttga tattttaatt ttggatttta gagttaggtt tgttcatgct    840
gaatgcatga gtgtcacgta gagcccctaa agtttcagct gtgactactt tacagtgttt    900
gtgaggttta tctatcctat gtatgtgcgc ggttacttgc actgtgtgcc tgcctgctag    960
ctggagggca gatgaaggta cctgagccct ggaactgtac ttacagattg tcatgagtca   1020
ccatgtgggt gctgggaact agacctgggt cctctccgcg agcagccagt gctcctcact   1080
gctgagccag ctcttttcag tgtctaacgg caggggcgct tggttgctg tgctctgagt    1140
tgctccctca gcatggtgct cttttagatc atttactctt caggttgctg acataagcgc   1200
ttttaaactt cgtaggtgaa ctggatgaac acttgatgcc agttgggaaa gagactgtta   1260
aatatgaaga gagctggac ttacatgacg aggaggagac cagtgttccc gggagaccag    1320
ggtccacaaa acgacggcag tgctacccca agcagttag tattgcttag aactgaggaa    1380
cgtcagccgc tctcagttta tctcctgcca catcacatgc tacatcttct gctcagatgt   1440
ttccccaggt ccttgtgggt ctgtcttgtt cctctgattc ctggcgtctc cagagccgcc   1500
tttgtatttg agcataactg ttgctgggct ctgttgttcg gttttgtcat aagcctttcc   1560
aaaggattct tgaggcattt atcaaattat caaaaatatc aaaggagcat ctttcattta   1620
aaaaggcaca ttctttatt tatttatttt agtggtgtga ctctagcctt agtggccctt    1680
gctgtgacca tgactctcac agttagcggg tgaatgaaaa ggttgctttg ccgcggcggc   1740
cgggtctgtc aggagatgga ggaggctgtg ctgggagtgg gcagaggtcc ctgcagagca   1800
gcatctgcca gacctctgat gccccagcag ggctcagctc tcagcatctc atgcttgaca   1860
gaggctgatc tttaaaacat ggatattttc ttagtgtttt gtcttcacct aaatatttgg   1920
tcattttgtt tttgcagttt ttactttacg tatctgtacc ccagctaagc attttttcaag  1980
atttaaaagt cctgctttt ccctctccca acctttgtg taaagctttc accctcaagc     2040
ttacttgagc cactaaaggc atcggtgacg tctcctgaga gagatgcgcg ttctgtcttg   2100
ctcgctgccc ccgtgaccca cccatcttgt ctttagtact gcctcttagc ccgtgggtaa   2160
cagtgtaact gtgaactacc agtgtagacc ccaacctgtg agtctgagaa agttgaaaac   2220
tcagaaaatc tgaagtaatg atcacagtac tgattcactc tcataatgag agctgttaag   2280
aattacatta gagccagaga gctggttcag caggcctgat tgctggagtt ttagtccccg   2340
agaaccacat ggtaggatag ataacactgg ctctgtcagt gtcctctggg taccacagcc   2400
accgcagaca cacacatttt ctctctctgt ccaatagagg tcatgagtat taaaactgac   2460
actgatttgc gaaaggttgt cctgttgtag taactgaggc acaaactgct tgtctttctg   2520
tcccttctc cctcttcctg acctctcttc tcccctcctt tccctcttgc acatttacct    2580
tagctaagtc tctgttatga ttccatttat actgagaaat aaatttttc cccattggtg    2640
ccaagacaat gtgatttgta ccgtgaaaaa gatttttta atgaaatagt tttacaaata    2700
gtagagcata ttgaatgtta cctagagtga tggggttata tacaatatta aaaacagatc   2760
ggtcgacggt atcgataagc ttgatatcga attcgagctc gcccggggat ccggaaccct   2820
taatataact tcgtataatg tatgctatac gaagttatta ggtccctcga cctgcagccc   2880
aagcttgata tcgaattcta ccgggtaggg gaggcgcttt tcccaaggca gtctggagca   2940
tgcgctttag cagccccgct gggcacttgg cgctacacaa gtggcctctg gcctcgcaca   3000
cattccacat ccaccggtag gcgccaaccg gctccgttct ttggtggccc cttcgcgcca   3060
```

```
ccttctactc ctcccctagt caggaagttc ccccccgccc cgcagctcgc gtcgtgcagg   3120
acgtgacaaa tggaagtagc acgtctcact agtctcgtgc agatggacag caccgctgag   3180
caatggaagc gggtaggcct ttggggcagc ggccaatagc agctttgctc cttcgctttc   3240
tgggctcaga ggctgggaag gggtgggtcc ggggcgggc tcaggggcgg gctcaggggc    3300
ggggcgggcg cccgaaggtc ctccggaggc ccggcattct gcacgcttca aaagcgcacg   3360
tctgccgcgc tgttctcctc ttcctcatct ccgggccttt cgacctgcag ccaatatggg   3420
atcggccatt gaacaagatg gattgcacgc aggttctccg gccgcttggg tggagaggct   3480
attcggctat gactgggcac aacagacaat cggctgctct gatgccgccg tgttccggct   3540
gtcagcgcag gggcgcccgg ttcttttttgt caagaccgac ctgtccggtg ccctgaatga   3600
actgcaggac gaggcagcgc ggctatcgtg gctggccacg acgggcgttc cttgcgcagc   3660
tgtgctcgac gttgtcactg aagcgggaag ggactggctg ctattgggcg aagtgccggg   3720
gcaggatctc ctgtcatctc accttgctcc tgccgagaaa gtatccatca tggctgatgc   3780
aatgcggcgg ctgcatacgc ttgatccggc tacctgccca ttcgaccacc aagcgaaaca   3840
tcgcatcgag cgagcacgta ctcggatgga agccggtctt gtcgatcagg atgatctgga   3900
cgaagagcat caggggctcg cgccagccga actgttcgcc aggctcaagg cgcgcatgcc   3960
cgacggcgat gatctcgtcg tgacccatgg cgatgcctgc ttgccgaata tcatggtgga   4020
aaatggccgc ttttctggat tcatcgactg tggccggctg ggtgtggcgg accgctatca   4080
ggacatagcg ttggctaccc gtgatattgc tgaagagctt ggcggcgaat gggctgaccg   4140
cttcctcgtg ctttacggta tcgccgctcc cgattcgcag cgcatcgcct tctatcgcct   4200
tcttgacgag ttcttctgag gggatcaatt ctctagagct cgctgatcag cctcgactgt   4260
gccttctagt tgccagccat ctgttgtttg cccctccccc gtgccttcct tgaccctgga   4320
aggtgccact cccactgtcc tttcctaata aaatgaggaa attgcatcgc attgtctgag   4380
taggtgtcat tctattctgg ggggtggggt ggggcaggac agcaagggg aggattggga    4440 agacaatagc aggcatgctg gggatgcggt gggctctatg gcttctgagg cggaaagaac   4500
cagctggggc tcgagatcca ctagttctag cctcgaggct agagcggccg caacgataag   4560
cttgatctgg ccggggtccc gcggaaactc ggccgtggtg accaatacaa acaaaagcg    4620 ctcctcgtac cagcgaagaa ggggcagaga tgccgtagtc aggtttagtt cgtccggcgg   4680
cgccagaaat ccgcgcggtg gttttttgggg gtcggggtg tttggcagcc acagacgccc    4740
ggtgttcgtg tcgcgccagt acatgcggtc catgcccagg ccatccaaaa accatgggtc   4800
tgtctgctca gtccagtcgt ggactgaccc cacgcaacgc ccaaaataat aaccccccacg   4860 aaccataaac cattccccat gggggacccc gtccctaacc cacggggccc gtggctatgg   4920
cagggcctgc cgccccgacg ttggctgcga gccctgggcc ttcacccgaa cttgggggggt   4980 ggggtgggga aaaggaagaa acgcgggcgt attggcccca tggggtctc ggtggggtat    5040 cgacagagtg ccagccctgg gaccgaaccc cgcgtttatg aacaaacgac ccaacacccg   5100
tgcgttttat tctgtctttt tattgccgtc atagcgcggg ttccttccgg tattgtctcc   5160
ttccgtgttt cagttagcct cccccatctc ccgggcaaac gtgcgcgcca ggtcgcagat   5220
cgtcggtatg gagcctgggg tggtgacgtg ggtctggatc atcccggagg taagttgcag   5280
cagggcgtcc cggcagccgg cgggcgattg gtcgtaatcc aggataaaga cgtgcatggg   5340
acggaggcgt ttggccaaga cgtccaaggc ccaggcaaac acgttgtaca ggtcgccgtt   5400
```

```
gggggccagc aactcggggg cccgaaacag ggtaaataac gtgtccccga tatggggtcg    5460
tgggcccgcg ttgctctggg gctcggcacc ctggggcggc acggccgtcc ccgaaagctg    5520
tccccaatcc tcccgccacg acccgccgcc ctgcagatac cgcaccgtat tggcaagcag    5580
cccgtaaacg cggcgaatcg cggccagcat agccaggtca agccgctcgc cggggcgctg    5640
gcgtttggcc aggcggtcga tgtgtctgtc ctccggaagg gcccccaaca cgatgtttgt    5700
gccgggcaag atcggcggga tgagggccac gaacgccagc acggcctggg gggtcatgct    5760
gcccataagg tatcgcgcgg ccgggtagca caggagggcg gcgatgggat ggcggtcgaa    5820
gatgagggtg agggccgggg gcggggcatg tgagctccca gcctccccc cgatatgagg     5880 agccagaacg gcgtcggtca cggcataagg catgcccatt gttatctggg cgcttgtcat    5940
taccaccgcc gcgtccccgg ccgatatctc accctggtca aggcggtgtt gtgtggtgta    6000
gatgttcgcg attgtctcgg aagcccccag cacccgccag taagtcatcg gctcgggtac    6060
gtagacgata tcgtcgcgcg aacccagggc caccagcagt tgcgtggtgg tggttttccc    6120
catcccgtgg ggaccgtcta tataaacccg cagtagcgtg ggcattttct gctccgggcg    6180
gacttccgtg gcttcttgct gccggcgagg gcgcaacgcc gtacgtcggt tgctatggcc    6240
gcgagaacgc gcagcctggt cgaacgcaga cgcgtgctga tggccggggt acgaagccat    6300
acgcgcttct acaaggcgct ggccgaagag gtgcgggagt tcacgccac caagatctgc    6360 ggcacgctgt tgacgctgtt aagcgggtcg ctgcagggtc gctcggtgtt cgaggccaca    6420
cgcgtcacct aatatgcga agtggacctg ggaccgcgcc gccccgactg catctgcgtg     6480
ttcgaattcg ccaatgacaa gacgctgggc ggggtttgct cgacattggg tggaaacatt    6540
ccaggcctgg gtggagaggc tttttgcttc ctcttgcaaa accacactgc tcgacattgg    6600
gtggaaacat tccaggcctg ggtggagagg cttttgctt cctcttgaaa accacactgc     6660
tcgactctag aggatccgga acccttaata taacttcgta taatgtatgc tatacgaagt    6720
tattaggtcc ctcgacctgc agcccggggg atccactagt tctagagcgg ccgcgtcgac    6780
cgatctacct ttattttctg atactctgtg tgagtaaata gtttgaaaac tcacggaata    6840
aaaatgcttt tcagtcaaaa gaaatagatc aaatgattta atatttaaa aaggctattt      6900 taaatacttt tgatattcca taaaactgta ataagcagca taggtaaaat tgggcagtgt    6960
gcagctctgg cttcccacga gactcgatgc tgagtgcctt ctgagctgct gctgctgctt    7020
tgtttaaccc cacaaccaga aataaatgtc ttttcttgcc agcatctaga acaaaggctg    7080
attgtatttg agcatgatgc ttaattcttc tttccaactc tagattccag agtgcttgag    7140
ggagagttac cccaaacccg accagccttg ttacctgtat gtgataggaa tggtcttaac    7200
tacccccctc cctgatgaac tcaacttcag gcggcggaag ctctacccac ctgaggacac    7260
cacaagatgc tttgggatcc tgacagccaa acccatacct caggtaaacc cttcaccgag    7320
tctattgaca tagggatgga gtaagctaat gtcattgttg actaaaggta cccactcttc    7380
tttttgctaa gattcctcac tttcctgtgt atacacgctc tggagaggtc accatatcca    7440
tcgagctgaa gaagtctggt ttcacattgt ctcaacaaat gctcgagctg attacaagat    7500
tgcaccagta catattctca catattctcc ggcttgagaa gcctgccctg gagtttaaac    7560
ctacaggcgc ggagtcagcc tactgtgttc tacctcttaa tgttggtaag aaggggcctg    7620
cttgccaggg ttgctttatc tgggcagtga gtggtttgct ggtgactcac tcattgtgta    7680
tcccacgaat cctccttact tcactagctg tagactcaca ttagtgtacc ttaaatggaa    7740
atctcaccta tgttatattt aacctgttaa agtgtttttc ttcctgaagt taatgactcc    7800
```

```
ggcactttgg acattgactt taaattcatg gaggatattg agaagtcgga agctcggata   7860
ggcattccta gcaccaagta ttcaaaggaa acaccgtttg tctttaagtt agaagattac   7920
caagatgcag tgatcattcc aaggtgggtg tttcagtggg aaggaaaatg gcagtgggac   7980
ttgcttcagg tgtgcttgtc attgtggctg tggctgtgca ccatgtcacc agcatgcaga   8040
gggcagccag ggaaagtgtc tctctactca cgacatttaa aacaattcca agagcactg    8100
cagctgagag agttacattg tgaaaaatat tatttcttat ataataaat aatgttgcta    8160
gccttttaag aagtctctct tcccttaatt ccaaagtctt cctggagaat tcattgggg    8220
agaatgtgtg tgccttaagc ttataacttc gtaaatgta tgctatacga agttataagc    8280
tttcccagaa gtcattgtta ctccgcctgt ggaggtgggg aaggaaccac ttgacagagt   8340
tagggagtgg agcctgtggc agtccgtgat gtccgaatac ttgacaaaga attagagctg   8400
ggtgattgac tctgacttat atgcacgcat atcccttgtc ctttgccttc agtctctacc   8460
cctacccaga gtcgcattgt aaaggttgca ctagactatc actagcatag ataatgaaat   8520
acattttttt aatggtttta gagctttatt gtagaaaggc agagagagaa ggtcaaaata   8580
catcttctat atcagatacc gcatatttaa cataataatt tgcaaaggac ttactctgtt   8640
ggatattgca ttttctgttt tgattgtatt gatgaagcaa atatttgcag gaactattta   8700
tttagctttt aagattatca aaggaaagac atttagaaga agaataaggg ggaaatggag   8760
agcttgtttt acttaacaga aatatagttt ttattctcaa attcttgaaa tatttttttt   8820
ttggaattta aattctcatt aatgctattt acatttaatt atttgaactc tcaatgatgt   8880
gtttccatat taaaatagtt gtactttgaa gatagttgag ttacacaaaa ggcaacttga   8940
ttaattttct ttattttag ataccgcaat tttgatcagc ctcatcgatt ttatgtagct    9000
gatgtatata cggatcttac cccactcagt aaatttcctt ccctgaata tgaaacttt     9060
gcagaatatt ataaaacaaa gtaaaccctt gacctgacca atctcaacca gccactgctg   9120
gatgttgacc acacatcttc caggtaagag ccacagacat gatactgagg ttgcacaggg   9180
gggcttgctt tgtagggttc actgtacctc tgcctgctca tggcccctt ggacagactt    9240
gtctgtgttg tagaggagtg tgctgacaga gcaacttagg gaatgtgtag gcatacctaa   9300
gttggagttc taaccactgg gaggtgtact ttagtttgct ttttgataaa attgttctga   9360
aatttgtata gactgaacct tttgacacct cggcatttga atcagaaggg gaaagcactt   9420
cctctaagca gtgctgagaa gaggaaggcc aaatgggaaa gtctgcagaa caaacaggta   9480
atgaggtgct agtcacggga ctaagggttt tacattgctt cttttaagtt ttgaggttat   9540
tataatatga tgacatcatt tttctcttct ttcttcctg caagcactgc cgtgtagccc    9600
tccttactct tttcaaatt catgtccccg ttttcaata tgtacagcct gctcaagcat     9660
gacctaattt gaagtttcaa cattatcagt atagcaatga cctgtgagtt taggaaggtc   9720
gccatgggta ttgagtttac tttgaacatc cttgttggta aaacttgggt tttcctggcc   9780
actggtgcat tgggaatcac cttcataaat cccatttagg tataaaggat tagtttttaga  9840
agttaagtgt tgctagcact tacgattttc accatggtcc cttagtgaag ttggtcttta   9900
tattatgatt tgctttgctt tatacttacc agcctgtgct tttcttactc aaagatcctg   9960
gttccggaac tctgtgctat acatccaatc ccagcatcac tgtggagaaa agcggtttgt  10020
ctccccagca tactgtatcg ccttcactgc cttctgactg cagaggaact aagagctcag  10080
acagccagcg atgctggtgt gggtgtcaga tcacttcccg tggatttag gtatgcctgt   10140
```

-continued

```
gttgctggcc agaaatttga tttgcaacaa aatggaatta agttaaagtt gtattttcc    10200 tatagtttct aaaagatgac aaggaccatg tgcccattta acacatgaaa agaaactgta    10260
ctgtttatcc ctgaagtagc agactagacc attgagatct tgtcaagtta gagagcagca    10320 agcccctga accggatca ttgctcctgt agcagtgatg ctggaatagg ggtgagaatg      10380
gatatagttc ttctcaaaac taacctcatg ttagcagcag cagcctccgc tccttcttat    10440
tctggtcact tttttttcct gttagtgaac gtctgtatac caaagaaatc tttgtcgtaa    10500
ttaagtttgg tcatatagat agttgtagag gttgaaagca tcttaacata gtaatgtgag    10560
caatagtccc agttatccta cctgagtact tgatacagtc tgcaacacag cttaaacaa     10620 catgctctgt gctctatgct gacataggat gtattgatct catctccaag agcagaaatt    10680
gaggcacaga gaaagtttgt aagttgcaag aagctgctca cttggttcag gaggtgagcc    10740
cactaagcca gtagccactg caggacctcc acgttgggtc ctctcagtca gctctgcttt    10800
gccaccataa acagaagtca aagcagtaag ctgttctgca ttagaaccga ctgtgtgcag    10860
agtcccaggc agggccaggt aagcttggaa gtgcgttttc ttcttaggat gacttttaga    10920
gttgcttgct ttgtttgctt ttaactcaaa gtgttgcttt tctgagctta cccttttggag   10980 ggttgaaaga aagttataaa aatgtctttg cagatacct aacttagact tcgggtggaa     11040
aaaatctatt gatagcaagt ctttcatctc aagctgtaac tcctcgttgg ctgagagtga    11100
taattactgt aagcacagca caactgtagt ccctgaacat gctgcacatc aaggtgctac    11160
tagaccctcc ttagaaaacc atgaccaaat gtctgtgaac tgcaaaaggt tgcccgctga    11220
gtcacctgct aagctccaaa gtgaggtttc aacggatctt acagcaatta atggtctttc    11280
ttacaataaa aaccttgcca atggcagtta tgatttagtt aacagagact tttgccaagg    11340
aaatcagctg aattacttca agcaggaaat acctgtacaa ccaactacct catatcccat    11400 tcagaattig tacaattatg agaaccagcc caagcccagc aatgaatgtc tctactgag    11460 taatacgtac cttgatggga acgctaacac atctacctca gatggaagcc ccgcggtgtc    11520
cacgatgcct gccatgatga atgctgttaa agcactcaag gacaggatgg actctgagca    11580
gagcccttct gttgggtact cctcaaggac tcttggcccc aatccgggac tgattctcca    11640
ggctttgaca ctgtcaaatg ccagtgatgg gtttaacctg gagcggcttg agatgcttgg    11700
cgactccttt ttaaagcatg ctatcaccac atatctgttt tgcacgtacc ctgatgctca    11760
tgaaggccgc ctttcatata tgagaagcaa aaaggtaagg cacgattctc gttctgggct    11820
gttgcttctt cagtgtgcct gaaaacaggc caagttaccc atggggaatt              11870
```

<210> SEQ ID NO 2
<211> LENGTH: 5452
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 2

```
ataacttcgt ataatgtatg ctatacgaag ttattaggtc cctcgacctg cagcccaagc     60
ttgatatcga attctaccgg gtaggggagg cgcttttccc aaggcagtct ggagcatgcg    120
ctttagcagc cccgctgggc acttggcgct acacaagtgg cctctggcct cgcacacatt    180
ccacatccac cggtaggcgc caaccggctc cgttctttgg tggccccttc gcgccacctt    240
ctactcctcc cctagtcagg aagttccccc ccgccccgca gctcgcgtcg tgcaggacgt    300
```

```
gacaaatgga agtagcacgt ctcactagtc tcgtgcagat ggacagcacc gctgagcaat    360
ggaagcgggt aggcctttgg ggcagcggcc aatagcagct ttgctccttc gctttctggg    420
ctcagaggct gggaaggggt gggtccgggg gcgggctcag gggcgggctc aggggcgggg    480
cgggcgcccg aaggtcctcc ggaggcccgg cattctgcac gcttcaaaag cgcacgtctg    540
ccgcgctgtt ctcctcttcc tcatctccgg gcctttcgac ctgcagccaa tatgggatcg    600
gccattgaac aagatggatt gcacgcaggt tctccggccg cttgggtgga gaggctattc    660
ggctatgact gggcacaaca gacaatcggc tgctctgatg ccgccgtgtt ccggctgtca    720
gcgcagggc gcccggttct ttttgtcaag accgacctgt ccggtgccct gaatgaactg    780
caggacgagg cagcgcggct atcgtggctg gccacgacgg gcgttccttg cgcagctgtg    840
ctcgacgttg tcactgaagc gggaagggac tggctgctat gggcgaagt gccggggcag    900
gatctcctgt catctcacct tgctcctgcc gagaaagtat ccatcatggc tgatgcaatg    960
cggcggctgc atacgcttga tccggctacc tgcccattcg accaccaagc gaaacatcgc   1020
atcgagcgag cacgtactcg gatggaagcc ggtcttgtcg atcaggatga tctggacgaa   1080
gagcatcagg ggctcgcgcc agccgaactg ttcgccaggc tcaaggcgcg catgcccgac   1140
ggcgatgatc tcgtcgtgac ccatggcgat gcctgcttgc cgaatatcat ggtggaaaat   1200
ggccgctttt ctggattcat cgactgtggc cggctgggtg tggcggaccg ctatcaggac   1260
atagcgttgg ctacccgtga tattgctgaa gagcttggcg gcgaatgggc tgaccgcttc   1320
ctcgtgcttt acggtatcgc cgctcccgat tcgcagcgca tcgccttcta tcgccttctt   1380
gacgagttct tctgagggga tcaattctct agagctcgct gatcagcctc gactgtgcct   1440
tctagttgcc agccatctgt tgtttgcccc tcccccgtgc cttccttgac cctggaaggt   1500
gccactccca ctgtcctttc ctaataaaat gaggaaattg catcgcattg tctgagtagg   1560
tgtcattcta ttctgggggg tggggtgggg caggacagca agggggagga ttgggaagac   1620
aatagcaggc atgctgggga tgcggtgggc tctatggctt ctgaggcgga agaaccagc    1680
tggggctcga gatccactag ttctagcctc gaggctagag cggccgcaac gataagcttg   1740
atctggccgg ggtcccgcgg aaactcggcc gtggtgacca atacaaaaca aaagcgctcc   1800
tcgtaccagc gaagaagggg cagagatgcc gtagtcaggt ttagttcgtc cggcggcgcc   1860
agaaatccgc gcggtggttt ttgggggtcg ggggtgtttg gcagccacag acgcccggtg   1920
ttcgtgtcgc gccagtacat gcggtccatg cccaggccat ccaaaaacca tgggtctgtc   1980
tgctcagtcc agtcgtggac tgaccccacg caacgcccaa aataataacc cccacgaacc   2040
ataaaccatt ccccatgggg gacccgtcc ctaacccacg gggcccgtgg ctatggcagg   2100
gcctgccgcc ccgacgttgg ctgcgagccc tgggccttca cccgaacttg ggggtgggg    2160
tggggaaaag gaagaaacgc gggcgtattg gccccaatgg ggtctcggtg ggtatcgac    2220
agagtgccag ccctgggacc gaaccccgcg tttatgaaca aacgaccaa cacccgtgcg    2280
ttttattctg tctttttatt gccgtcatag cgcgggttcc ttccggtatt gtctccttcc   2340
gtgtttcagt tagcctcccc catctcccgg gcaaacgtgc gcgccaggtc gcagatcgtc   2400
ggtatggagc ctgggtggt gacgtgggtc tggatcatcc cggaggtaag ttgcagcagg   2460
gcgtcccggc agccggcggg cgattggtcg taatccagga taaagacgtg catgggacgg   2520
aggcgtttgg ccaagacgtc caaggcccag gcaaacacgt tgtacaggtc gccgttgggg   2580
gccagcaact cggggccccg aaacagggta aataacgtgt cccgatatg gggtcgtggg   2640
cccgcgttgc tctggggctc ggcaccctgg ggcggcacgg ccgtccccga aagctgtccc   2700
```

-continued

```
caatcctccc gccacgaccc gccgccctgc agataccgca ccgtattggc aagcagcccg    2760
taaacgcggc gaatcgcggc cagcatagcc aggtcaagcc gctcgccggg gcgctggcgt    2820
ttggccaggc ggtcgatgtg tctgtcctcc ggaagggccc ccaacacgat gtttgtgccg    2880
ggcaagatcg gcgggatgag ggccacgaac gccagcacgg cctgggggt catgctgccc     2940
ataaggtatc gcgcggccgg gtagcacagg agggcggcga tgggatggcg gtcgaagatg    3000
agggtgaggg ccggggcgg ggcatgtgag ctcccagcct cccccccgat atgaggagcc     3060
agaacggcgt cggtcacggc ataaggcatg cccattgtta tctgggcgct tgtcattacc    3120
accgccgcgt ccccggccga tatctcaccc tggtcaaggc ggtgttgtgt ggtgtagatg    3180
ttcgcgattg tctcggaagc ccccagcacc cgccagtaag tcatcggctc gggtacgtag    3240
acgatatcgt cgcgcgaacc cagggccacc agcagttgcg tggtggtggt tttccccatc    3300
ccgtggggac cgtctatata aacccgcagt agcgtgggca ttttctgctc cgggcggact    3360
tccgtggctt cttgctgccg gcgagggcgc aacgccgtac gtcggttgct atggccgcga    3420
gaacgcgcag cctggtcgaa cgcagacgcg tgctgatggc cggggtacga agccatacgc    3480
gcttctacaa ggcgctggcc gaagaggtgc gggagtttca cgccaccaag atctgcggca    3540
cgctgttgac gctgttaagc gggtcgctgc agggtcgctc ggtgttcgag gccacgcg     3600
tcaccttaat atgcgaagtg gacctgggac cgcgccgccc cgactgcatc tgcgtgttcg    3660
aattcgccaa tgacaagacg ctgggcgggg tttgctcgac attgggtgga aacattccag    3720
gcctgggtgg agaggcttt tgcttcctct tgcaaaacca cactgctcga cattgggtgg      3780
aaacattcca ggcctgggtg gagaggcttt tgcttcctc ttgaaaacca cactgctcga      3840
ctctagagga tccggaaccc ttaatataac ttcgtataat gtatgctata cgaagttatt    3900
aggtccctcg acctgcagcc cggggatcc actagttcta gagcggccgc gtcgaccgat     3960
ctacctttat tttctgatac tctgtgtgag taaatagttt gaaaactcac ggaataaaaa    4020
tgcttttcag tcaaaagaaa tagatcaaat gatttaatat tttaaaaagg ctattttaaa    4080
tactttttgat attccataaa actgtaataa gcagcatagg taaaattggg cagtgtgcag    4140
ctctggcttc ccacgagact cgatgctgag tgccttctga gctgctgctg ctgctttgtt    4200
taaccccaca accagaaata aatgtctttt cttgccagca tctagaacaa aggctgattg    4260
tatttgagca tgatgcttaa ttcttctttc caactctaga ttccagagtg cttgagggag    4320
agttacccca aacccgacca gccttgttac ctgtatgtga taggaatggt cttaactacc    4380
cccctccctg atgaactcaa cttcaggcgg cggaagctct acccacctga ggacaccaca    4440
agatgctttg ggatcctgac agccaaaccc atacctcagg taaacccttc accgagtcta    4500
ttgacatagg gatggagtaa gctaatgtca ttgttgacta aaggtaccca ctcttctttt    4560
tgctaagatt cctcactttc ctgtgtatac acgctctgga gaggtcacca tatccatcga    4620
gctgaagaag tctggtttca cattgtctca acaaatgctc gagctgatta caagattgca    4680
ccagtacata ttctcacata ttctccggct tgagaagcct gccctggagt ttaaacctac    4740
aggcgcggag tcagcctact gtgttctacc tcttaatgtt ggtaagaagg ggcctgcttg    4800
ccagggttgc tttatctggg cagtgagtgg tttgctggtg actcactcat tgtgtatccc    4860
acgaatcctc cttacttcac tagctgtaga ctcacattag tgtaccttaa atggaaatct    4920
cacctatgtt atatttaacc tgttaaagtg ttttcttcc tgaagttaat gactccggca     4980
ctttggacat tgactttaaa ttcatggagg atattgagaa gtcggaagct cggataggca    5040
```

-continued

```
ttcctagcac caagtattca aaggaaacac cgtttgtctt taagttagaa gattaccaag    5100
atgcagtgat cattccaagg tgggtgtttc agtgggaagg aaaatggcag tgggacttgc    5160
ttcaggtgtg cttgtcattg tggctgtggc tgtgcaccat gtcaccagca tgcagagggc    5220
agccagggaa agtgtctctc tactcacgac atttaaaaca attccaaaga gcactgcagc    5280
tgagagagtt acattgtgaa aaatattatt tcttatataa ataaataatg ttgctagcct    5340
tttaagaagt ctctcttccc ttaattccaa agtcttcctg gagaatttca ttggggagaa    5400
tgtgtgtgcc ttaagcttat aacttcgtat aatgtatgct atacgaagtt at           5452
```

<210> SEQ ID NO 3
<211> LENGTH: 34
<212> TYPE: DNA
<213> ORGANISM: Mus musculus

<400> SEQUENCE: 3

```
ataacttcgt ataatgtatg ctatacgaag ttat                                 34
```